(12) United States Patent
McDaniel

(10) Patent No.: US 6,676,655 B2
(45) Date of Patent: Jan. 13, 2004

(54) LOW INTENSITY LIGHT THERAPY FOR THE MANIPULATION OF FIBROBLAST, AND FIBROBLAST-DERIVED MAMMALIAN CELLS AND COLLAGEN

(75) Inventor: David H. McDaniel, Virginia Beach, VA (US)

(73) Assignee: Light BioScience L.L.C., Virginia Beach, VA (US)

(*) Notice: Subject to any disclaimer, the term of this patent is extended or adjusted under 35 U.S.C. 154(b) by 0 days.

(21) Appl. No.: 10/119,772

(22) Filed: Apr. 11, 2002

(65) Prior Publication Data

US 2003/0004556 A1 Jan. 2, 2003

Related U.S. Application Data

(60) Continuation-in-part of application No. 09/894,899, filed on Jun. 29, 2001, which is a continuation-in-part of application No. 09/819,081, filed on Feb. 15, 2001, now Pat. No. 6,629,971, which is a division of application No. 09/203,178, filed on Nov. 30, 1998, now Pat. No. 6,283,956.

(51) Int. Cl.[7] .............................................. A61B 18/18
(52) U.S. Cl. ..................... 606/9; 606/3; 606/8; 607/88; 607/90; 607/91
(58) Field of Search .............................. 606/3–5, 7–13, 606/16, 20–23, 32–34; 607/88–91, 96–101; 128/898

(56) References Cited

U.S. PATENT DOCUMENTS

| | | |
|---|---|---|
| 4,458,678 A | 7/1984 | Yannas et al. |
| 4,646,743 A | 3/1987 | Parris |
| 4,767,402 A | 8/1988 | Kost et al. |
| 4,836,203 A | 6/1989 | Muller et al. |
| 4,888,354 A | 12/1989 | Chang et al. |
| 4,930,504 A | 6/1990 | Diamantopoulos et al. |
| 4,969,912 A | 11/1990 | Kelman et al. |
| 5,021,452 A | 6/1991 | Labbe et al. |
| 5,037,432 A | 8/1991 | Molinari |
| 5,147,349 A * | 9/1992 | Johnson et al. ............... 606/4 |
| 5,198,465 A | 3/1993 | Dioguardi |
| 5,226,907 A | 7/1993 | Tankovich |
| 5,231,975 A | 8/1993 | Bommannan et al. |
| 5,259,380 A * | 11/1993 | Mendes et al. ............ 607/115 |
| 5,266,480 A | 11/1993 | Naughton et al. |
| 5,332,802 A | 7/1994 | Kelman et al. |
| 5,358,503 A | 10/1994 | Bertwell et al. |
| 5,366,498 A | 11/1994 | Brannan et al. |
| 5,397,352 A | 3/1995 | Burres |
| 5,423,803 A * | 6/1995 | Tankovich et al. ............ 606/9 |
| 5,425,728 A | 6/1995 | Tankovich |
| 5,445,146 A | 8/1995 | Bellinger |
| 5,445,634 A | 8/1995 | Keller |
| 5,460,939 A | 10/1995 | Hansbrough et al. |
| 5,474,528 A | 12/1995 | Meserol |

(List continued on next page.)

OTHER PUBLICATIONS

Wei Yu et al. "Improvement of Host Response to Sepsis by Photobiomodulation" Lasers in Surgery and Medicine, 21:262–268, 1997.

(List continued on next page.)

Primary Examiner—Linda C. M. Dvorak
Assistant Examiner—Ahmed Farah
(74) Attorney, Agent, or Firm—Morrison & Foerster, LLP

(57) ABSTRACT

Disclosed is a method for treating various dermatalogical conditions using electromagnetic radiation. Particularly preferred are narrowband, multichromatic electromagnetic radiation emitters having a dominant emissive wavelength corresponding to the peak absorption wavelength of the mammalian tissue targetted for treatment. Topical compositions are disclosed for pretreating the targetted tissue to alter the peak absorption wavelength of the tissue.

24 Claims, 38 Drawing Sheets

U.S. PATENT DOCUMENTS

| | | | | |
|---|---|---|---|---|
| 5,492,135 | A | * | 2/1996 | DeVore et al. ............... 128/898 |
| 5,591,444 | A | | 1/1997 | Boss, Jr. |
| 5,620,478 | A | | 4/1997 | Eckhouse |
| 5,643,334 | A | * | 7/1997 | Eckhouse et al. ............. 607/88 |
| 5,647,866 | A | | 7/1997 | Zaias et al. |
| 6,050,990 | A | * | 4/2000 | Tankovich et al. ............. 606/9 |
| 6,063,108 | A | | 5/2000 | Salansky et al. |
| 6,096,066 | A | | 8/2000 | Chen et al. |
| 6,162,211 | A | * | 12/2000 | Tankovich et al. ............. 606/9 |
| 6,187,029 | B1 | * | 2/2001 | Shapiro et al. ................ 607/88 |
| 6,251,127 | B1 | | 6/2001 | Biel |
| 2001/0023363 | A1 | | 9/2001 | Harth et al. |

OTHER PUBLICATIONS

Abergel et al., "Biostimulation of Wound Healing by Lasers: Experimental Approaches in Animal Models and in Fibroblast Cultures" J. Dermatol. Surg. Oncol., 13:2, Feb. 1987.

Van Breugel et al., "Power Density and Exposure Time of H–Ne Laser Irradiation are More Important than Total Energy Dose in Photo–Biomodulation of Human Fibroblasts in Vitro" Lasers in Surgery and Medicine, 12:528–537, 1992.

Sumian et al., "A New Method to Improve Penetration Depth of Dye into the Follicular Duct: Potential Application for Laser Hail Removal".

Whelan et al. "NASA Light Emitting Diode Medical Applications From Deep Space to Deep Sea" CP552, Space Technology and Applications International Forum–2001, pp. 35–45.

ABSTRACT—Ceccherelli et al.; Diode laser in cervical myofascial pain: a double–blind study versus placebo; The Clinical Journal of Pain vol. 5, pp. 301–304, 1989.

ABSTRACT—Karu et al.; Effects of monochromatic low–intensity light and laser irradiation on adhesion of HeLa cells in vitro; Lasers Surg. Med. 18(2), pp. 171–177, 1996.

ABSTRACT—Chung et al.; Histological repsonses of port wine stains in brown skin after 578 nm copper vapor laser treatment; Lasers Surg. Med. 18(4), pp. 358–366, 1996.

ABSTRACT—Callaghan et al.; Reactive oxygen species inducible by low–intensity laser irradiation alter DNA synthesis in the haemopoietic cell line U937; Lasers Surg. Med. 19(2), pp. 201–206, 1996.

ABSTRACT—Laakso et al.; Pain scores and side effects in response to low level laser therapy (LLLT) for myofascial trigger points; Laser Therapy vol. 9, pp. 67–72, 1997.

ABSTRACT—Logdberg–Anderssont et al.; Low level laser therapy (LLLT) of tendinitis and myofascial pains a randomized, double–blind, controlled study; Laser Therapy vol. 9, pp. 79–86, 1997.

Liberman et al.; Light Years Ahead; 1996, pp. 277–283.

* cited by examiner

LOW INTENSITY LIGHT THERAPY FOR THE MANIPULATION OF FIBROBLAST, AND FIBROBLAST-DERIVED MAMMALIAN CELLS AND COLLAGEN

This application is a continuation-in-part of U.S. application Ser. No. 09/894,899, which is a continuation-in-part of U.S. application Ser. No 09/819,081, filed Feb. 15, 2001 now U.S. Pat. No. 6,629,971, which is a divisional application of U.S. application Ser. No. 09/203,178, filed Nov. 30, 1998 now U.S. Pat. No. 6,283,956.

FIELD OF THE INVENTION

The present invention generally relates to a system and method for the use of low-intensity light therapy alone or in combination with various topical compositions. Various medically beneficial results can be obtained by using combinations of photothermal, photochemical, photodynamic and photomodulatory means and applying a cosmeceutical or drug composition, naturally occuring or synthetic or genetically engineered topical or systemically delivered chromophores, or other light-activated chromophores onto or into mammalian tissue and exposing the composition to electromagnetic radiation.

BACKGROUND OF THE INVENTION

Low-intensity light therapy is an emerging field of study wherein light emitting diodes and other emitters of low-intensity electromagnetic radiation are used to treat various medical conditions such as acne, hair growth stimulation, hair growth inhibition, scar reduction and removal, wrinkle reduction, etc. This is in stark contrast to prior art approaches that used high-intensity monochromatic light to treat such conditions.

For example, a known technique for hair removal uses a short pulsed laser to produce a wavelength that may be absorbed by a "foreign" material or "skin contaminant". Aspects of this technique are described, for example, in U.S. Pat. Nos. 5,423,803, 5,817,089, 5,425,728, 5,226,907, and 5,752,949, all of which are incorporated by reference. This contaminant may be applied directly onto the skin and may be introduced into the empty space surrounding the hair shaft. One contaminant that has been used is carbon graphite in particulate form. The graphite particles have a diameter that is small enough to enable the particles to drop from the surface of the skin into the free empty spaces between the duct and the hair shaft. The energy from a laser may then interact with the contaminant particles. This causes injury to surrounding tissues whose function is to support the growth of the hair shaft. This tends to reduce or eliminate hair growth.

These contaminant particles are not physically incorporated into the hair shaft or into the surrounding hair follicle, hair bulge or hair duct cells. Nor do these contaminant particles chemically, immunologically, biologically or otherwise interact, react or complex with the hair shafts or tissue cells. The contaminant particles simply physically occupy the space surrounding the hair shaft.

Another known hair removal technique is to use a pulsed electromagnetic radiation source to produce a wavelength that may be absorbed by hair, as described, for example, in U.S. Pat. No. 5,683,380, which is incorporated by reference.

There are problems with present light and laser hair removal techniques. Known melanin targeting systems work reasonably well and are reasonably safe only when the color of the hair is very dark and when the skin is very light and not tanned. Virtually all light sources which tend to target melanin are also inherently absorbed by the overlying and surrounding skin. At present, these light sources cannot be safely used at optimal very high power settings for people with darker skin or even people with a dark tan.

In another example, there is a known hair removal process which uses a 1064 nm laser to produce a wavelength that may be absorbed by a skin contaminant appears to be safe on all skin colors, including darker skin colors. However, this safety is a consequence of there being very little melanin absorption. It is therefore necessary to add graphite particles in oil contaminant lotion before laser treatment. This graphite particle lotion does not enter into the hair shaft itself. Instead, the graphite lotion tends to occupy empty spaces surrounding the hair shaft as it sits in the hair duct. This presents a problem. Either an insufficient or sub-optimal number of graphite particles penetrate into the hair duct, or an insufficient amount of damage is caused by the graphite particles. Consequently, many treatments tend to be required before an acceptable result is achieved.

SUMMARY OF THE INVENTION

The present invention is to a method for the manipulation of collagen, fibroblast, and fibroblast-derived cell levels in mammalian tissue comprising the steps of exposing the tissue to a plurality of pulses from at least one source of narrowband, multichromatic electromagnetic radiation having a dominant emissive wavelength of from about 300 nm to about 1600 nm, and wherein said pulses have a duration of from about 0.1 femtoseconds to about 100 seconds, the interpulse delay between said pulses is from about 0.1 to about 1000 milliseconds, and the energy fluence received by said tissue is less than about 10 joule per square centimeter.

In another embodiment of the invention, the source of narrowband, multichromatic electromagnetic radiation is selected from a light emitting diode, a laser, a fluorescent light source, an organic light emitting diode, a light emitting polymer, a xenon arc lamp, a metal halide lamp, a filamentous light source, an intense pulsed light source, a sulfur lamp, and combinations thereof, and the dominant emissive wavelength is from about 400 nm to about 1600 nm.

In another embodiment of the invention, the source of narrowband, multichromatic electromagnetic radiation further comprises a filter element for reducing the intensity of infrared radiation received by said tissue It is preferred that the energy fluence received at the tissue is 1 $J/cm^2$ or less or, alternatively, that the energy fluence received at the tissue is greater than 1 $J/cm^2$ and the tissue is cooled. In another embodiment of the invention, the energy fluence received at said tissue is from about from about $1\times10^{-6}$ $J/cm^2$ to 1 $J/cm^2$ or, alternatively, the energy fluence received at said tissue is from about from about $1\times10^{-3}$ $J/cm^2$ to about 0.1 $J/cm^2$.

According to the present invention, pulse length is from about 1 nanosecond to about 1 second and, preferably, the pulse length is from about 5 nanoseconds to about 100 milliseconds.

In an embodiment of the invention, source of electromagnetic radiation is filtered to reduce the energy fluence of infrared radiation or is filtered to reduce the perception by the tissue of radiation having a wavelength greater than about 700 nm.

In another embodiment of the invention, a topical composition may be applied to the skin or target tissue prior to exposure to electromagnetic radiation. The topical composition is selected from the group consisting of naturally occurring chlorophyll-containing compounds, carotenoid-containing compounds, phyocobilin compounds, indocyanine green, methylene blue, rose Bengal, Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a cofactor, an antiaging substance, insulin, minoxidil, lycopene, a natural or synthetic melanin, a metalloproteinase inhibitor, proline, hydroxyproline, an anesthetic, chlorophyll, bacteriochlorophyll, copper chlorophyllin, chloroplasts, carotenoids, phycobilin, rhodopsin, anthocyanin, inhibitors of ornithine decarboxylase, inhibitors of vascular endothelial growth factor (VEGF), inhibitors of phospholipase A2, inhibitors of S—adenosylmethionine, licorice, licochalone A, genestein, soy isoflavones, phtyoestrogens, derivative, analogs, homologs, and subcomponents thereof, and derivatives, subcomponents, immunological complexes and antibodies of said target tissue, and synthetic and natural analogs thereof, and combinations thereof.

In another embodiment of the present method for the manipulation of collagen, fibroblast, and fibroblast-derived cell levels in mammalian tissue, the method comprises exposing the tissue to at least one source of narrowband, multichromatic electromagnetic radiation having a dominant emissive wavelength of from about 300 nm to about 1600 nm for a period of time of from about 10 seconds to about 24 hours, wherein the energy fluence received by said tissue is less than about 10 J/cm$^2$.

It is preferred that the source of narrowband, multichromatic electromagnetic radiation is selected from a light emitting diode, a laser, a fluorescent light source, an organic light emitting diode, a light emitting polymer, a xenon arc lamp, a metal halide lamp, a filamentous light source, a sulfur lamp, and combinations thereof, and has a dominant emissive wavelength is from about 400 nm to about 1600 nm. The source of narrowband, multichromatic electromagnetic radiation may further comprise a filter element for reducing the intensity of infrared radiation received by said tissue According to the continuous wave embodiment of the invention, the energy fluence received at the tissue is 1 J/cm$^2$ or less. The energy fluence received at the tissue can be greater than 1 J/cm$^2$ when the method further comprises cooling the tissue.

The method of the present invention may further comprise cooling the tissue to maintain a temperature of said tissue below the threshold for thermal injury and may further comprise maintaining the temperature of the tissue at or below 38° C.

BRIEF DESCRIPTION OF THE DRAWINGS

FIG. 9 shows the absorption spectrum for human fibroblast overlayed with lines indicating the dominant emissive wavelength of some commercially available LEDs and also the absorption spectrum for chlorophyll a.

Figure 1A:
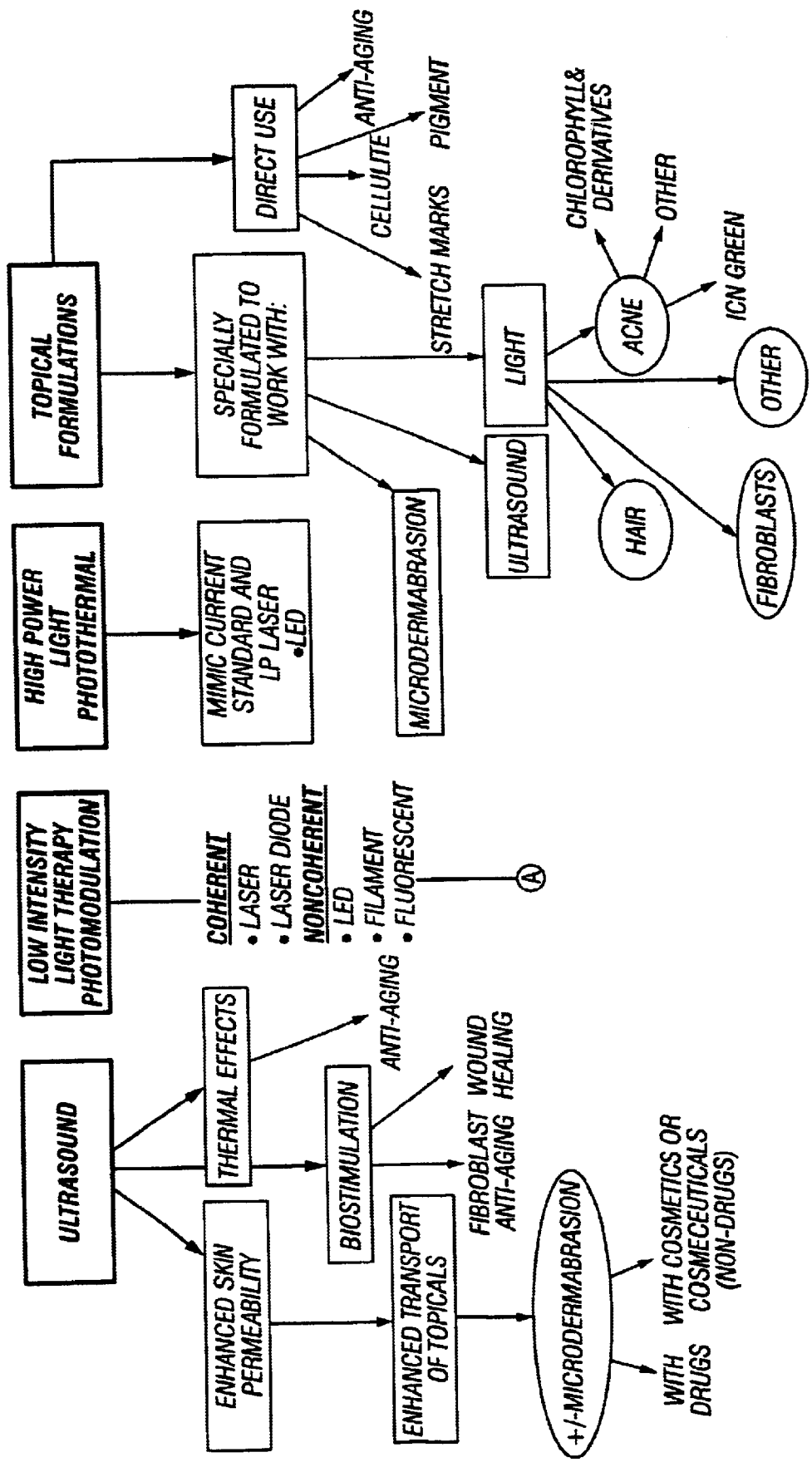
FIGS. 1a and 1b are schematical illustrations of various treatment regimens, including the low level light method of the present invention which may also incorporate the use of topical formulations.
Figure 1B:
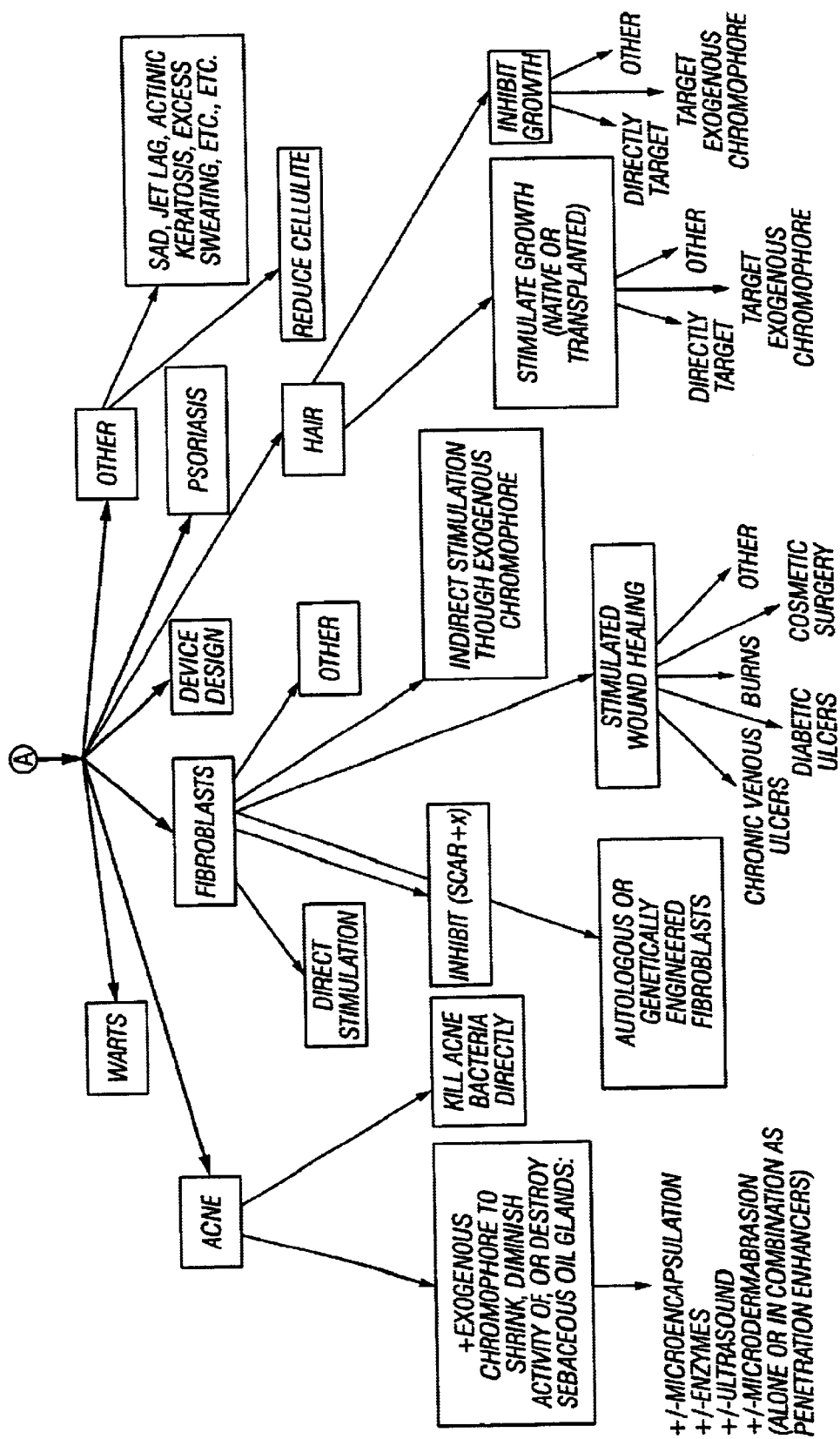
Figure 2A:
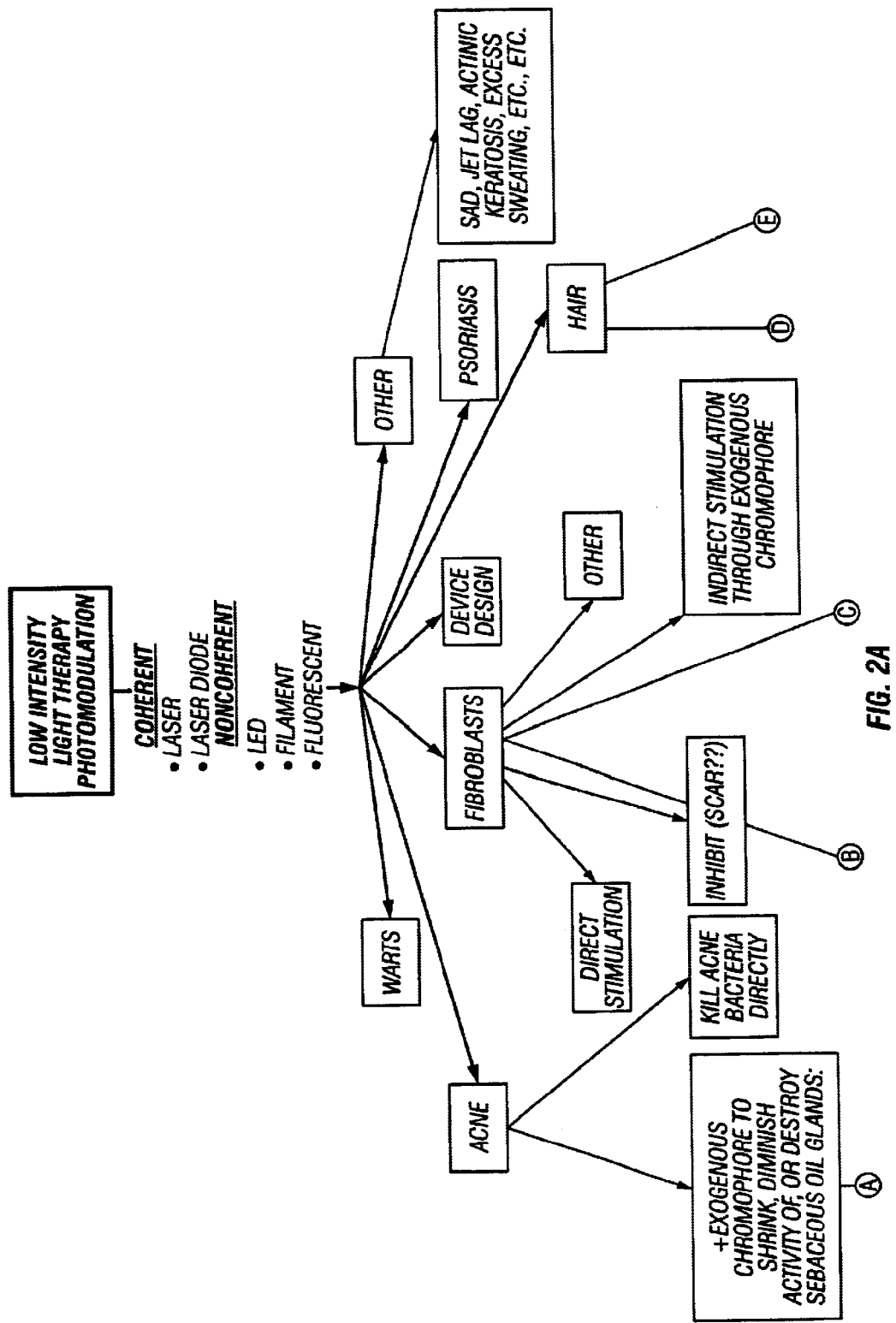
FIGS. 2a and 2b are flow chart illustrations showing various treatment regimen for various skin-related treatments.
Figure 2B:
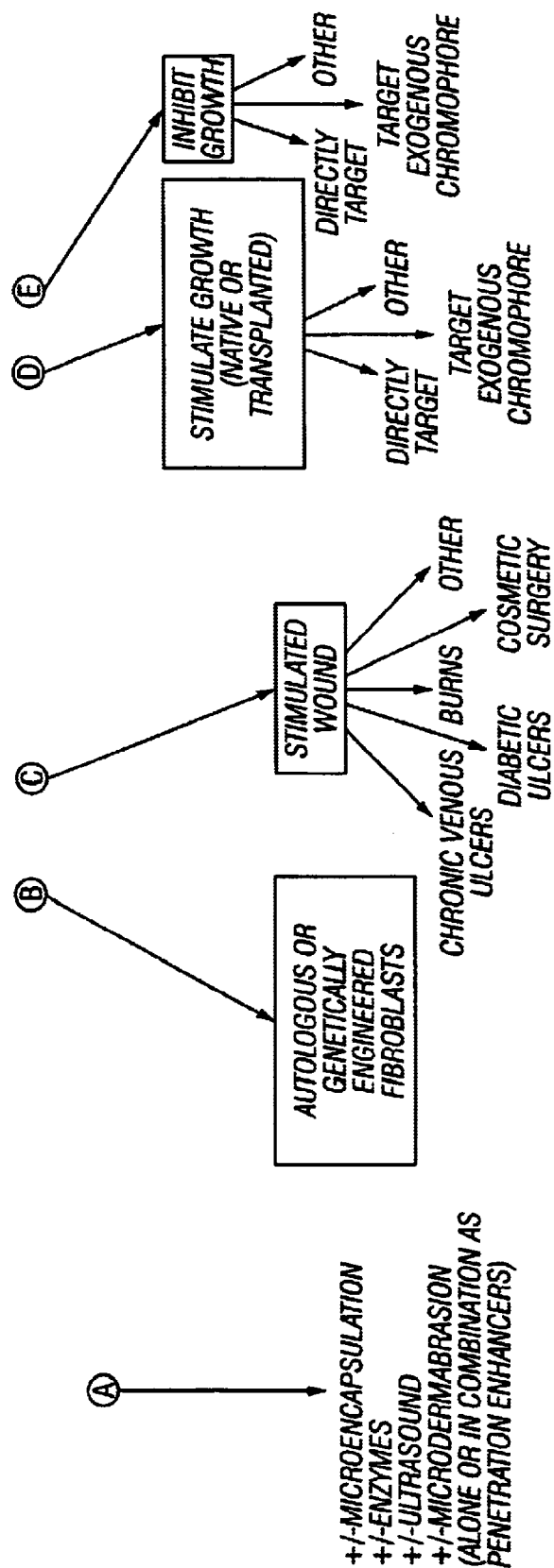
Figure 3:
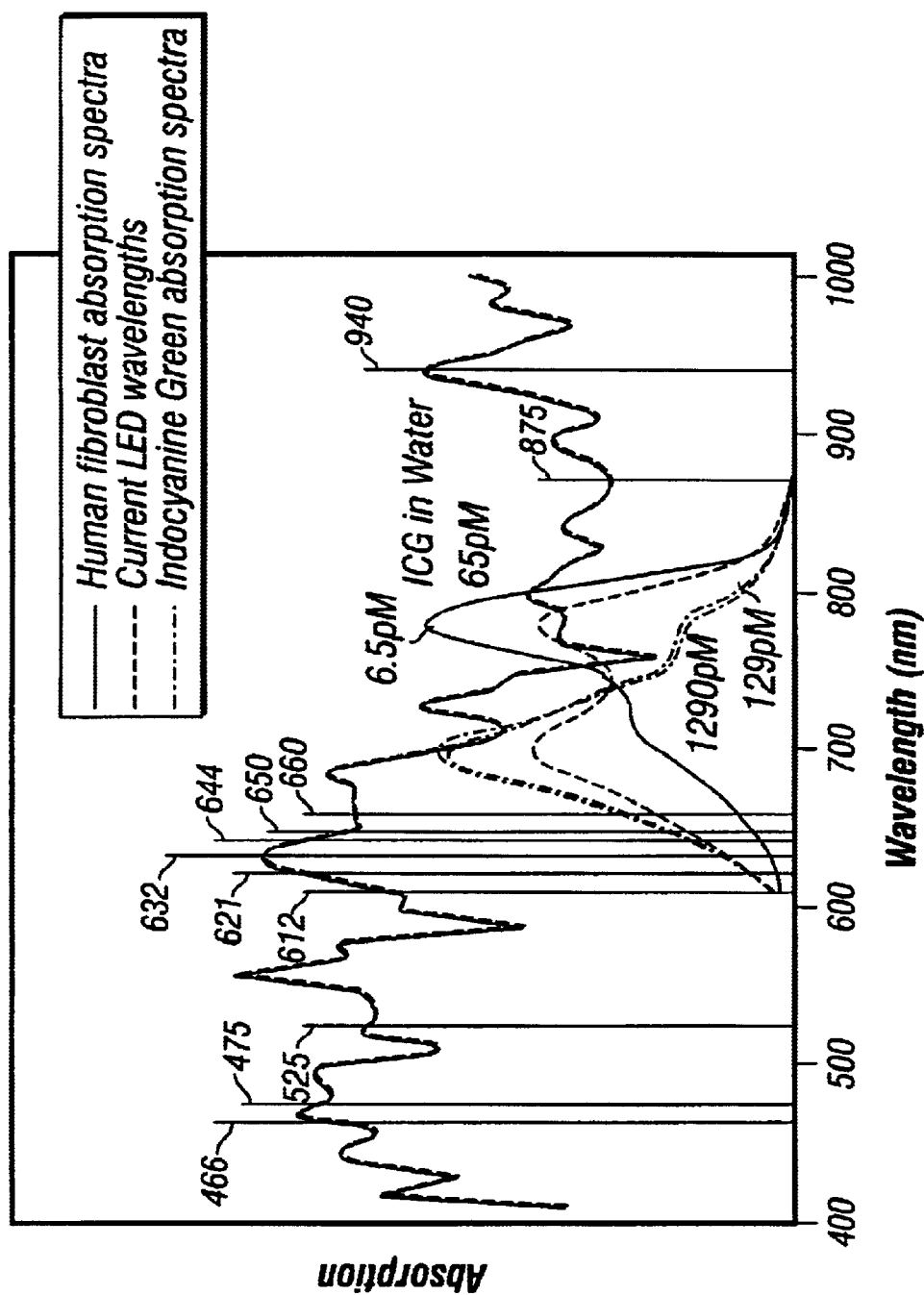
FIG. 3 is a graphical illustration of the absorption spectrum of human fibroblast overlayed with the wavelengths used by narrowband, multichromatic LED emitters of the present invention and also the absorption spectrum of indocyanine green (ICG).
Figure 4:
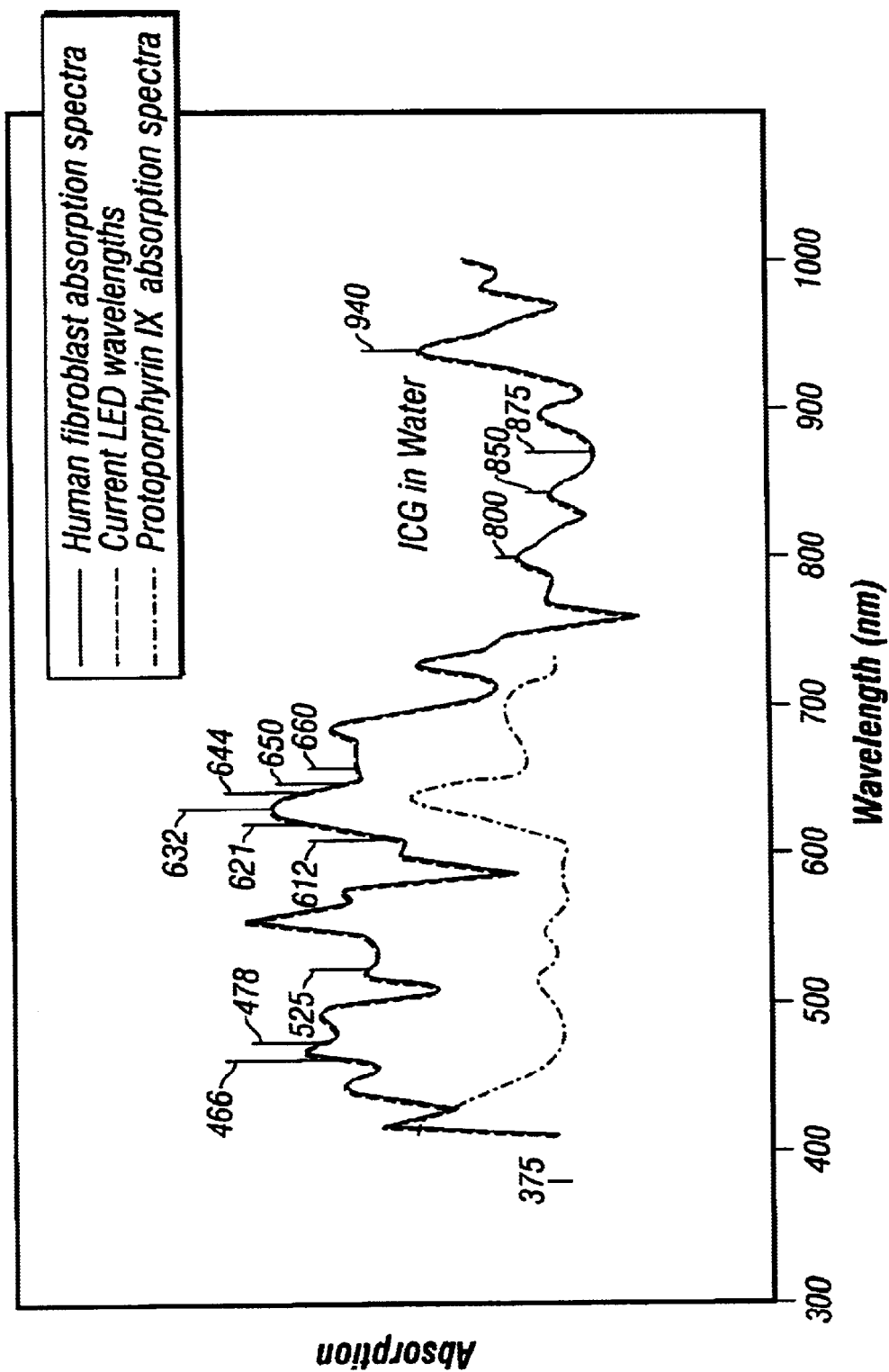
FIG. 4 is a graphical illustration of the absorption spectrum of human fibroblast overlayed with the wavelengths used by narrowband, multichromatic LED emitters of the present invention and also the absorption spectrum of protophorphyrin IX, one of the active chromophores in acne bacteria.
Figure 5:
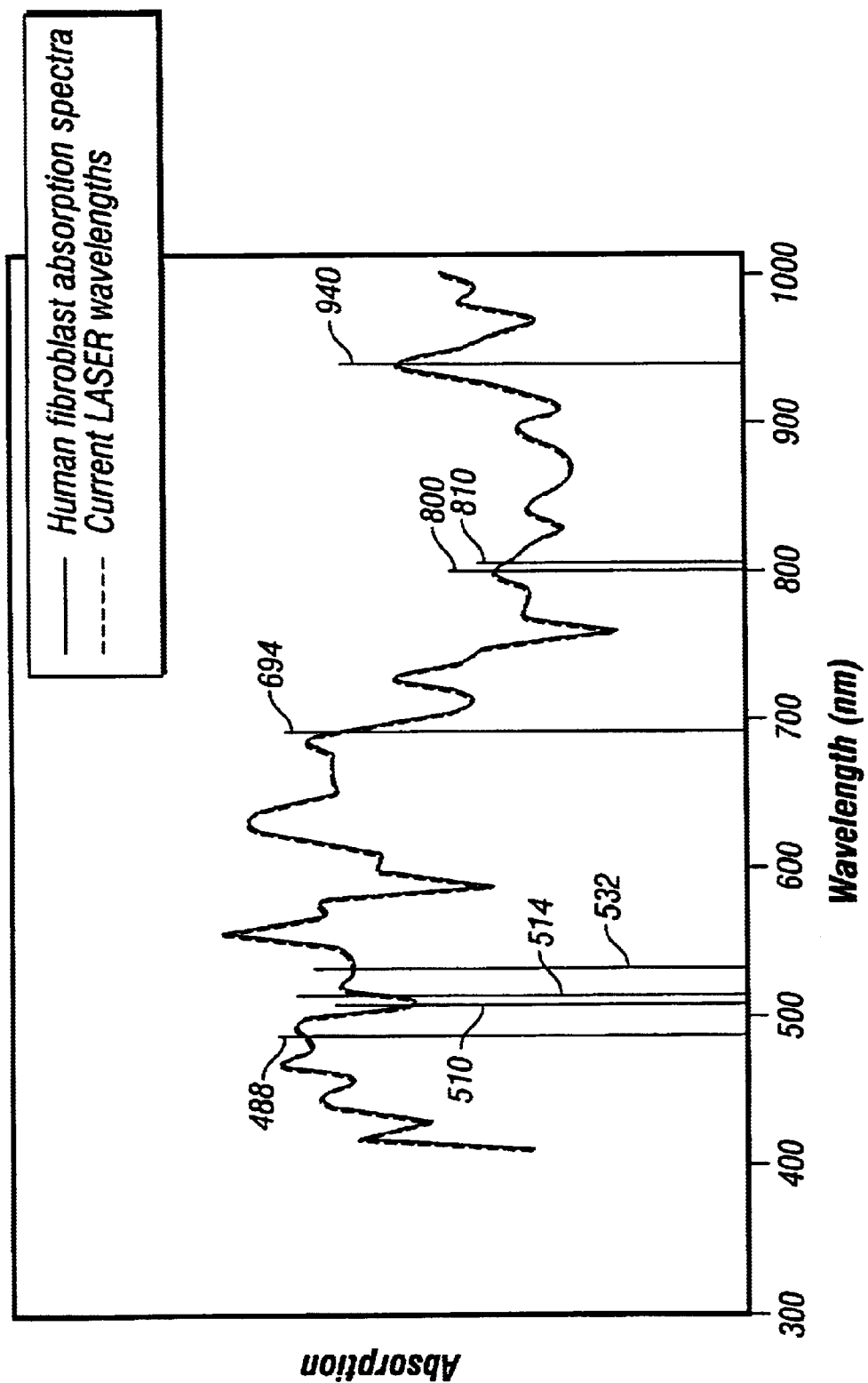
FIG. 5 is a graphical illustration of the absorption spectrum of human fibroblast overlayed with the wavelengths used by Laser emitters.

A detailed description of a preferred embodiment of the present invention will be made with reference to the accompanying drawing figures.

DETAILED DESCRIPTION OF THE INVENTION

The following detailed description is of the best presently contemplated mode of carrying out the invention. This description is not to be taken in a limiting sense, but is made merely for the purpose of illustrating the general principles of the invention. The scope of the invention is best defined by the appended claims.

In one embodiment, the present invention is directed to a process for dermatologic treatment. One such treatment may include the photomodulation of sebaceous oil glands and the surrounding tissue or producing temporary or permanent reduction of activity or destruction of sebaceous oil glands or supporting tissue or the removal, in human or mammalian skin, of some or all of the hairs growing approximate to oil glands. In a preferred embodiment the process produces little or no permanent injury or damage to nearby skin tissue. Substantially only the oil gland and immediately surrounding tissue are affected.

In another embodiment of the invention, topical compositions are used in connection with low-intensity light, produced preferably from light emitting diodes (LEDs), organic light emitting diodes(OLEDs), light emitting polymers, sulfur lamps, xenon arc lamps, metal halide lamps, broad band intense pulsed light sources, filamentous light sources, and lasers filtered to produce an appropriate amount of light energy with a narrowband, multichromatic emissions spectrum, to manipulate the production of collagen in mammalian tissue. The invention may also be used to reduce or destroy bacteria, viruses, prions and other pathogenic organisms infecting in or colonizing living tissue. By this invention, the visibility of wrinkles can be reduced, acne scarring and acne bacteria can be reduced or eliminated, warts can be reduced or eliminated and other beneficial dermatological effects such as increasing blood flow or reducing inflammation or allergic reactions can be achieved.

In a process according to one embodiment of the present invention, an agent may be selected which is capable of penetrating the hair ducts and attaching, bonding or otherwise becoming incorporated into the hair shaft, hair follicle, hair bulb or hair duct cells. Alternatively, the agent can penetrate the epithelial layers of mammalian skin. The agent may be characterized as an active agent. The agent may have sufficient optical absorption of a wavelength (or a combination of wavelengths) of a coherent or non-coherent light source which can penetrate the skin adequately to be absorbed by the target agent or the new agent-tissue complex.

The mammalian tissue, e.g., skin, may be treated to improve permeability of the active agent. This may be accomplished, for example, by treating the skin with steam or a hot moist towel to hydrate the skin and hair or removing a portion of the stratum corneum through various means known in the art, exemplary of which is microdermabrasion. Techniques involving ultrasound have also been successful at improving the penetration of topical compositions into the skin.

The agent may be applied in sufficient quantity and in suitable form to be incorporated into the target tissue in adequate or optimal amounts to allow the production of the desired tissue effect.

Excess agent may be removed, neutralized, inactivated, decolorized, diluted or otherwise altered so that residual contamination of the skin by such excess agent is either (a) absent and does not interact with the light or energy source, or (b) present in such small quantity that it provides no clinical effect.

Delivery of the desired agent into the target tissues, ducts, or glands may be enhanced, facilitated or made possible by the use of enzymes capable of altering the structure, permeability, or other physical characteristics of the stratum corneum or by the use of ultrasound or phonophoresis either for penetration into the gland or surrounding target tissues or, once penetrated, to cause the release of the agent from the encapsulated delivery device such as liposomes, polymers, microspheres, etc. so as to cause penetration or attachment of this active agent. An electrical or magnetic charge may be used to enhance such attachment. Ultrasound may be used therapeutically to interact directly with the agent or the agent-tissue complex to produce the desired damaged target tissues (to be used alone or in combination with laser or non-laser light sources). Microderm abrasion may also be used to permit greater penetration of the skin, wherein the upper epithelial layers are removed. These layers create a natural barrier to the permeability of the skin and. by their removal, penetration of the skin by topical agents is facilitated. This method may be further enhanced by using ultrasound, alone or in combination with alteration of the stratum corneum, to further improve the performance of topical compositions. A more detailed description of several aspects of the use of ultrasound may be found, for example, in the applicant's U.S. Pat. No. 6,030,374 for "Ultrasound Enhancement of Percutaneous Drug Absorption" which is hereby incorporated by reference in its entirety.

Although preferred embodiments of the present invention may use LEDs, ultrasound and/or laser or light energy, as well as electrical stimulation, the present invention is not limited to the use of these energy sources. Other sources of energy, including (without limitation) microwave energy and radio frequency energy may also be used. Exemplary of known light sources are fluorescent lights, sulfur lamps, flashlamps, filamentous lights, etc. One skilled in the art will recognize that any light source capable of emitting electromagnetic radiation at a medically useful wavelength, as described herein, directly, or by means of optical, electronic, or mechanical filtration, is within the scope of suitable light sources according to the present invention. For purposes of the photomodulatory and photothermal treatment methods described, any source capable of emitting light having a wavelength from about 300 nm to about 1600 nm, or producing electromagnetic radiation which is filtered or otherwise altered to exposure the skin, a topical composition, or other component of the present treatment regime to a wavelength of light in the aforementioned range is medically useful.

Particularly useful are neutral density filters for modifying the emission of laser light sources to delivery low-intensity levels of electromagnetic radiation to the target gland or tissue. The term "low-intensity" with regard to light-based therapy of the present invention is defined as the power level where the target tissue is not thermally affected by the electromagnetic radiation. Although the level of light used in accordance with low-intensity light therapy may cause a rise in skin or tissue temperature, the skin or tissue is not thermally injured by low-intensity light therapy of the present invention. Although the number of light pulses, the frequency of the pulses, the interpulse interval, and wavelength of light used will affect the degree of heating of the skin or target tissue, it has been found that light intensities below 1 Joule/cm2 will generally be in the low-intensity regime. For purposes of the present invention, however, low-intensity refers to an energy level (radiation exposure level of the tissue or skin) that does not cause thermal injury to occur. Thermal injury results from exposing the skin or tissue to radiation that causes heating to the point where burning occurs.

Other types of filters, which we will call spectral filters, are useful for diffracting the monochromatic output of a laser to produce an emission spectrum that mimics the output of a light emitting diode. The curves are typified by a bell-shaped emission spectrum centered around a dominant emissive wavelength. Such sources are referred to, herein, as narrowband, multichromatic sources.

Another very useful type of filter is one which block infrared emissions that may be produced by certain light emitting diodes. Such filters, i.e., IR filters, are useful for some forms of treatment where infrared wavelengths are not beneficial, and in some cases detrimental, to effective treatment. The targeted skin or tissue may be exposed to one or more wavelengths of LED, laser or non-laser light such as filtered filamentous or gaseous sources or fluorescent sources or single or multiple frequencies of ultrasound or electrical stimulation. A variety of parameters may be used (including pulse duration, energy, single or multiple pulses, the interval between pulses, the total number of pulses, etc.) to deliver sufficient cumulative energy or appropriate parameter combination to interact with the agent or tissue or cellular component or complex. One one embodiment of the invention, this results in the inhibition or destruction of the sebaceous oil gland or the supporting skin tissue through photomodulatory means, photothermal means, or combinations thereof. Alternatively, proper exposure to certain wavelengths of light, combinations of certain wavelengths of light, such light sources either alone in combination at various intensity levels, with and without topical compositions to enhance the penetration of the light, are capable of photostimulation of hair follicles, glandular and duct activity, etc. resulting in the stimulation of hair growth. Other combinations of light parameters, such as from LEDs, may be used to increase locally in the skin blood flow thus further enhancing or stimulating hair growth. Adjuntive electromagnetic radiation that is non light source such as electrical stimulation or low intensity radio waves may also be utilized alone or in conjunction with the low intensity light therapy. Ultrasound may also be used to selectively preheat the target structures or the entire skin as well as to enhance delivery of selected topical agents or light activated chromophores and also may be used to increase blood flow in the skin or tissue. Further for treatment over a broad area of human skin, the light source may be diffused through a device such as a holographic diffuser; or, alternatively, the light source may be comprised of an array of individual emitters such as the three-panel array of LEDs. For localized treatment, smaller arrays or individual LEDs, such as in the hand held devices may be used. Since LED sources are considered "insignificant risk devices", no medical supervision is required and these devices may be used by the patient for at-home treatment or as part of an ongoing skin-care system after receiving treatment by a physician.

The topical agent may be incorporated into the target tissue by a variety of mechanisms. These mechanisms include, but are not limited to: 1) physical incorporation into the gland (can be oil glands, sweat glands, etc) or target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation, the following compositions and derivatives and analogs thereof: hair dyes, vegetable dyes, food coloring, fabric dyes, tissue stains, shoe or leather dyes, other plant products (such as flavonols, chlorophyll, copper chlorophyllin, bacteria chlorophylls, carotenoids, lycopene, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to sebocytes in the sebaceous gland or duct cells directly, whether by topical or systemic agents that localize in these target tissues, including antibodies or antibody-chromophore compounds of these structures. In general, the topical agent chosen will have certain absorption characterstics that augment the penetration of the radiation to the tissue targeted for treatment, i.e., sebaceous oil gland, acne-scarred tissue, etc.

Most preferable are topical compositions that include a quantity of a naturally occuring chromophore such as chlorophyll, chlorophyllin, protoporphyin, bacteriochlorophyll, etc. These compositions are characterized by a metal-ligand bond. Further, the metal-ligand bond physical structure is common to the naturally occuring native chromophores of the present invention, as well as the cyclic tetrapyrrole ring that chlorophyll shares with suitable cytochromes. In contrast, synthetic chromphores do not include a metal-ligand bond, nor do they exhibit the same general physical structure as naturally occuring chromophores, as is illustrated by the known structures of methylene blue, indocyanin green, and Rose Bengal Dye.

Agents may be delivered in pure form, in solution, in suspension, in emulsions, in liposomes, in synthetic or natural microspheres, microsponges or other known microencapsulation or non encapsulation vehicles, alone or in combination. This list of the forms of the agents is illustrative and not exhaustive. Those skilled in the art will recognize that there are a wide variety of forms for the delivery of topical compositions suitable for use in accordance with this invention.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent. In other situations, continued application to replenish depleted chromophore may be desirable.

One preferred embodiment uses the transdermal application of chlorophyll or its derivatives or other related plant or dye light absorbing chromophores such as phycobilins, indocyanin green dye, etc to the sebaceous oil gland and surrounding tissue. The chlorophyll is then exposed to a source of electromagnetic radiation such as from a laser, an LED, a flash-lamp, or other source filtered to provide a dominant wavelength of from about 400 to about 450 nm. Other preferred wavelengths include from about 360 nm to about 440 nm and, with greater preference, from about 380 nm to about 420 nm. Pulse durations are chosen to yield a sufficient energy fluence (i.e., pulse duration times the number of pulses) to allow the target tissue to be appropriately inhibited to reduce acne bacteria content and to reduce or destroy gland activity through photomodulation and/or photothermal means. While blue light is used for illustrative purposes, it has been found that red light, yellow light, and combinations thereof are also effective in accordance with the present invention. Generally, one skilled in the art will recognize to choose a light wavelength for treatment in the range of about 300 nm to about 1600 nm based on the absorption spectrum of the chromophore or other light-activated topical composition used.

Figure 6:
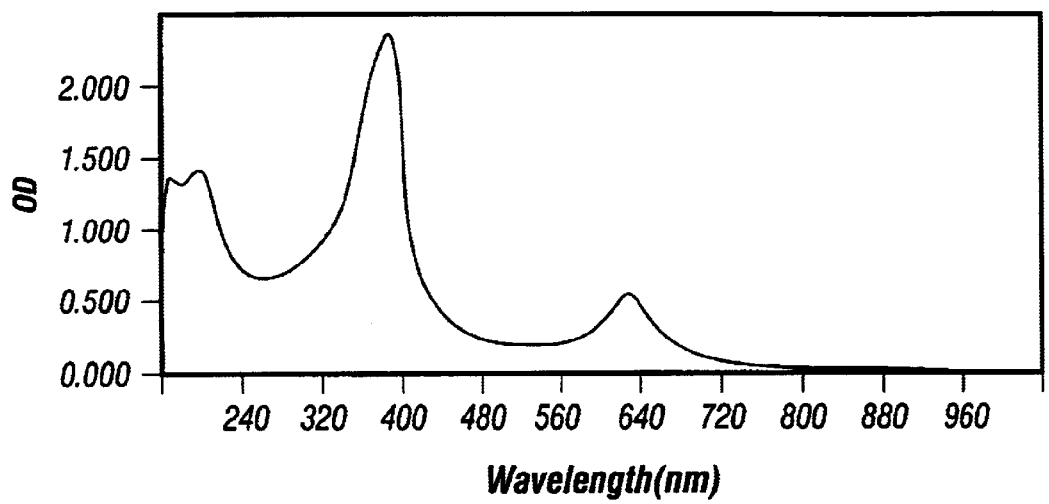
FIG. 6 shows the absorption spectrum for a 0.03% solution of Na Cu Chlorophyllin solution in deionized water.
Figure 7:
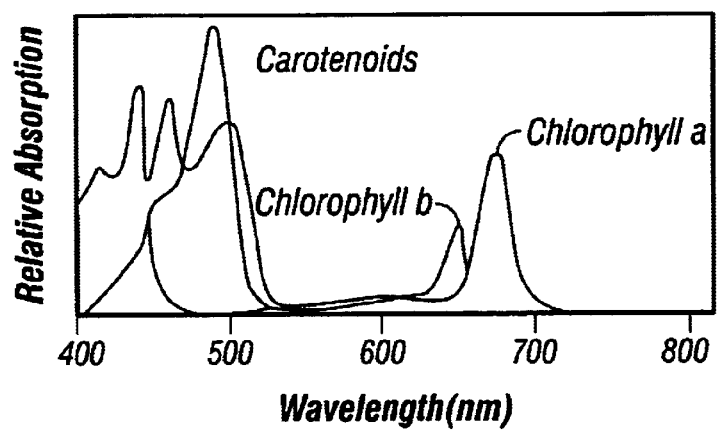
FIG. 7 shows the relative absorption spectra for various naturally occuring chromophores.
Figure 8:
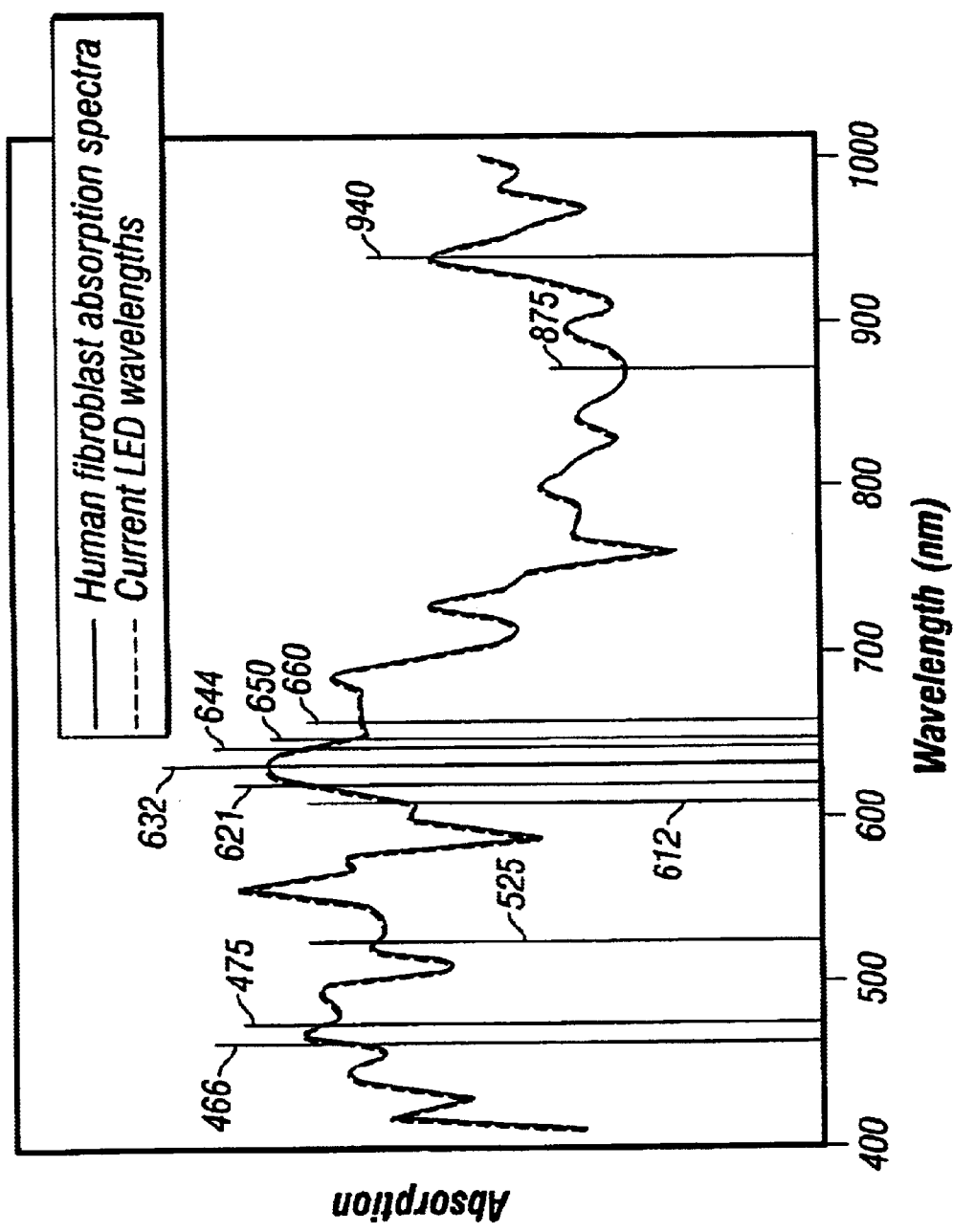
FIG. 8 is a graphical illustration of the absorption spectrum of human fibroblast overlayed with the wavelengths used by LED emitters.
Figure 9:
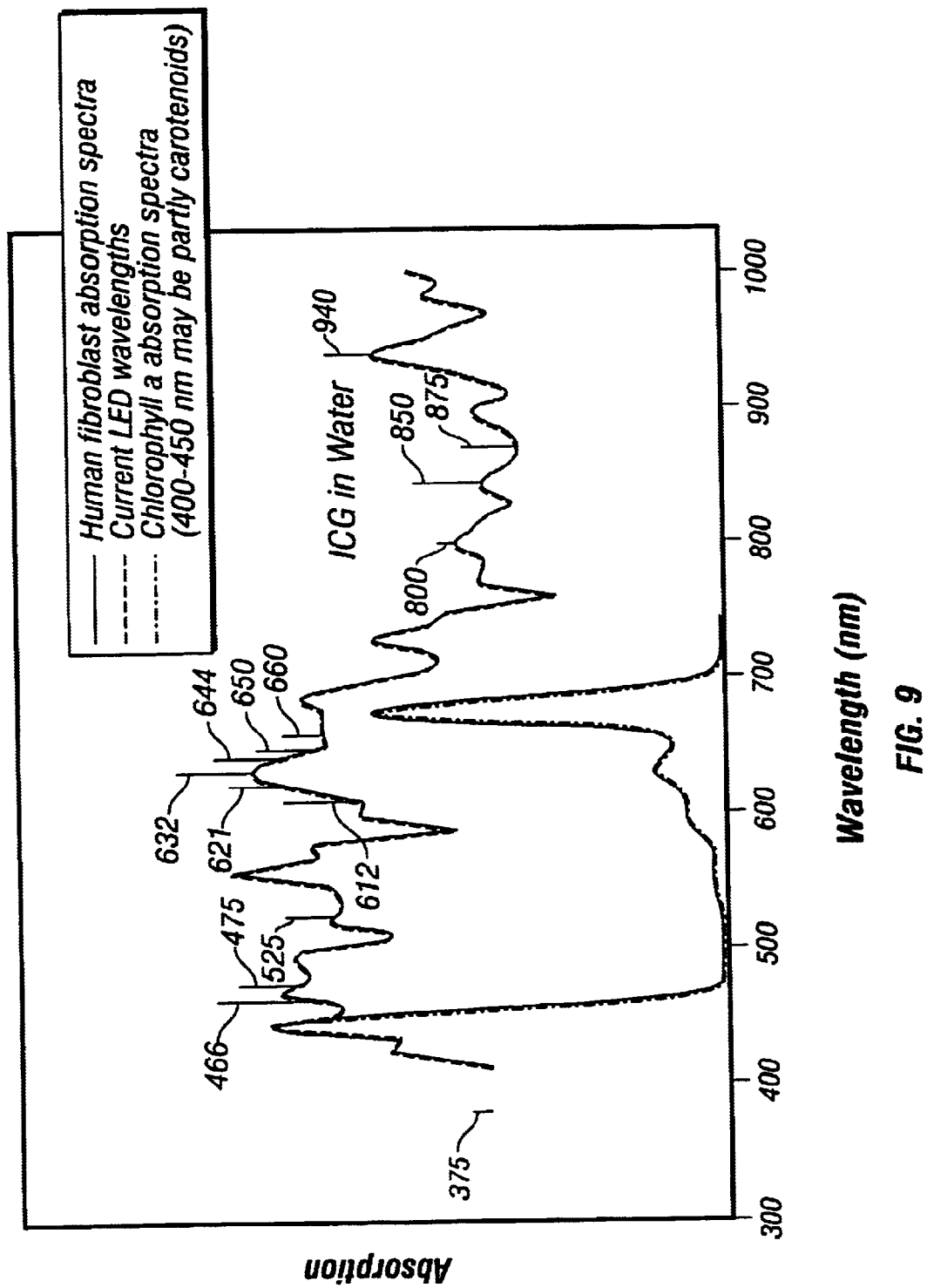
Figure 10:
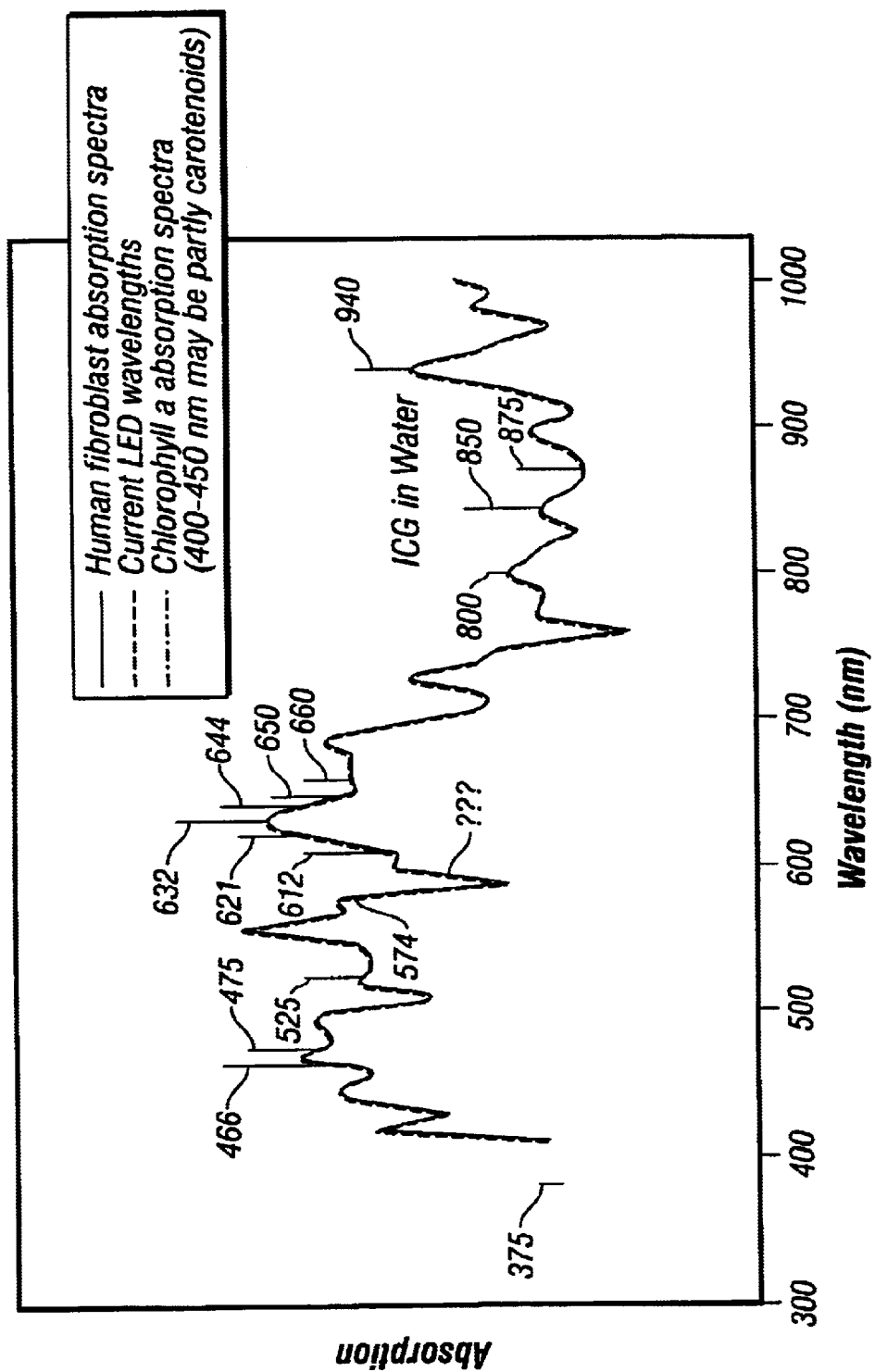
FIG. 10 shows the absorption spectrum for human fibroblast overlayed with lines indicating the dominant emissive wavelength of some commercially available LEDs and also the absorption spectrum for chlorophyll b.
Figure 11:
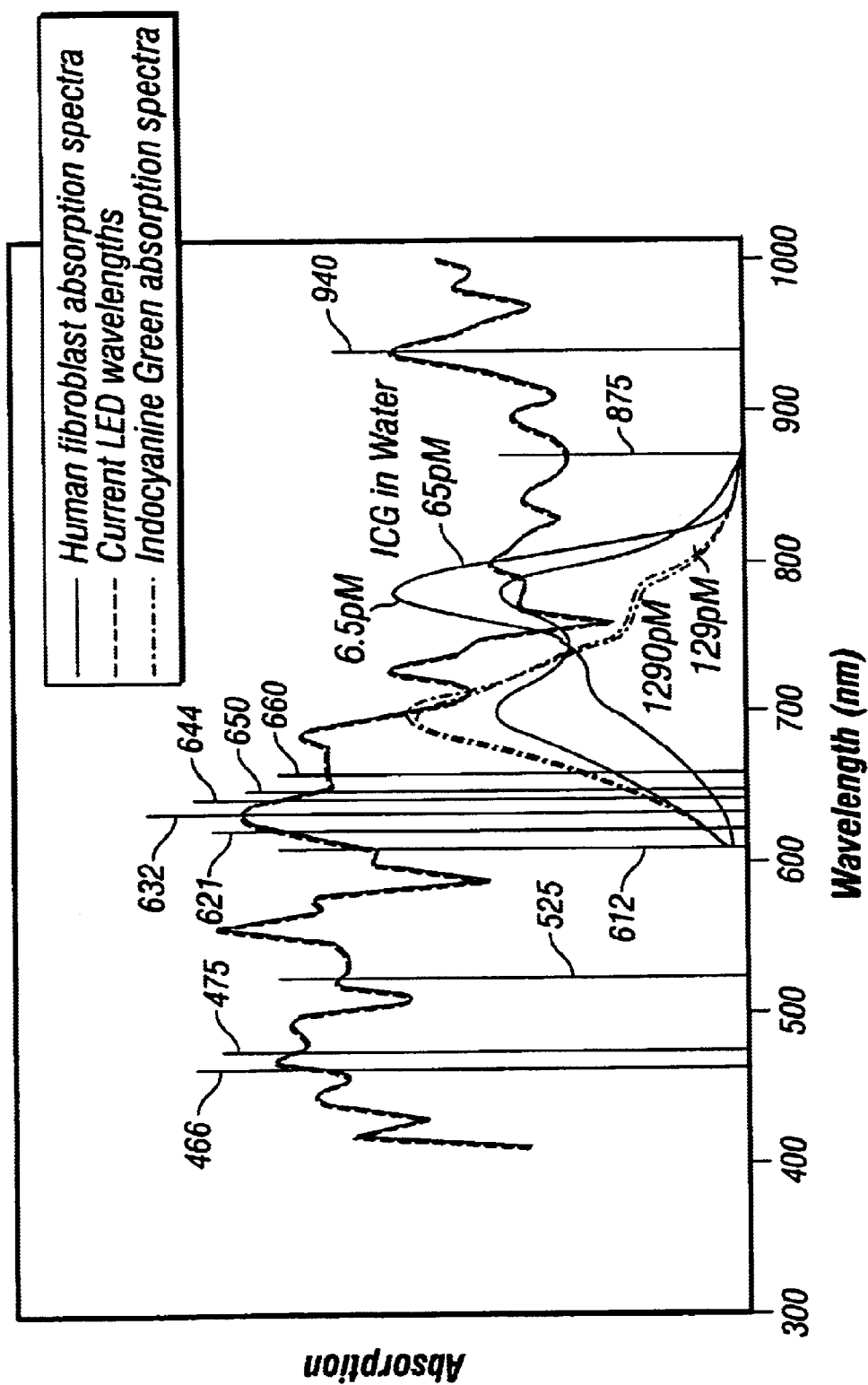
FIG. 11 shows the absorption spectrum for human fibroblast overlayed with lines indicating the dominant emissive wavelength of some commercially available LEDs and also the absorption spectrum for Indocyanine Green.
Figure 12:
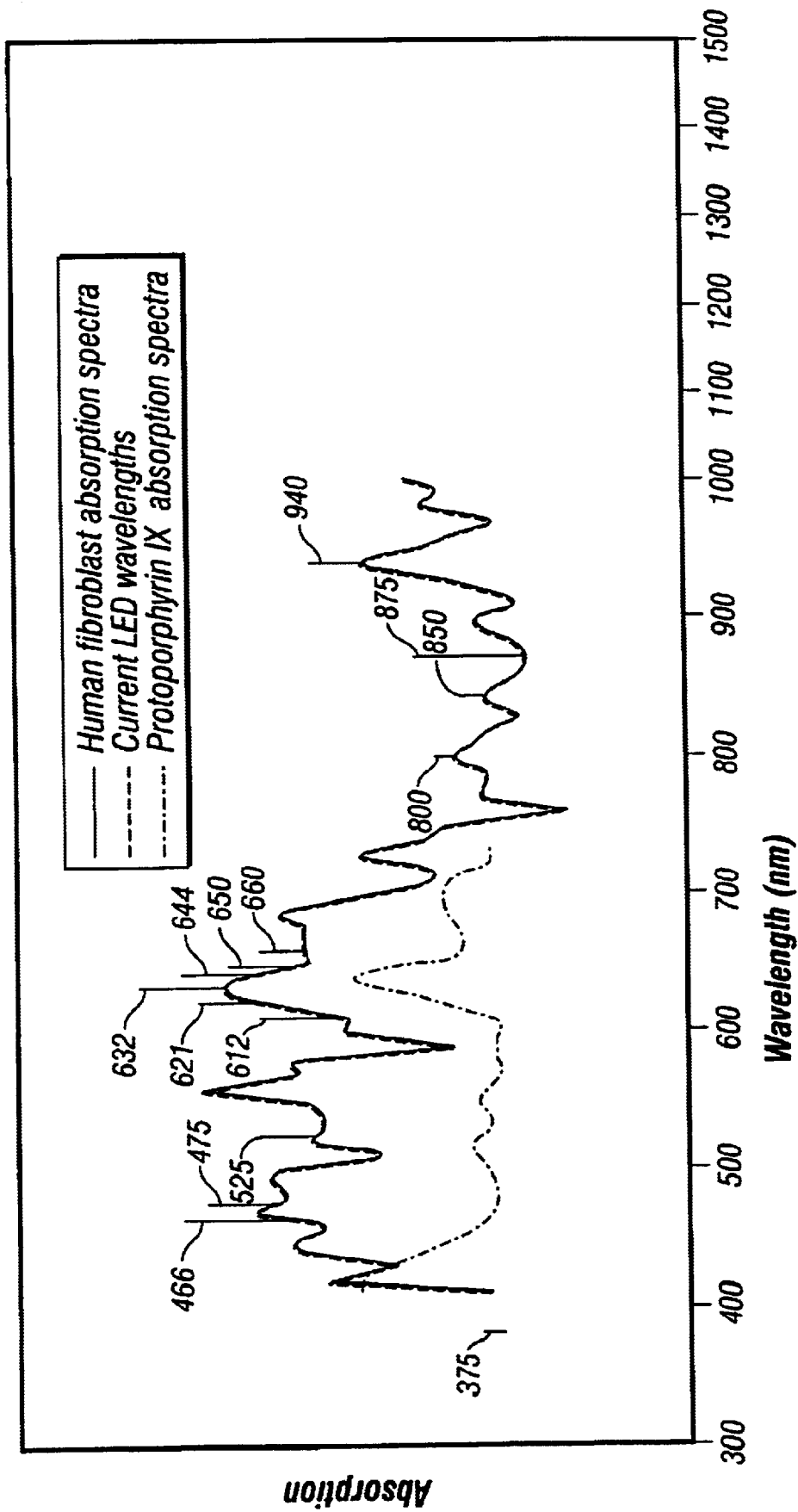
FIG. 12 shows the absorption spectrum for human fibroblast overlayed with lines indicating the dominant emissive wavelength of some commercially available LEDs and also the absorption spectrum for protoporphyrin IX.

FIG. 6 shows the absoption spectrum for 0.03% Na Cu Chlorophyllin in deionized water. The primary absorption peak is shown to be at around 400 nm. This would indicate that for this chromophore, the most suitable wavelength for photomodulator and/or photothermal treatment would be at around 400 nm. Another absorption peak occurs at around 620 nm, thus in an instance where a light source with a dominant wavelength of around 400 nm was not available, a light source with a dominant wavelength of around 620 nm could be used. This figure further illustrates the absorption spectra of a carotenoid with a broad absorption band from 400 nm to 520 nm. This allows use of more wavelengths including those of green light (500 nm to 520 nm). Carotenoids can also be used in combination with chlorophyll compounds for oxidation/reduction purposes. A comparison of the absorption spectra of various naturally occuring chromophores is shown in FIG. 7.

One acne treatment process uses a solution of graphite in a carrier solution and a Q-switched 1064 nm ND:YAG laser. The solution may be applied to the skin which is then treated with the laser using known parameters. It may be preferable to use a high repetition rate and move the laser handpiece slowly enough that pulses are "stacked" in one spot for several pulses before the handpiece is moved to an adjacent spot. It has been found that there is a stair-step like effect of incremental temperature rise in the sebaceous glands with the second and third pulses versus a single pulse. A faster repetition rate also tends to help build the heat up faster, and to higher levels. This tends to produce the maximum heat (which is desirable, as long as the heat stays confined to the sebaceous glands and the immediately adjacent supporting tissues). Since this effect occurs substantially simultaneously with other destructive effects of the process, the damage to sebaceous glands tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate than with carbon solutions and short pulsed Q-Switched lasers. Safety remains at about the same level, since dye related damage tends to be confined to target tissues. There is no appreciable change in patient treatment time.

A preferred method of reducing the visibility of acne scarring is to use a combination of red, blue, and yellow LEDs in a hand-held device. The illumination pattern for the combination of lights is determined by evaluating the absorption spectrum for fibroblast in the patient's skin and optimizing the intensity of light emitted by each LED to closely match the LED emission spectrum with the absorption spectrum of the patient's skin. Depending on the age of the patient, the overall energy fluence is chosen, as is the pulse duration, interpulse interval, and number of repetitions (i.e., how many pulses to use.)

Another embodiment uses a tissue dye which attaches to, or is incorporated into, a target cell and surrounding tissues. The target tissue may be illuminated with a multi-wavelength non-laser light source using appropriate parameters to achieve the desired tissue damage goal.

Another embodiment uses a light source which is well-absorbed by the melanin naturally present in skin and undyed darker hairs. Natural or synthetic melanin or derivatives thereof will be well-absorbed by the same wavelength of light (or alternatively two or more wavelengths, one for melanin and one or more for the dye). This melanin agent is delivered into the sebaceous gland, duct, or supporting tissue, resulting in an enhanced or greater injury to the target tissue (or permitting lower treatment energy parameters, resulting in safer treatment than if the sebaceous gland, duct, or supporting tissue were treated without the melanin dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the light-activated chromophore, native porphyrin containing acne bacteria porphyrin compound, or native sebaceous gland, duct, or supporting tissue pigment and also by the melanin or dye used. A pulse duration on the order of between about one and thirty seconds appears to be preferable. This also tends to be a much longer time than is used in most systems in use today.

Another embodiment uses an agent which facilitates cavitation shock waves or a thermal effect or both. This preferentially damages (or stimulates) the target tissues while minimizing damage (or other adverse effects) on surrounding non-target tissues. This may be used with very short pulsed lasers or light sources or with ultrasound alone.

In one embodiment, a process in accordance with the present invention may be used to provide short or long-term control, improvement, reduction or elimination of acne or other related skin diseases. An active agent may be physically or chemically or immunologically incorporated into cells of the sebaceous (oil) glands, ducts, or supporting tissue, or into the naturally occurring acne bacteria, porphyrin compounds, naturally occuring light activated chromophores, yeast or similar organisms which feed on the oil in the oil glands (or sweat glands )or exists in the oil or oil glands as otherwise relatively benign inhabitants. Some acne bacteria may not inhabit all sebaceous structures and other strains may not produce native porphyrins to target with light. Other acne bacteria may be located deeper than 400 nm to 420 nm light can adequately penetrate, thus treatment with light alone may be only partially effective in clinical treatment. Improvement in skin disorders may be a direct or indirect result of the application of the agents in this process, as may reduced oiliness of the skin, reduced size or diminished appearance of pores, etc. The present invention is also useful for treating enlarged pores, oily skin, and other disorders where there is no active acne-related disorder. It is also possible to utilize the chromophores (naturally occurring or exogenous) described above as 'heaters' to produce local thermal effects thus providing long term reduction of acne. Near infrared or infrared wavelengths may be particularly useful for such applications.

Other similar disorders such as folliculitis which involve the pilosebaceous (hair/oil gland) unit may also be treated using the present invention. The present invention may also be used to reduce perspiration, sweating, or hyperhidrosis from eccrine (sweat) glands or apocrine glands. A preferred embodiment of the present invention may be used to treat other skin disorders such as, for example, viral warts, psoriasis, precancerous solar keratosis or skin lesions, hyperhidrosis/excessive sweating, aging, wrinkled or sun-damaged skin, and skin ulcers(diabetic, pressure, venous stasis).

Figure 13:
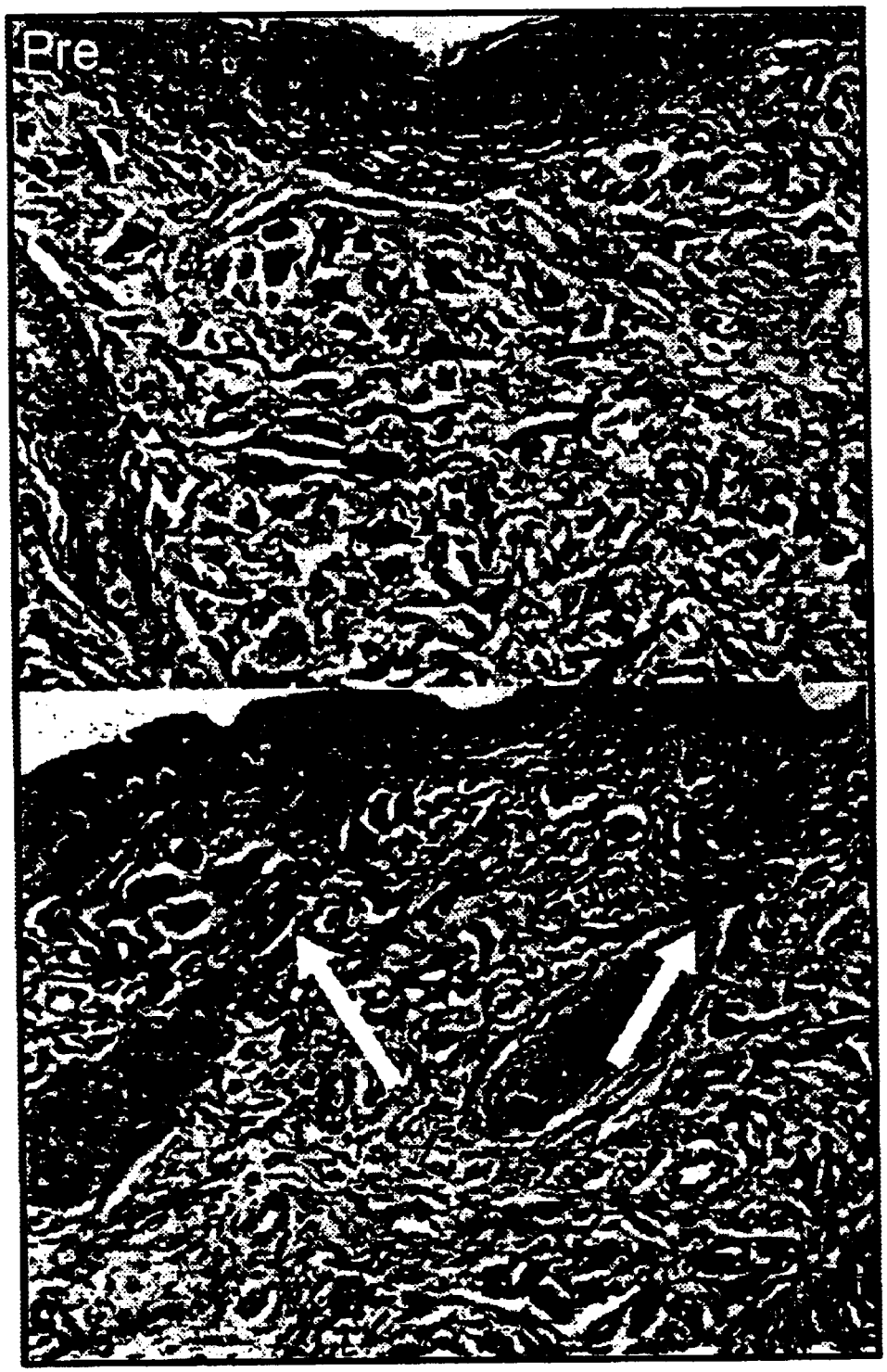
FIG. 13 illustrates before and after pictures of new collagen formation after treatment with 590 LED.

Scarring is commonly seen as a consequence of disorders, diseases, or dysfunctions of the sebaceous apparatus. Scarring may consist of one or more of the following: raised hypertrophic scars or fibrosis, depressed atrophic scars, hyperpigmentation, hyperpigmentary redness or telangectasia. Raised or thick or hard hypertrophic scars (which are composed of an excess of collagen) can be improved by photomodulation wherein the stimulation of production of collagen dissolving enzymes (called Matrix metalloproteinases) such as MMP-1 (collagenase) causes the scar tissue to be diminished. Such photomodulation can be accomplished alone or in combination with photothermal methods (see FIGS. 14–38, wherein MMP-1 can be seen to be increased by the traditional photothermal methods—at around 7.0 J/cm2 energy levels, although MMP-1 also can be stimulated in the non thermal photomodulation light energies). FIG. 13 shows enlarged tissue photographs of new collagen growth produced by the present invention.

Photomodulatory, photochemical, or photothermal treatments alone, or in combination with exogenous or endogenous chromophores, or combinations thereof, can be used simultaneously, sequentially, etc., as described herein for the treatment of sebaceous gland disorders, diseases, or dysfunctions. Further, as herein described, the term photomodulation refers to the treatment of living tissue with light along, heat emitted by a light source, or light-activated chemical compositions, or any combination thereof. Falling within the scope of photomodulatory treatments are photothermal treatment, photoactivation, photoinhibition, and photochemical treatment of living tissue and, in particular, sebaceous structures, fibroblast cells, fibroblast-derived cells, and collagen within human skin.

Further, electromagnetic emitters of the present invention can fall into three categories: those which emit light in the visible spectrum and are useful for photoactivation and photoinhibition photomodulatory process; those that emit light in the ultraviolet spectrum and are also useful for photoactivation and photoinhibition photomodulatory process; and those that emit light in the infrared region and permit photomodulation treatment to be carried out through photothermal means, i.e., heat activation of the exogenous chromorphore, living cells or tissue, or both.

A preferred embodiment of the present invention may use various microencapsulation or other processes to randomly, non randomly, or preferentially/selectively deliver active agents. If the diameter of the micro encapsulations is about five microns, then there may be relatively site specific preferential delivery into the sebaceous oil glands or skin surface stratum corneum cells. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. The micro encapsulations may be synthetic or natural. If ultrasound is used to enhance penetration, then the diameters and ultrasound treatment parameters may need to be adjusted according to the applicable principles which allow the estimation of the optimal ultrasound parameters for driving small particles into the skin, skin appendages or skin orifices.

Microencapsulation may be used to improve delivery of known agents such as chlorophyll, carotenoids, methylene blue, indocyanine green, rose bengal and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the sebaceous gland, duct, supporting tissues, oil itself or bacteria, yeasts, or other organisms residing within these tissues.

Indocyanine green dye is presently in medical use, appears to be relatively benign, may be activated by red visible light lasers, or other sources of monochromatic or multichromatic light, (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference. Methylene blue has also been used according to the present invention with good success.

One of the preferred light sources for 800 nm visible light is the 800–810 nm diode laser. These lasers are reliable and relatively inexpensive due to their solid state electronic nature. However, 810 nm LEDs are also available which now produce as much as 250 milliwatts of energy per LED and more powerful LEDs are under development. Thus, it is possible to produce significant energy with non laser light sources that can be compact and even battery powered hand held devices. Likewise, large arrays of LED can be constructed so that entire body areas (such as the face or shoulders) can be rapidly treated all at one time (current 810 diode lasers can treat areas about one half inch in diameter thus treating the entire face treatment for acne currently requires a prolonged treatment period while individual areas of the face are treated in a fashion much as one would lay floor tiles. Inherently, some areas will receive overlapping treatments and other areas will be skipped or missed. A small hand held LED device can also be used to intentionally spot treat small areas such as acne pimples or deeper acne cysts. However the same principle applies for hair removal, wart treatments, hair growth stimulation, tattoo removal (810 nm light can be used to remove a very large variety of tattoo pigments and the current art of using nanosecond pulses can be utilized with LEDs but also a new method can utilize much longer pulse durations than has been appreciated ranging into the millisecond and even seconds of pulse durations for tattoos and hair removal.

The microsponges (although it is understood that other micro encapsulation delivery mechanism or non encapsulated delivery system may be used) containing or otherwise 'transporting' the active agent may selectively attach, or at least have a chemical affinity for, some part of the oil gland. The ICN dye may be conjugated with lipids, which would then have an affinity for the oil glands. Alternatively, the attachment may occur after the active agent is released from the microsponge (or other delivery device), either passively or by attractive or chemical or immunological forces or attractions. In the case of some microencapsulation carrier vehicles, release may occur after disruption of the vehicle integrity itself, possibly by ultrasound or laser or light or other energy source or perhaps a chemical reaction.

In a preferred embodiment the ICN dye may be mixed with lipids, or put into microsponges (a.k.a. microspheres), and then applied to the skin surface, allowed to sit for a time. Excess dye may be removed, and then the area may be treated with laser or non laser light at about 800 nm, between about 0.001 and 1000 millisec pulses and around 0.01 and 100.0 Joules/cm$^2$. Long duration pulses, lasting up to 20 to 30 minutes, may also be used for certain types of treatment.

U.S. Pat. No. 5,817,089 specifies "particles having a major diameter of about 1 micron". It has been discovered, however, that these diameters may not be optimal. A 1993 Pharmaceutical Research journal article by Rolland et al describes an acne treatment wherein a topical acne drug is delivered with less irritation by putting the drug into synthetic polymer microsphere sponges This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices".

In a preferred embodiment for treatment of acne, graphite particles having an average diameter of about one micron may be placed in delivery devices, such as microsponges, having an average diameter of about five microns. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to sweat glands may be improved.

Use of such applications could enable selective delivery of anti-acne agents, or hair dye for laser hair removal, or agents which stimulate hair growth, or other hair treatments, wart treatments, psoriasis and eczema therapies where the encapsulation diameter was used, with or without ultrasound, to preferentially deliver, and ultrasound at different parameters or laser was used to release (not necessarily to activate or interact).

These techniques may be applied to many other agents in addition to ICN dye and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, the sebaceous oil glands, or other structures. Air pressure or other gases or liquids may be used to enhance delivery or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells; (2) the use of ultrasound to drive graphite particles into spaces between the stratum corneum to enhance the effects of a skin peel process (which physically removes a portion of the outer layers of the skin surface); or (3) physically removing the hair by methods such as waxing or pulling and then injecting the treatment composition, i.e., the chromophore or other topical composition, into the sebaceous gland or duct. Such methods are contemplated in one embodiment of the invention.

A known skin peel process may be improved by using ultrasound to open intercellular spaces in the outer stratum corneum layer of the skin via cavitation. Then an active agent may be driven in further with the same or similar ultrasound. Ultrasound may be used before or after the application of peel or microdermabrasion processes. Electrical stimulation can also be used in conjunction with all of these therapies. Fibroblast stimulation may be optimized with both topical agents that are applied afterwards (while the skin is still relatively permeable) and also with additional low level light stimulation.

The processes described above may be used to deliver two different agents, either serially or simultaneously. The two agents may then be activated by the light source together to work synergistically, or to combine and then have an effect, or to deliver two different agents that may be activated simultaneously or very closely in time. Two different light sources or wavelengths may be used serially or simultaneous to have different effects such as treating active acne lesions and also acne scarring; treating acne rosacea lesions and also rosacea blood vessels or telangectasia; or using photothermal means for active acne and nonthermal photomodulation for treating acne scarring or skin wrinkles.

Two entirely different laser, LED, or light beams may be delivered substantially simultaneously through the same optics at different parameters. For example, one beam may be delivered primarily to release or to activate, and a second beam primarily to treat. Additive effects may be achieved by using two beams at the same time, such as the use of blue light with a wavelength of approximately 400 nm and red light with a wavelength of approximately 600 nm. For example, a known process for skin peel and hair reduction may be optimal at 1064 nm for safety and for treating all skin colors, but other wavelengths may be better to achieve a low level laser stimulation of fibroblasts. Acne reduction is achieved by this process, as well, using lasers or LEDS as the low-level light source at a wavelength chosen according to the absorption spectrum of the topical composition used. Particularly preferred for topical compositions are those comprising naturally occurring chlorophyll-containing compounds, carotenoid-containing compounds, phyocobilin compounds, certain dyes such as indocyanine green, methylene blue, rose Bengal and other similar dyes and derivatives thereof, and mixtures thereof, as well as derivatives, analogs, and genetically engineered or chemically or immunologically modified forms of such agents.

The use of immunomodulating active agents in conjunction with photomodulation is another application wherein photomodulation is used to trigger, enhance, activate, accelerate, amplify, stimulate, or inhibit any complementary, synergistic or inhibitory process which is activated by an immunomodulating substance or combination of such substances. In addition to the described effects above, photomodulation with light can produce stimulation or inhibition of local or system immune responses. Furthermore low energy electromagnetic fields can produce similar phenomena and can be used alone or in combination with photomodulation.

Electromagnetic modulation can be produced by low intensity electromagnetic fields in either pulsed or continuous wave fashion with energy densities typically in the range of 10 microT to 100 milliT and can be pulsed in the low or high frequency range, but one preferred embodiment is to use low frequency in the 10–100 Hz frequency range.

The use of low intensity LED light alone or in conjunction with a topical or oral light activated agent and the concomitant use of a topical or oral or systemically delivered immunomodulating agent. Some such treatments would require medical supervision, however by utilizing low intensity LED and selecting very safe active agents home self administered therapy is possible. For example, topical indocyanine green dye or chlorophyll or drugs such as aminolevulenic acid is applied to a skin wart and then treated with an 810 nm LED at the desired parameters. Treatment with a topical immunomodulator such as plant derived active substances such as imiquinod or urushiol (poison ivy active agent) can be used to complement or enhance the reduction or removal of warts. In many cases the wart virus (human or animal papilloma virus) remains in the skin even though the visible wart disappears. Also, some strains of these viruses have now been proven to cause cancer. Thus the use of adjunctive immunomodulators may be beneficial in triggering the natural immune system of the body to 'destroy' the wart virus so that it does not remain 'dormant' and a possible cancer risk. One example is the problem with the association of cervical cancer and the genital wart virus. Several strains have now been shown to be oncogenic and cause cervical cancer—which still kills many women worldwide despite PAP smear screening. There is a growing world wide epidemic of genital warts and treatment is often delayed or unavailable in many areas of the world.

The use of LED and a topical light activated chromophore would provide a simple, low cost and reliable (LED may last up to 100,000 hours and are very resistant to vibration and other environmental damage) means of treating and can be assembled into devices which can be easily inserted intravaginally and which can provide complete and uniform illumination of the affected cervical tissues and is very simple to operate.

A hand-held device containing the low-level light source may be used to photomodulate or photothermally activate, or both, the living tissue or active ingredient in the topical composition, or both, for skin peel, hair reduction, or acne reduction, and either simultaneous or synchronized sequentially in time to deliver another wavelength that may be optimal to in view of the absorption characteristics of the patient's fibroblast spectrum or the spectrum of the topical chromophore composition. In the one case it may be the best wavelength to stimulate fibroblasts. In another case it may allow selection of a melanin or dye (or other agent) having very strong affinity for the sebaceous gland and very strong absorption at the wavelength used for treatment. Similarly the absorption or fluorescent emission spectra of various living cells or subcellular components and light activated chromophores can be analyzed and wavelengths suitable for 'action' or photomodulation may be identified.

There are a wide variety of different operating parameters that may comprise conditions effective to produce beneficial cellular effects such as triggering cellular regeneration or photoactivation or photoinhibition which, for example, could reduce the activity of, or even destroy, oil glands in the skin, thereby indirectly reducing acne bacteria. Also, it is preferable to target a natural chromophore for photoactivation or photoinhibition, each falling under the general term photomodulation is possible for directly treating the naturally occuring porphyrin compounds in acne bacteria, in addition to targeting exogenous chromophores like carotenoids, chlorophyll, phycobilin and derivatives thereof including copper chlorophyllin and other dyes such as indocyanine green dye, methylene blue dye, rose bengal, congo red and similar compositions known to those skilled in the art. Further photothermal modulation of the oil glands and surrounding tissue can be accomplished via the same means as described above, although the operating parameters may vary. The difference being that photothermal treatment uses heat to induce minor to moderate amounts of thermal injury to the gland or surround tissue to reduce the activity of the target tissue or destroy it altogether.

Exogenous chromophores are substances which absorb light or electromagnetic radiation in at least one narrow band of wavelengths and assist with the treatment method and system of the present invention by applying them to an area of the skin to be treated. Selection of the exogenous chromophore is determined by the absorption spectra of the chromophores and is dependent on the wavelength of the narrowband multichromatic emitter used for treatment. In accordance with a preferred embodiment of the invention, the chromophore will aid in treatment by enabling at least the dominant or central wavelength of the narrowband, multichromatic radiation to penetrate at least the stratum corneum layer of the skin and permitting the photomodulation or photothermal injury or destruction of living tissue, sebaceous oil gland, duct, or supporting tissue in and below the stratum corneum. In some instances, the photomodulated tissue can be below all of the epithelial layers of the skin.

Some examples of possible operating parameters may include the wavelengths of the electromagnetic radiation to which the living tissue containing cells to be regenerated, stimulated, inhibited, or destroyed, the duration of pulses (pulse duraction) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Wavelength—Each target cell or subcellular component, or molecular bond therein, tends to have at least one unique and characteristic "action spectrum" at which it exhibits certain electromagnetic or light absorption peaks or maxima, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or the exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters unless they are equipped with one or more filtering devices which allow the transmission of only narrow bands of selected wavelength(s). The laser diodes are also multichromatic with narrow wavelength bands around a dominant band, i.e., they are narrowband multichromatic devices—devices which emit electromagnetic in a narrow band of radiation either symetrically or asymetrically around a dominant wavelength. For purposes of the present invention, any device that emits electromagnetic radiation in a bandwidth of +/− about 100 nanometers around a dominant wavelength can be considered to be a narrowband, multichromatic emitter. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. According to the present invention, however, such lasers can be filtered to produce light intensity levels suitable for use with treatment according to the present invention and, as well, can be filtered to emit a spectrum of light similar to that of LEDs. The use of lasers, according to the prior art, has relied upon the coherent, i.e., monochromatic, nature of their electromagnetic emissions.

According to the present invention, lasers are a suitable light source but are not used for their ability to emit high intensity radiation or for their monochromatic radiation (single wavelength output), as has been done previously. Generally, any source of electromagnetic radiation capable of exposing the target tissue with from about $1 \times 10^{-6}$ J/cm$^2$ to about 10 J/cm$^2$ of energy in the desired wavelength (generally within the range of from about 400 nm to about 1600 nm) will be able to effect modulation of collagen, fibroblast, or fibroblast-derived cells, although 1 J/Cm$^2$, or less, is preferred to avoid thermal injury. Such light sources can be used in either a continuous wave (long pulse) or in a pulsed manner. Lasers are suitable for use in either mode. Since lasers are monochromatic, the laser may be filtered to produce a narrowband, multichromatic spectrum. In the prior art, lasers were used to produce thermal injury to the skin or target tissue because of their ability to produce high energy fluences. According to the present invention, however, lasers are acceptable because of their wide availability, the assortment of primary wavelengths that commercially available models produce, and their ability to produce a wide range of energy fluences (although with some commercial lasers, production of low energy fluences may require filtration of the laser's output).

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method. It is also important to penetrate any interfering chromophore that also absorbs at this same wavelength (e.g. dark ethnic skin, plastic Petrie dishes for tissue or cell culture, etc.). It is important to penetrate any tissues or organs in its pathway.

For example, light having a dominant wavelength emission in the range of about 400 nm to about 420 nm has such a short wavelength that not all sebaceous glands or acne cysts can be effectively treated due to the limited depth of penetration of the radiation, whereas light having a wavelength of about 600 nm to about 660 nm can more easily penetrate to a greater depth, if treatment of the lower dermal layers or even deeper is desirable. Accordingly, the selection of the dominant wavelength of the radiation emitter is also dependent on the depth of treatment desired. For example indocyanine green dye absorbs around 800 nm and chlorophyll compounds absorb at longer and shorter wavelengths, thus the longer wavelengths such as these will penetrate better than the 420 nm wavelength of protoporphyrin IX. The selection of the proper wavelength is one of the significant parameters for effective use of the present invention, but others are important as well:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation. Energy fluence, while not synonymous with energy density, is related in that it represents the total amount of energy received at the target skin or tissue and is a product of the energy density, number of pulses, and pulse duration.

Pulse duration—The exposure time for the irradiation is very critical and varies with the desired effect and the target cell, subcellular component, exogenous chromophore tissue or organ.(e.g. 0.5 femtoseconds to 10 min may be effective for human fibroblasts, though greater or lesser may also be used successfully). In a preferred embodiment of the invention for the manipulation of collagen production in human skin, extremely short pulses used in conjunction with carefully selected interpulse intervals (time between pulses) have been found to be beneficial. For such treatment, pulse lengths can vary from less than one picosecond to several seconds with interpulse intervals of a few picoseconds to a few hundred milliseconds.

Figure 14:
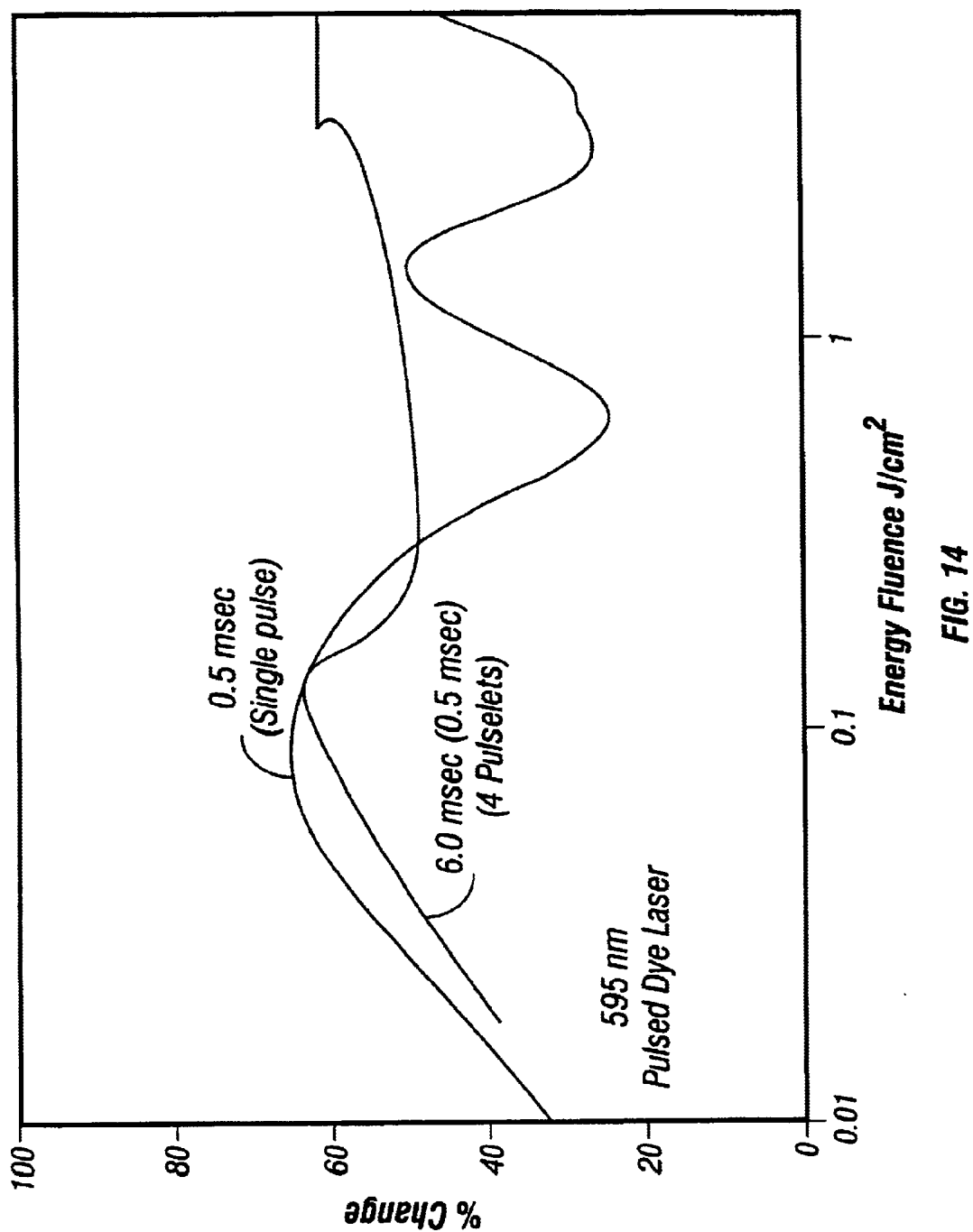
FIG. 14 shows the percent change of collagen relative to energy fluence when varying pulse length and interpulse delay (off time).
Figure 15:
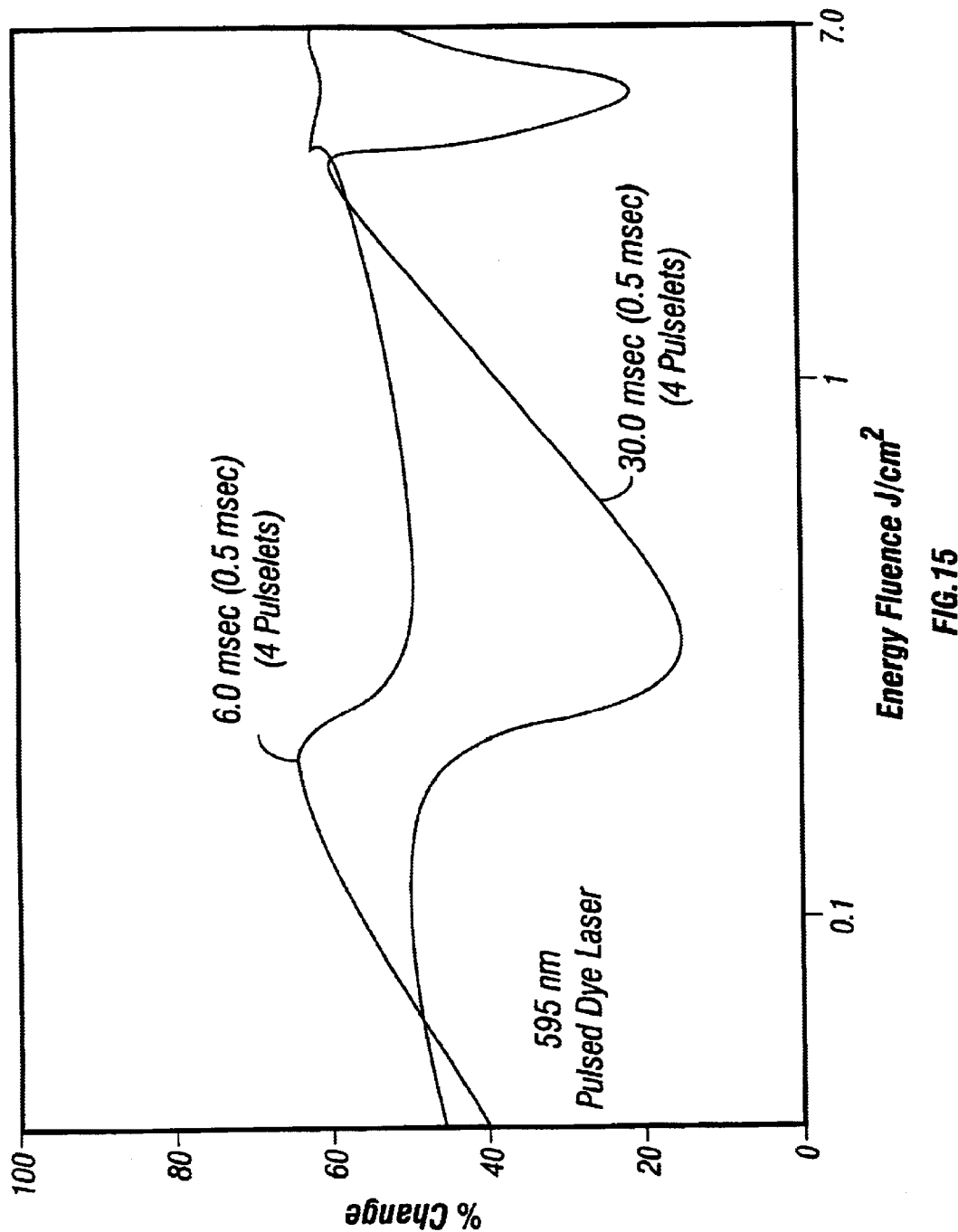
FIG. 15 shows the percent change of collagen relative to energy fluence when varying interpulse delay (off time).
Figure 16:
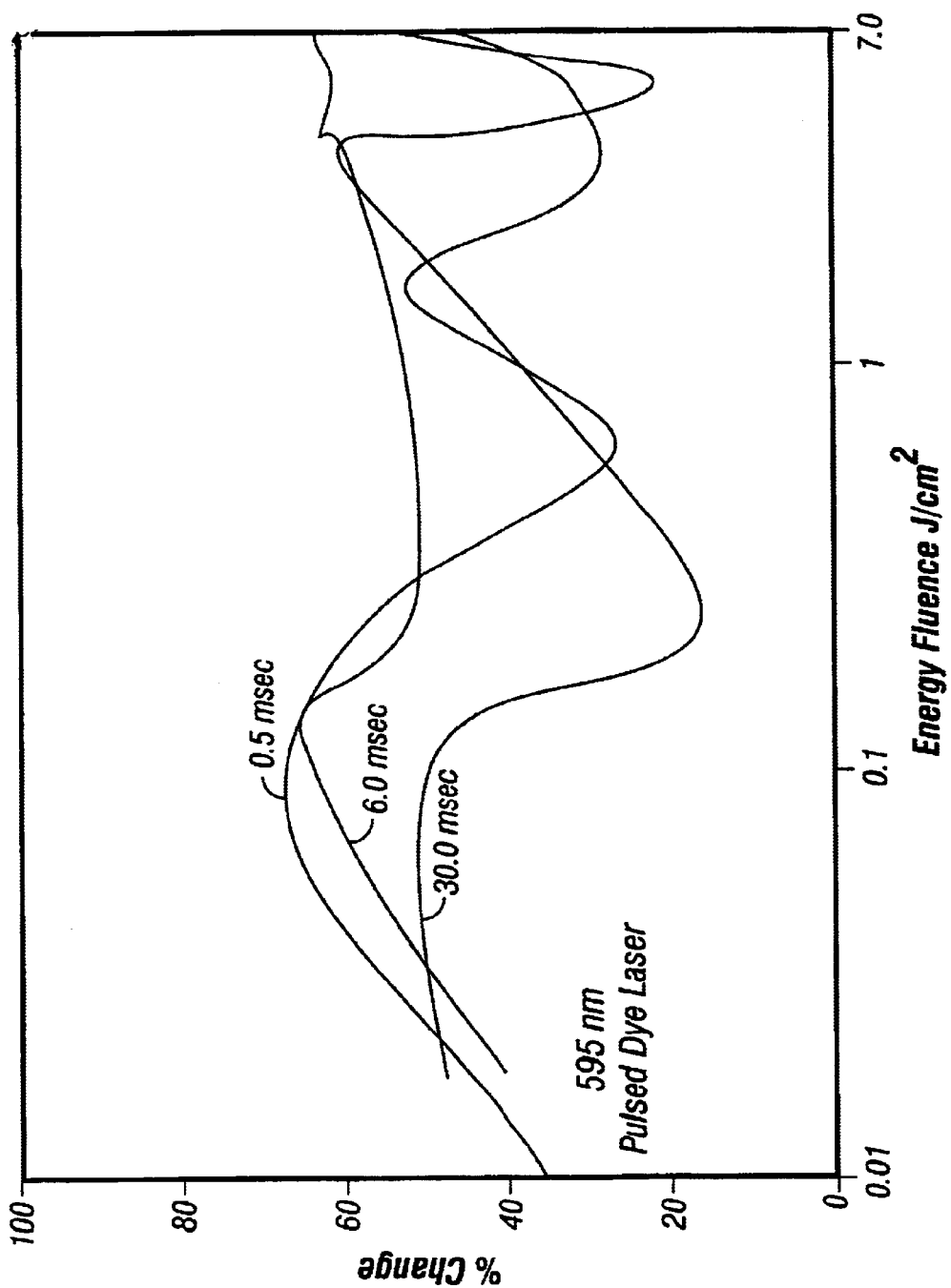
FIG. 16 shows the percent change of collagen relative to energy fluence for treatment with 590 LED on a tissue sample obtained from 42 year old test subject.
Figure 17:
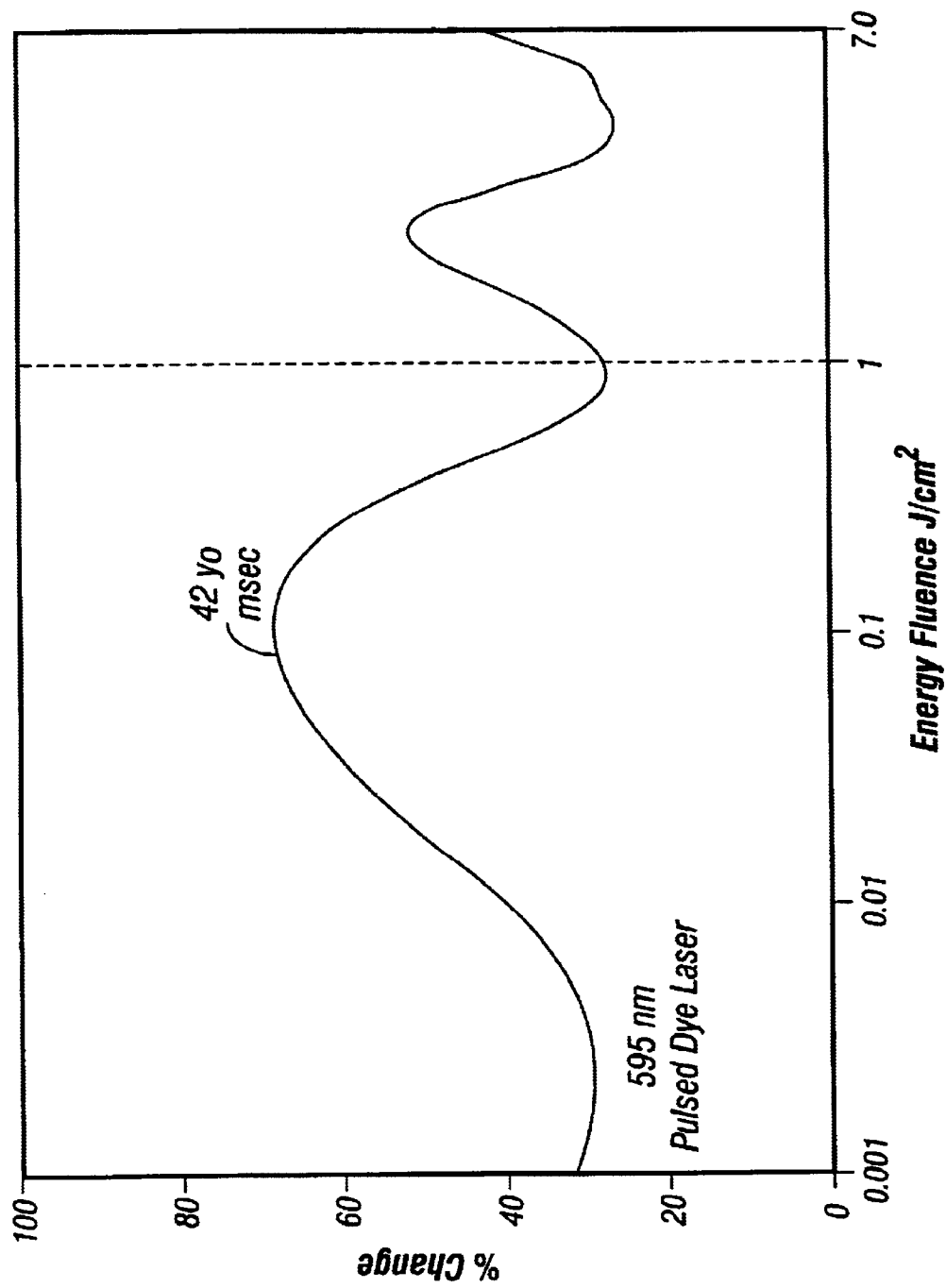
FIG. 17 shows the percent change of collagen relative to energy fluence in a tissue sample from a 42 year old test subject, using a 0.5 msec pulse length.

To maximize collagen production while minimizing the production of collagen-dissolving enzymes, however, pulse durations of from about 1 femtosecond to about minutes 100 milliseconds are preferred, depending on the target 'reaction center' or 'receptor' of the photomodulation there are preferred ranges for stimulation which are distinct from those for inhibition and also there are broad ranges where minimal effects are produced; also we have demonstrated that by varying one or more of the photomodulation parameters; and interpulse intervals of from about 1 millisecond to about 1 second are preferred. FIG. 14 illustrates the relationship between energy fluence and percent change in collagen production (a higher percent change indicates more collagen production).

For example, with human fibroblasts 590 nm LED light stimulated procollagen I production maximally in the following distinct energy density ranges: 1.5–3.5 J/cm2; 100–500 milliJ/cm2; 100–1000 nanoJoules/cm2. Pulse duration combinations for these cells have also been noted which are more or less effective at photomodulation/ stimulation. A regime of 250 msec on followed by 100 msec off and repeated for 100 pulses is very effective at stimulation of procollagen I, whereas 250 msec on and 1000 msec off for 100 pulses is almost completely ineffective (the only difference being the 'off time' although the total energy exposure is identical. Thus, the interval between pulses can greatly affect the results.

Similar significant effects can be demonstrated by varying the number of pulses (also referred to as repetitions). For example, in many cases large numbers of pulses is less effective at stimulation than a much smaller numbers of pulses; and continuous exposure may be more effective than pulsed light with the same total energy fluence depending on the choice of pulsed parameters. Although millisecond pulses are one of the preferred embodiments, the use of continous wave light is another preferred embodiment and also the use of very short pulses in the pico, femto and nanosecond ranges are also a preferred embodiment for photo modulation with both LED and with certain pulsed lasers such as Q switched lasers.

It has been found that pulses ranging from 1 femtosecond to 20 nanoseconds with an interpulse delay of about 20 to 100 milliseconds is a particularly effective operating regime for stimulating collagen production while minimizing the production of collagen dissolving enzymes such as mmp-1. A very important factor is the interpulse delay (time between pulses) which, although not wishing to be bound by theory, appear to govern the relaxation time of the 'reaction centers' in the affected cells. These reaction centers are, inter alia, molecular structures, chemical bonds, cell or subcellular receptor sites or conformational changes in the shape of various structures (typically cell or subcellular membranes) and act as 'antennae' to 'receive' or 'capture' the light energy or photons generated by photomodulation or from electromagnetic fields. As shown in FIGS. 18–31, the percent change in procollagen I production is maximized in one of the preferred embodiments with an interpulse delay of 100 milliseconds.

Figure 18:
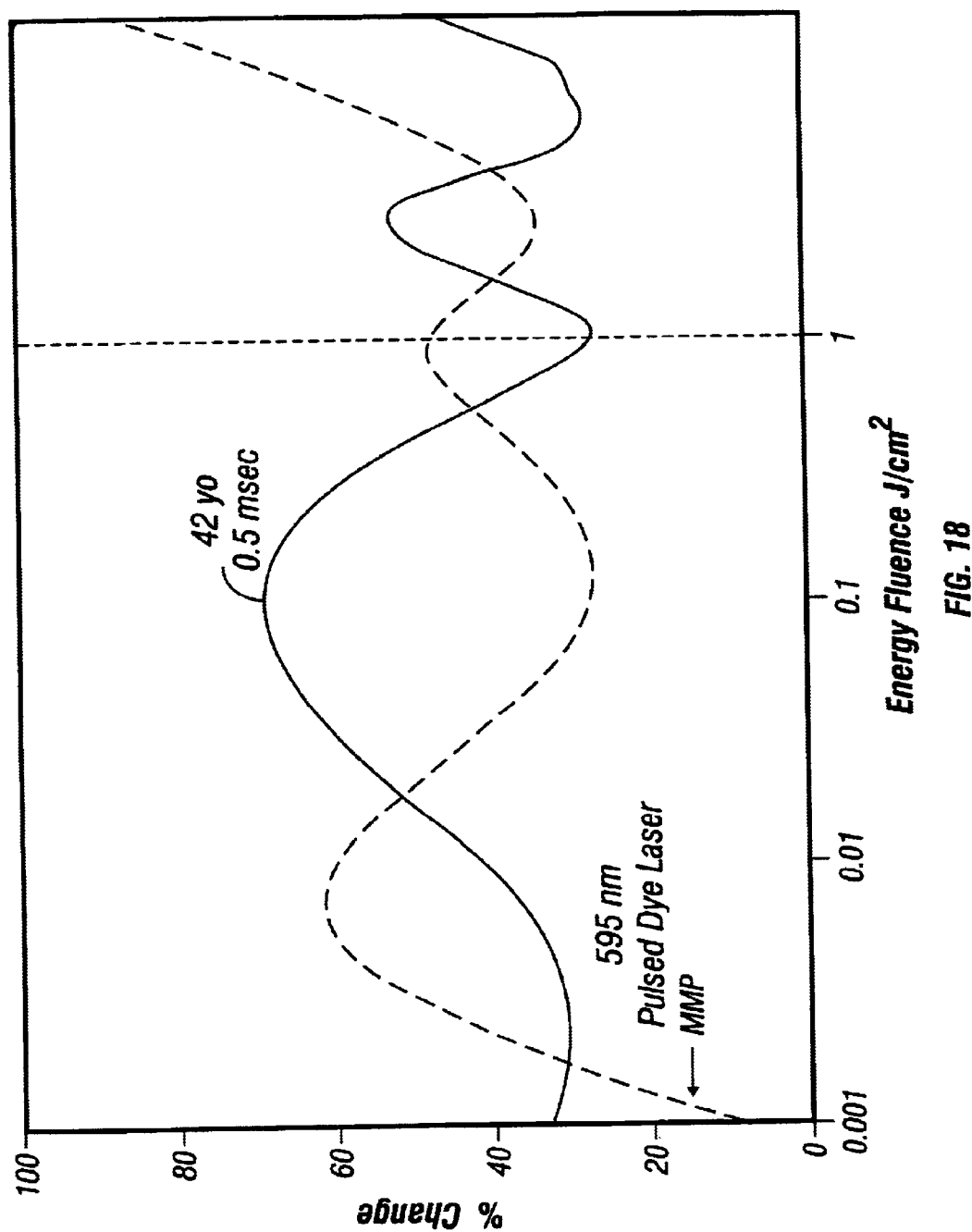
FIG. 18 shows the percent change of collagen and MMP relative to energy fluence in a tissue sample from a 42 year old test subject, using a 0.5 msec pulse length.
Figure 19:
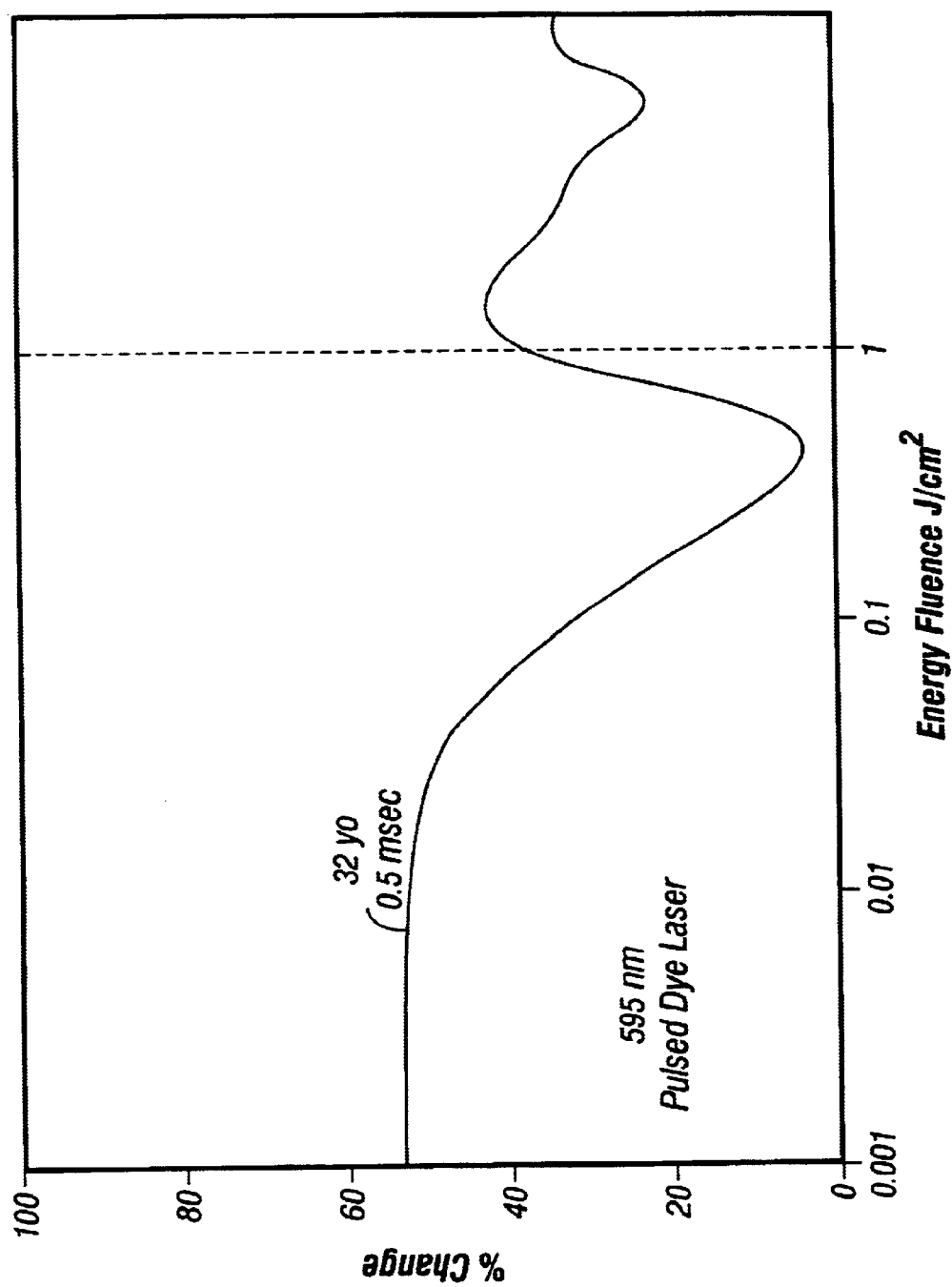
FIG. 19 shows the percent change of collagen relative to energy fluence in a tissue sample from a 32 year old test subject, using a 0.5 msec pulse length.
Figure 20:
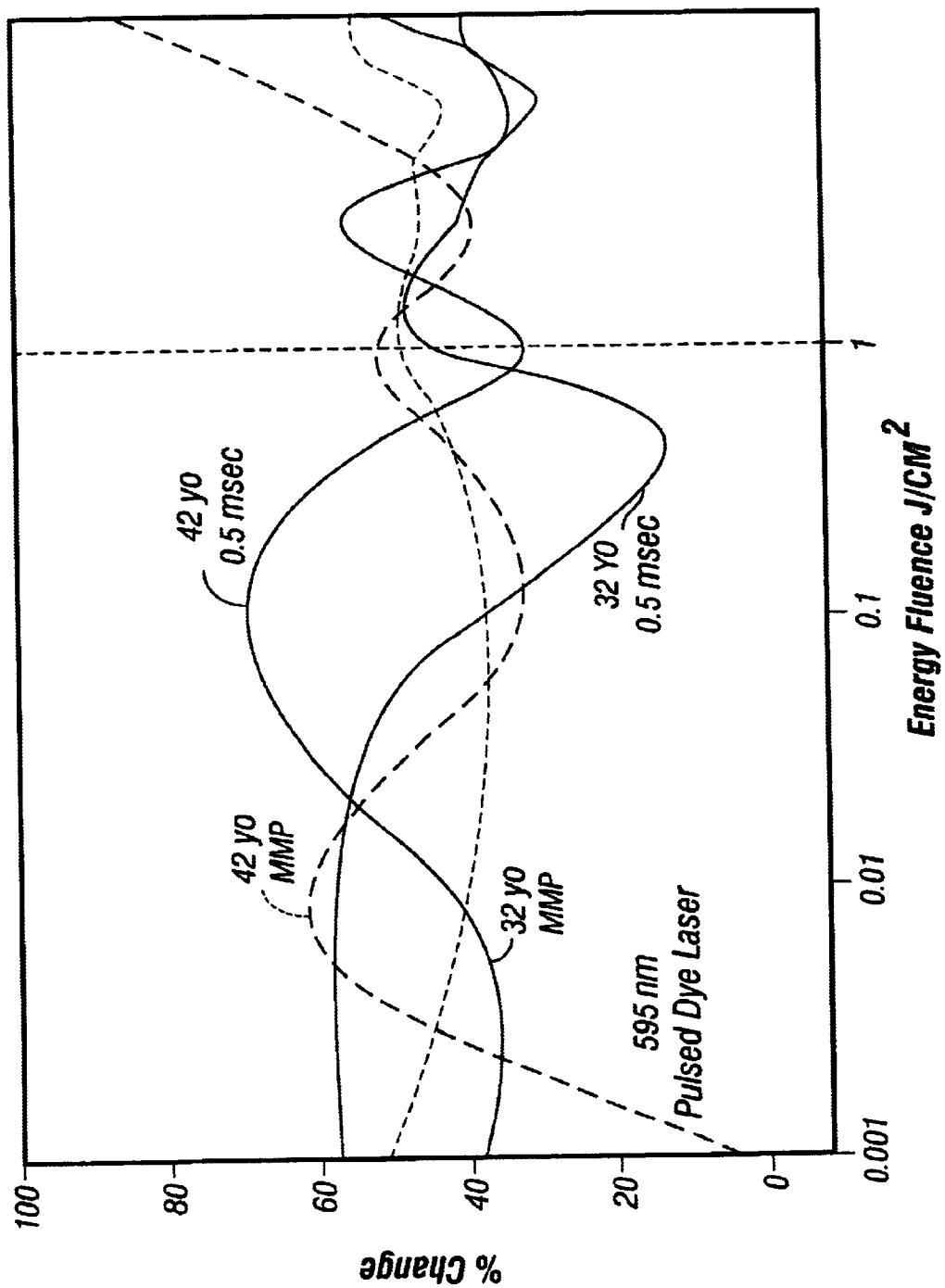
FIG. 20 shows the percent change of collagen and MMP relative to energy fluence in a tissue sample from test subjects of varying age, using a 0.5 msec pulse length.
Figure 21:
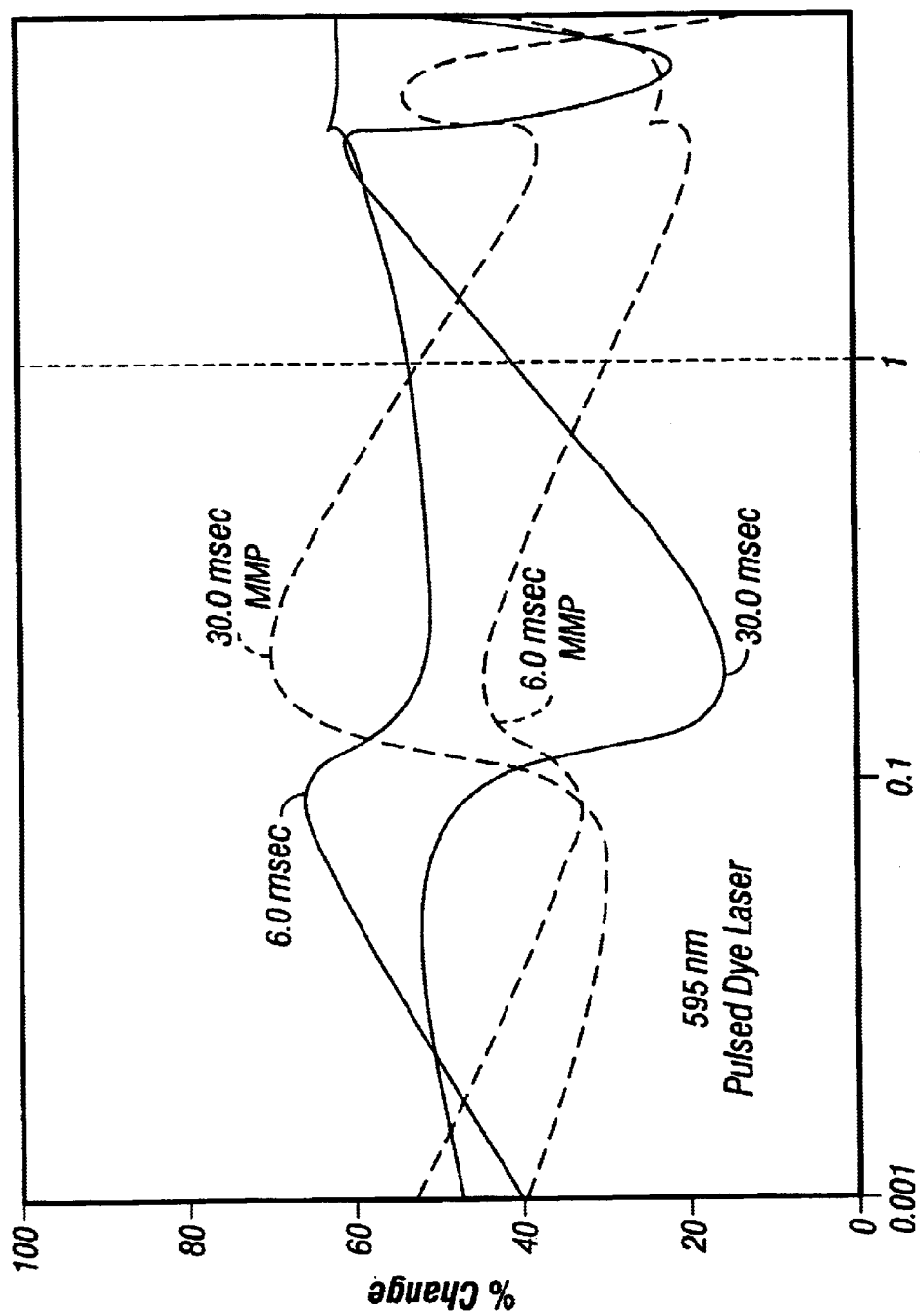
FIG. 21 shows the percent change of collagen and MMP relative to energy fluence for pulse lengths of 30.0 msec and 6.0 msec.
Figure 22:
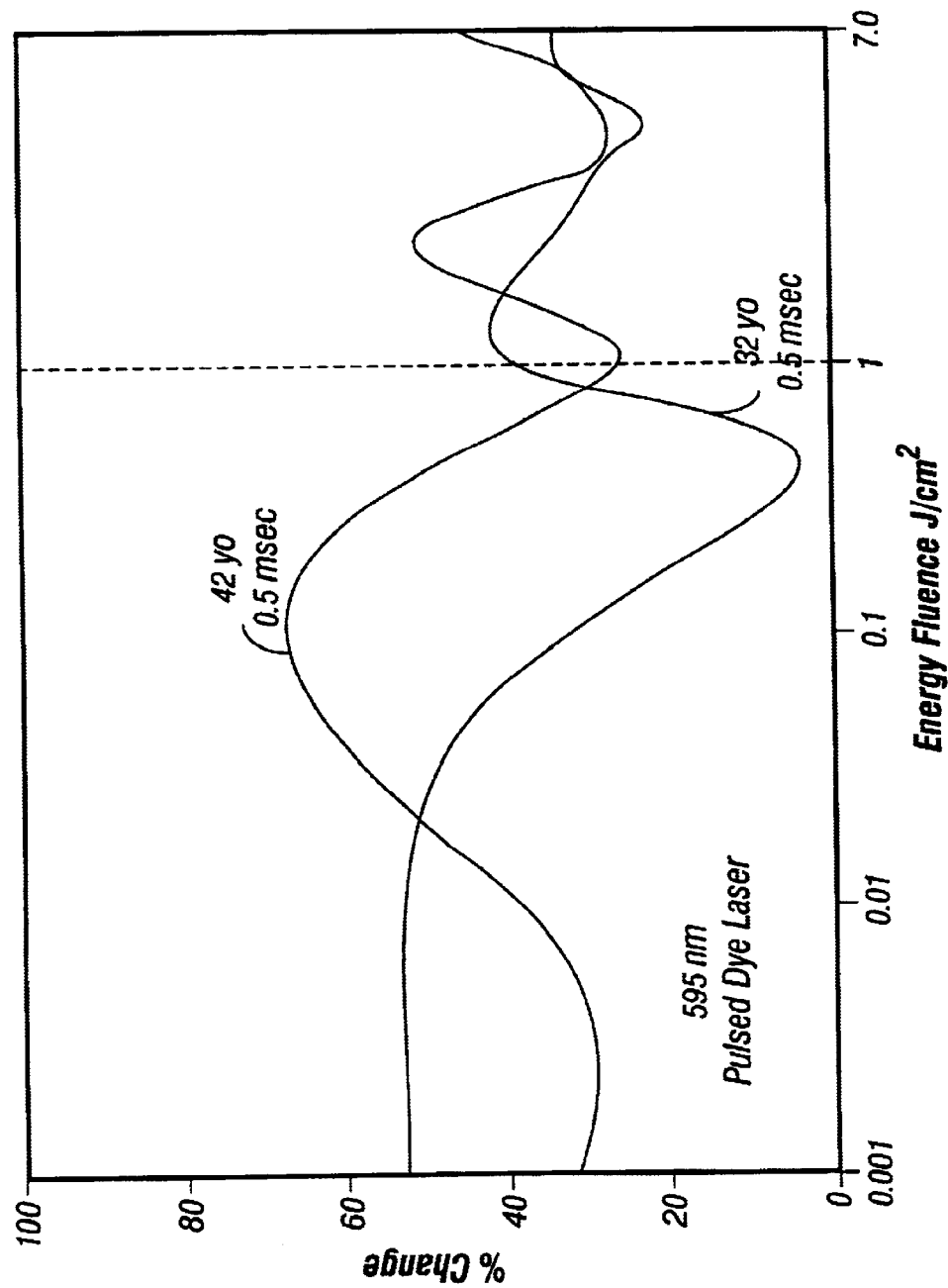
FIG. 22 shows the percent change of collagen relative to energy fluence with tissue from subjects of varying age, using 0.5 msec pulse length.
Figure 23:
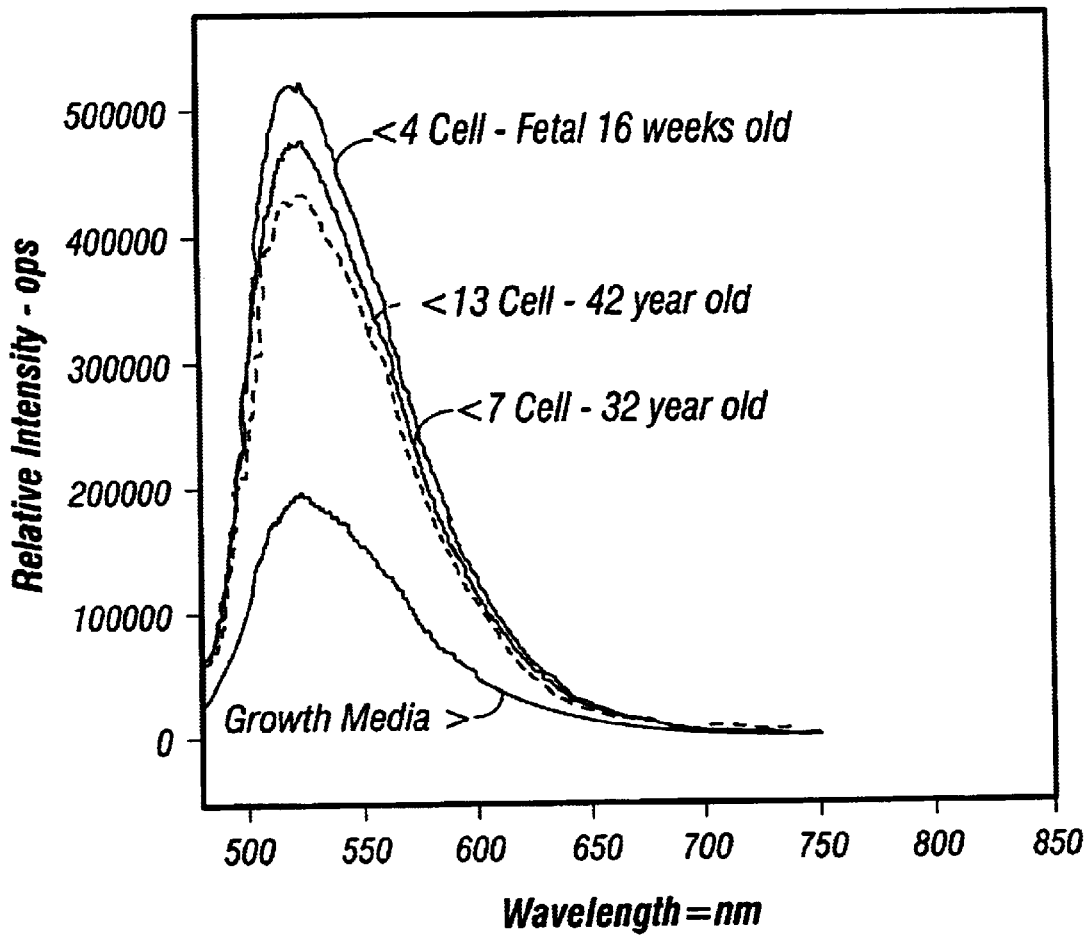
FIG. 23 shows the absorption intensity spectrum for cells from subject of varying age.
Figure 24:
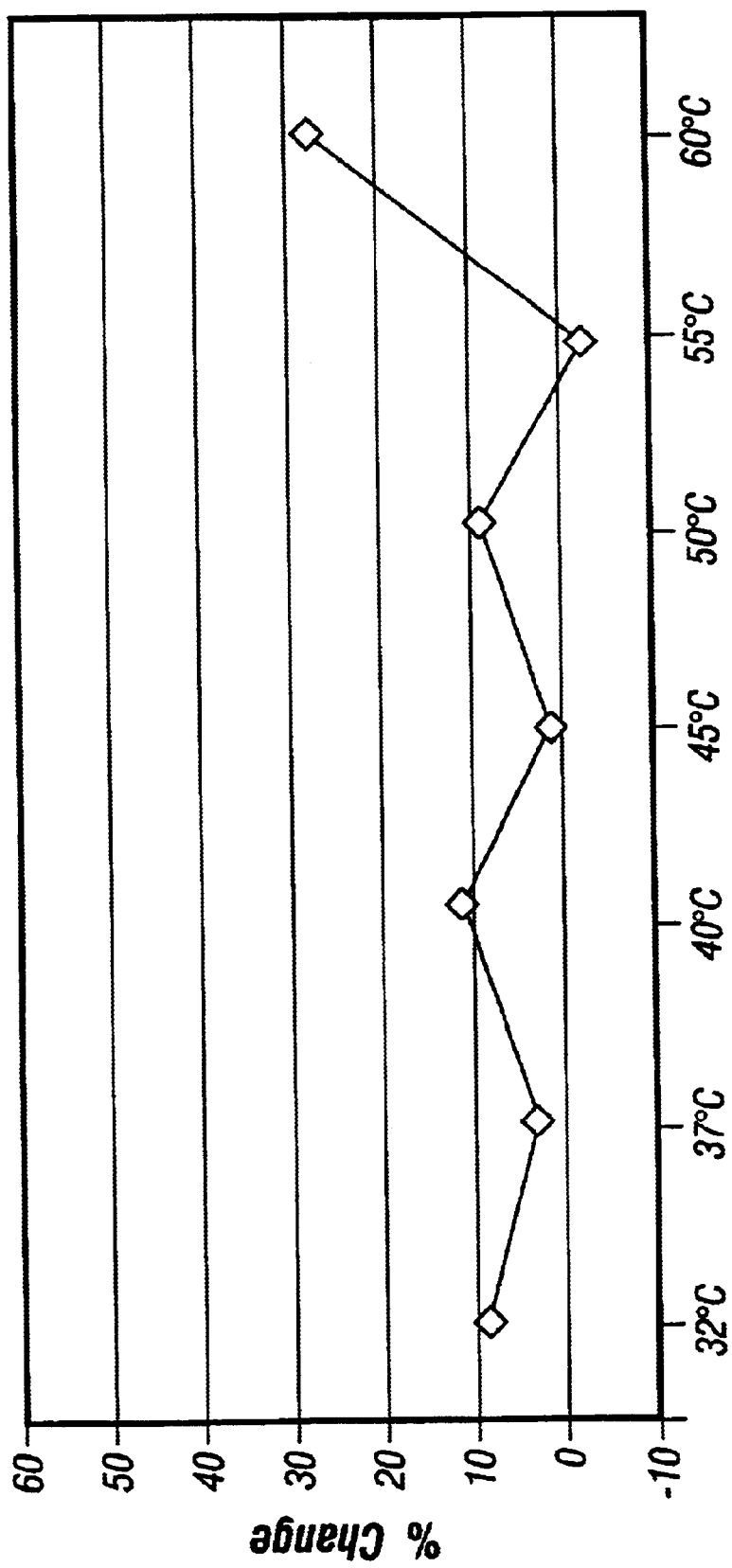
FIG. 24 shows the effect of skin temperature on collagen production for a 32 year old test subject.
Figure 25:
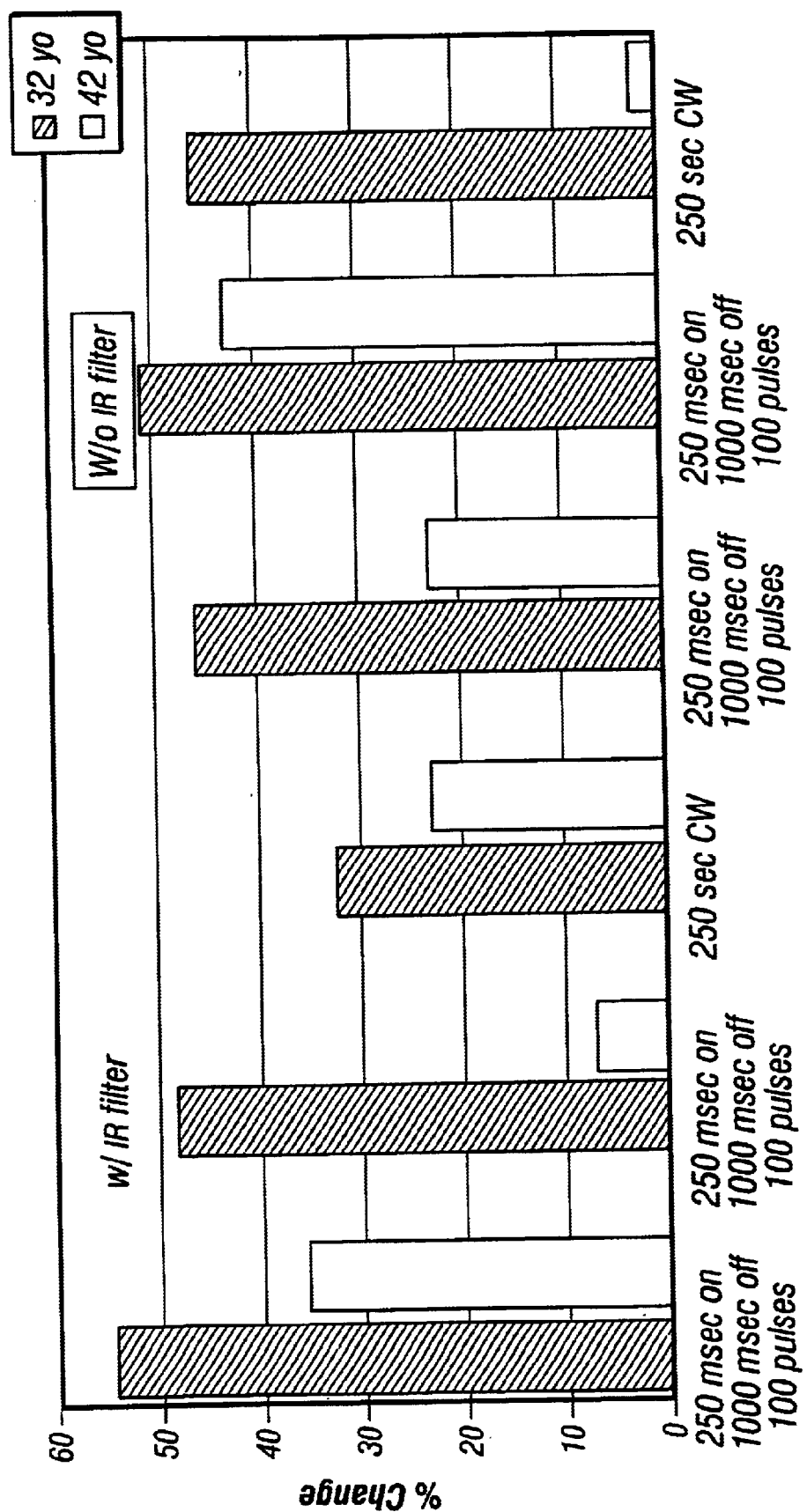
FIG. 25 shows the percent change in MMP-I production for various treatment regimen and also the effect of filtering infrared radiation from being perceived by the target tissue.
Figure 26:
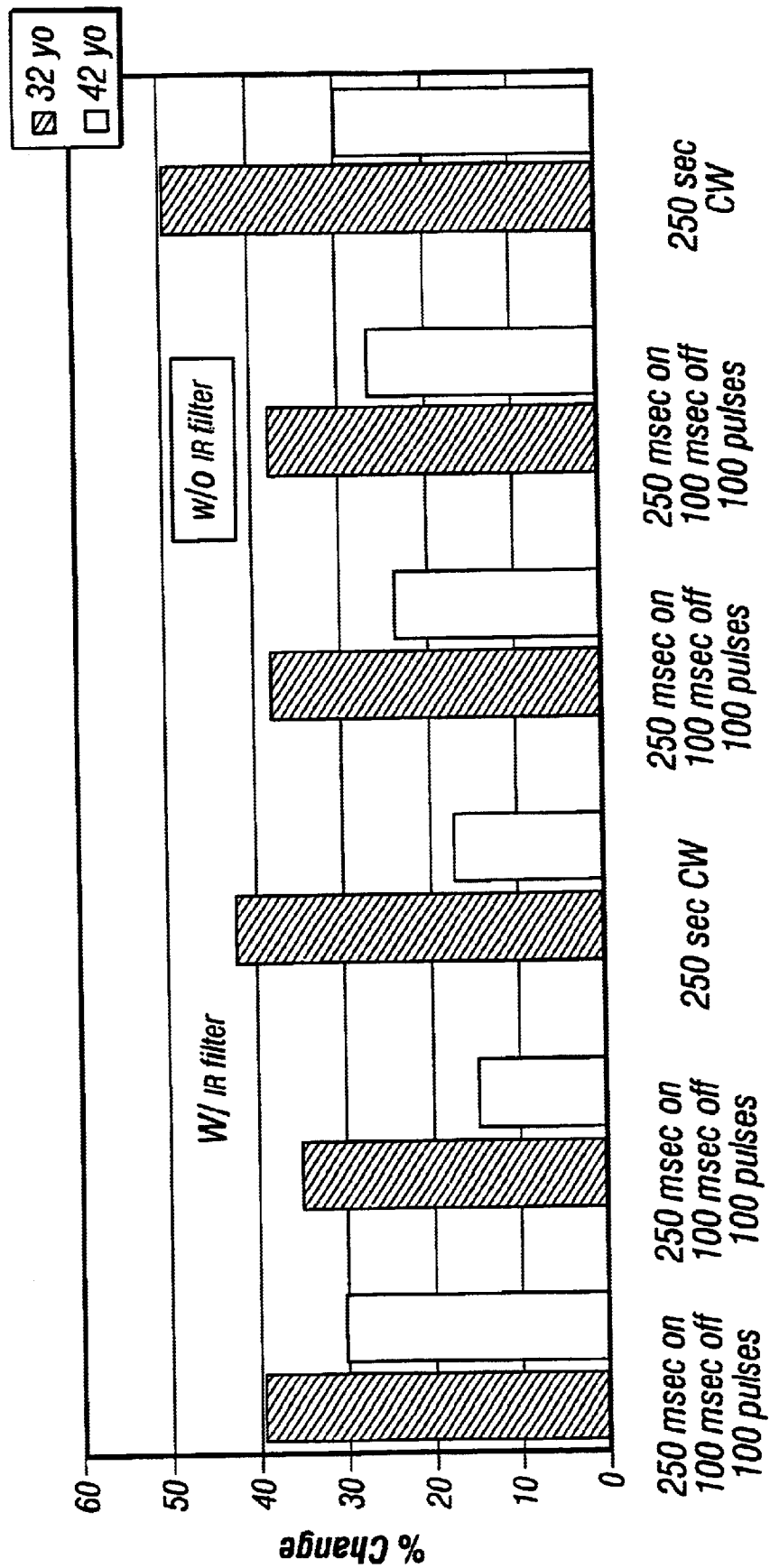
FIG. 26 shows the percent change in collagen (Procollagen 1) production for various treatment regimen and also the effect of filtering infrared radiation from being perceived by the target tissue.
Figure 27:
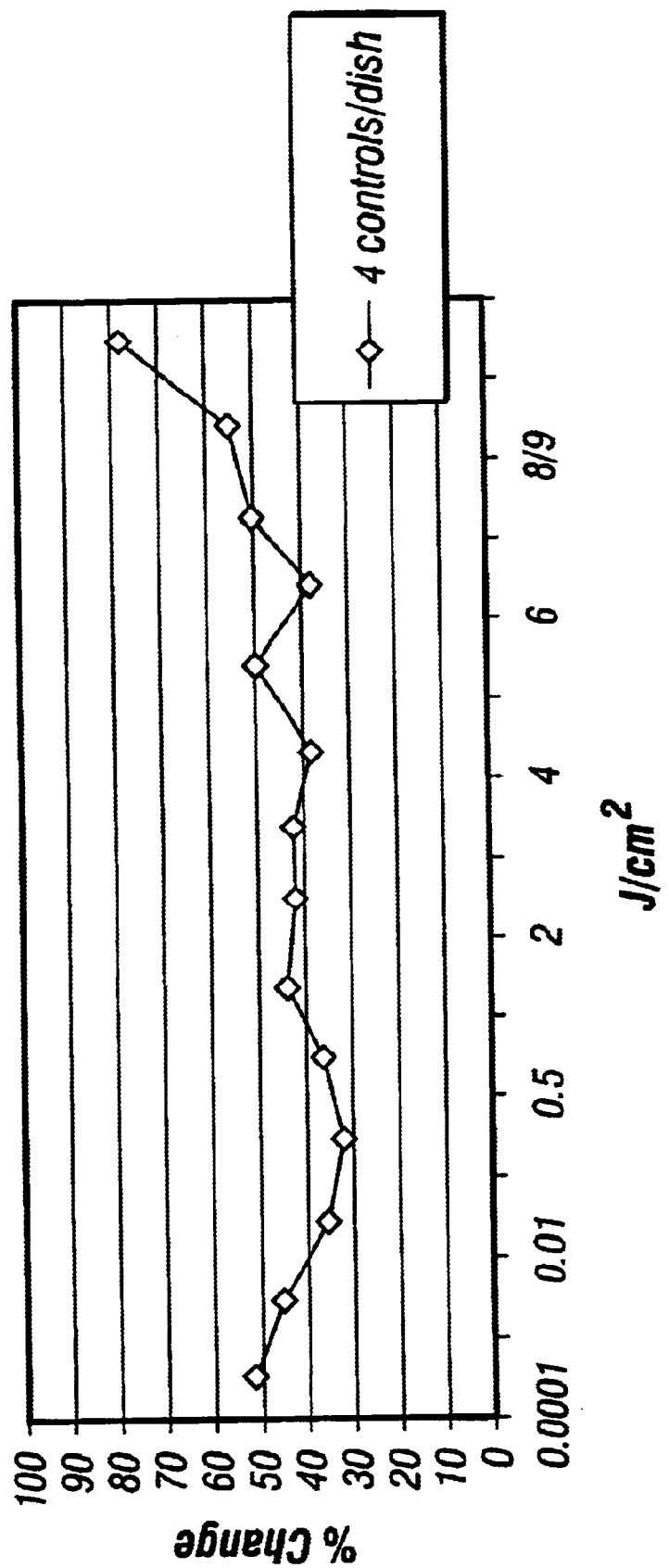
FIG. 27 shows the percent change in MMP-1 production relative to energy fluence for tissue from a 32 year old test subject, using a 595 nm pulsed dye laser having a 7 mm diameter beam and using 0.5 msec pulse lengths.
Figure 28:
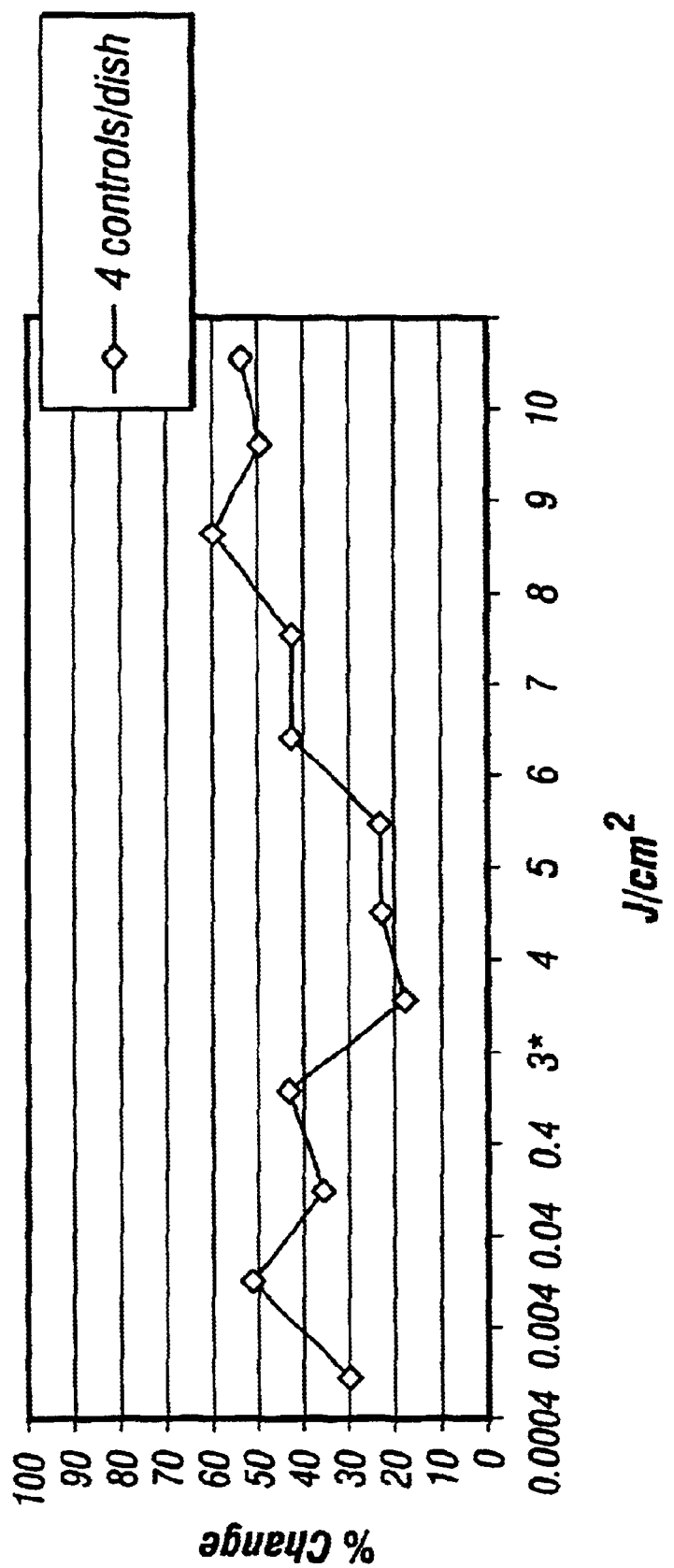
FIG. 28 shows the percent change in MMP-1 production relative to energy fluence for tissue from a 42 year old test subject, using a 595 nm pulsed dye laser having a 7 mm diameter beam and using 6.0 msec pulse lengths.
Figure 29:
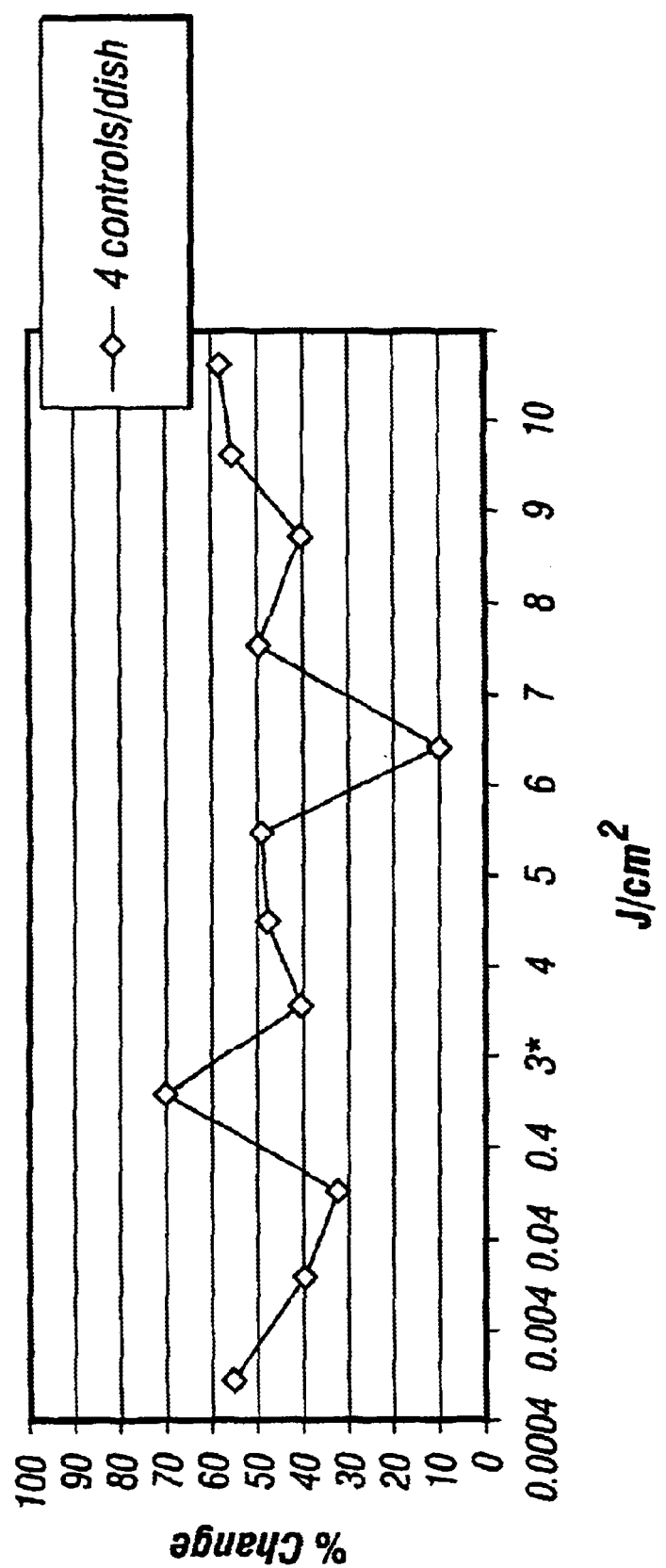
FIG. 29 shows the percent change in MMP-1 production relative to energy fluence for tissue from a 42 year old test subject, using a 595 nm pulsed dye laser having a 7 mm diameter beam and using 30.0 msec pulse lengths.
Figure 30:
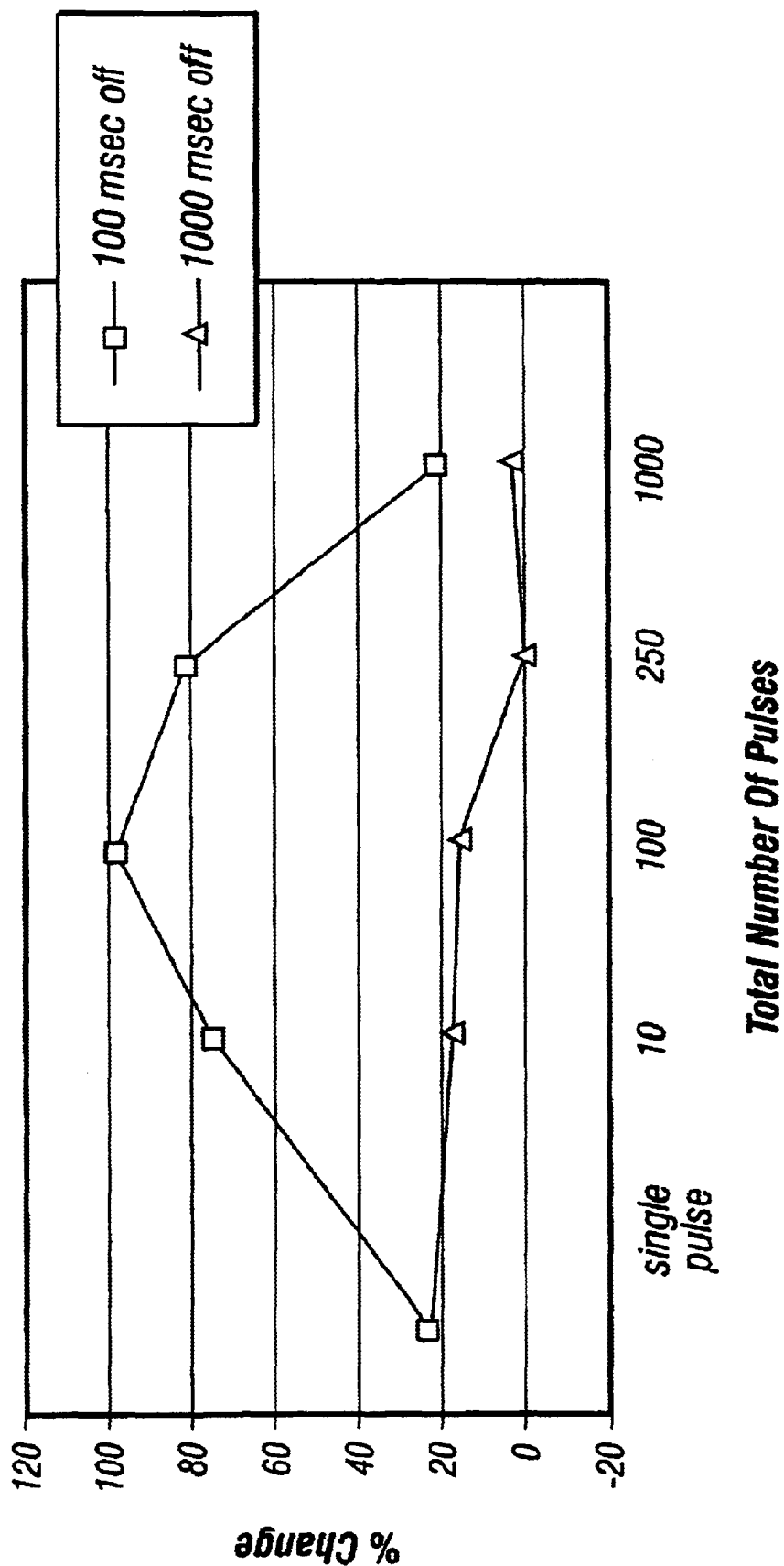
FIG. 30 shows percent change in procollagen production at 96 hours using a 590 nm led array and a 250 msec pulse length, relative to total number of pulses, for both a 10 msec and 1000 msec interpulse delay.
Figure 31:
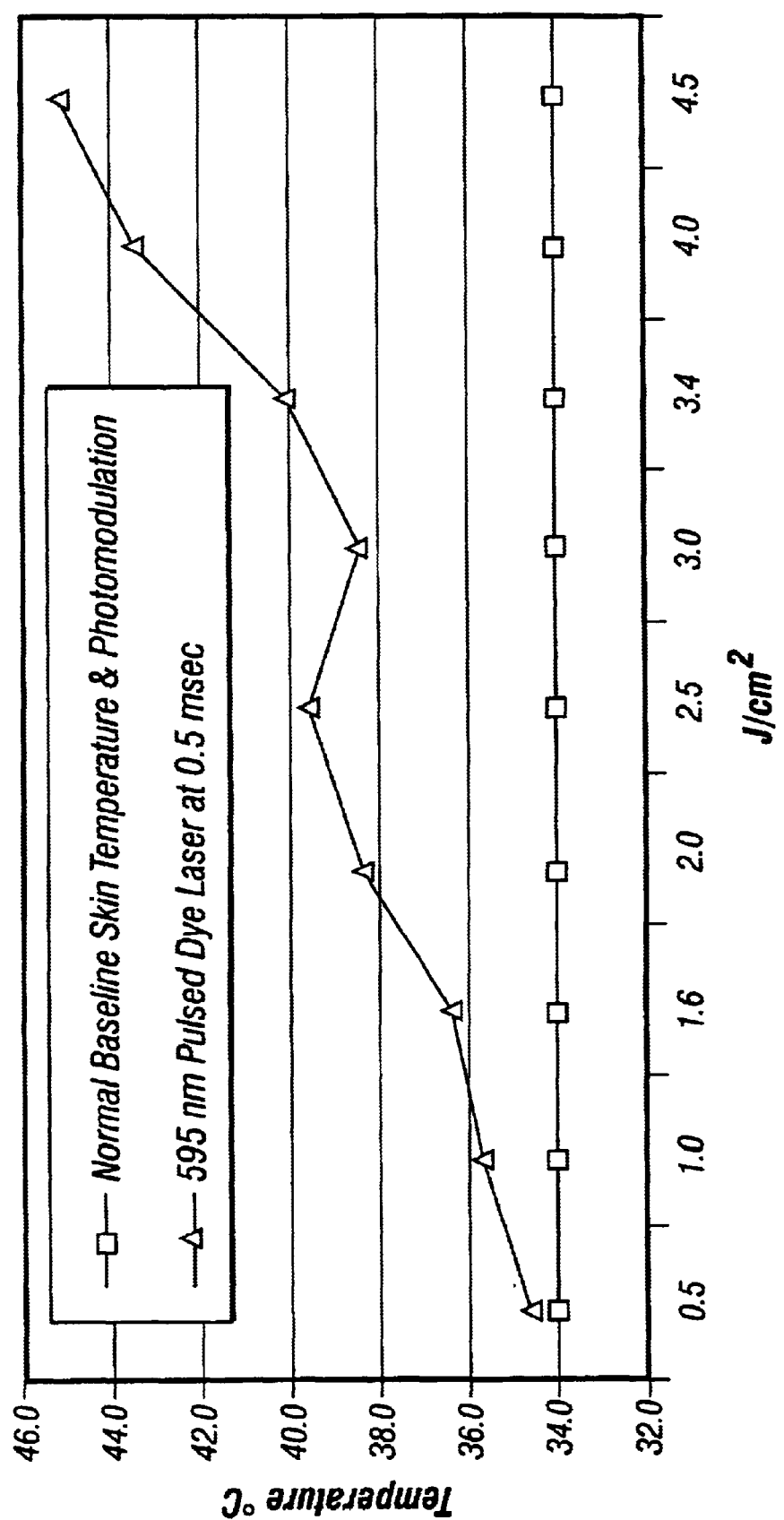
FIG. 31 illustrates the effect of skin temperature rise relative to energy fluence for both photomodulation and photothermolysis.
Figure 32:
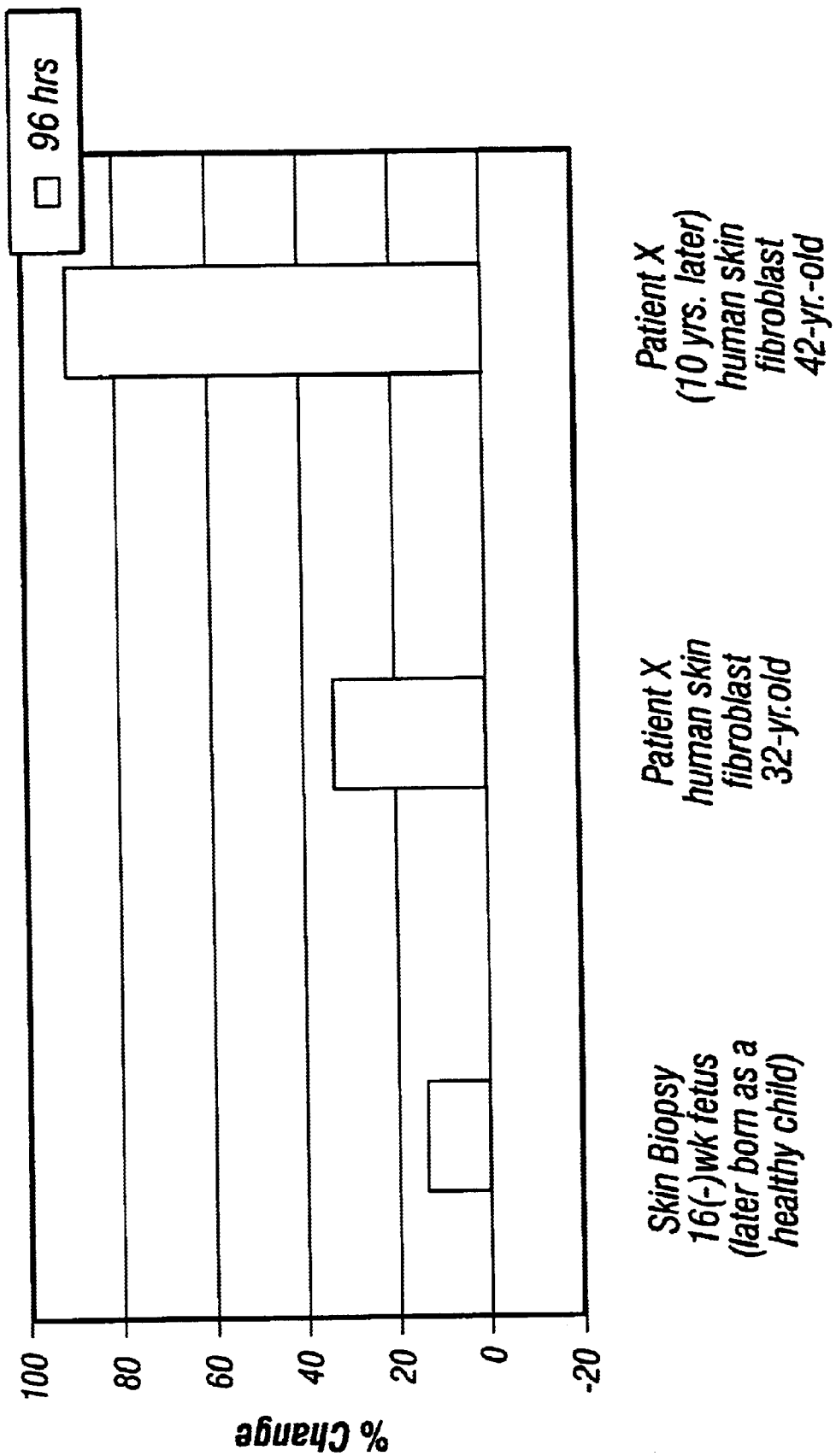
FIG. 32 depicts the percent change in collagen production for tissue samples from test subjects of various ages after subjecting the tissue to photomodulation.
Figure 33:
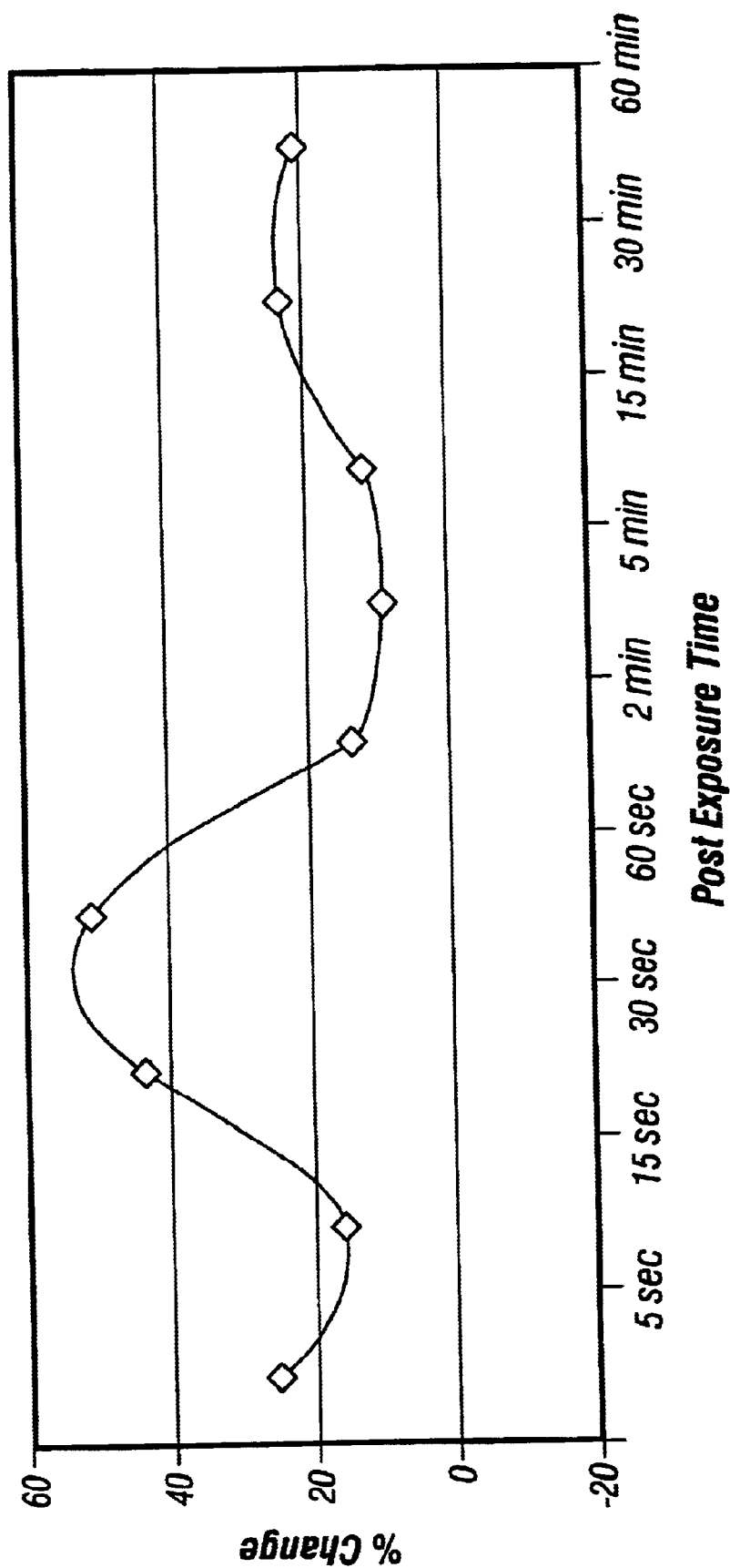
FIG. 33 shows the percent change in ATP level versus time after treatment for a tissue sample from a 42 year old test subject.
Figure 34:
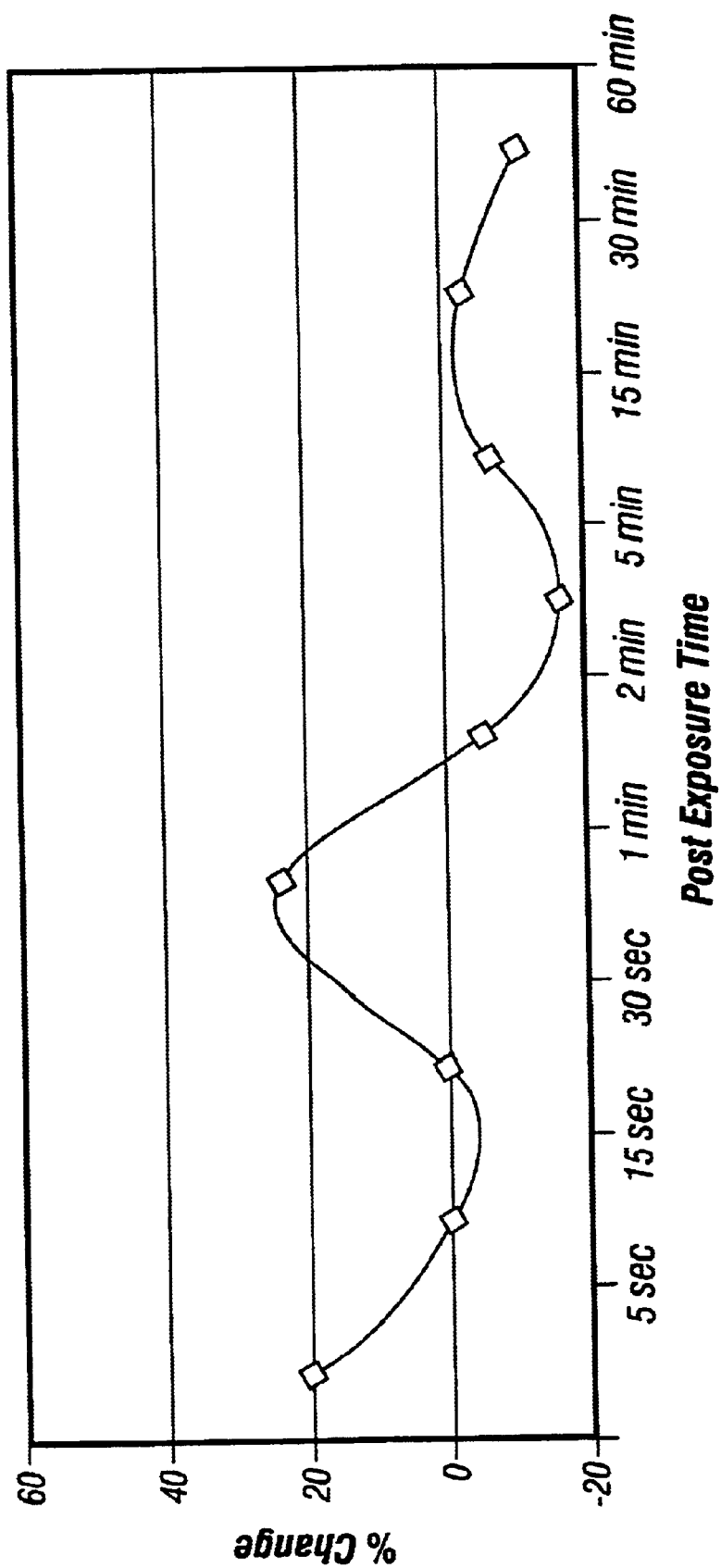
FIG. 34 shows the percent change in ATP level versus time after treatment for a tissue sample from a 42 year old test subject.
Figure 35:
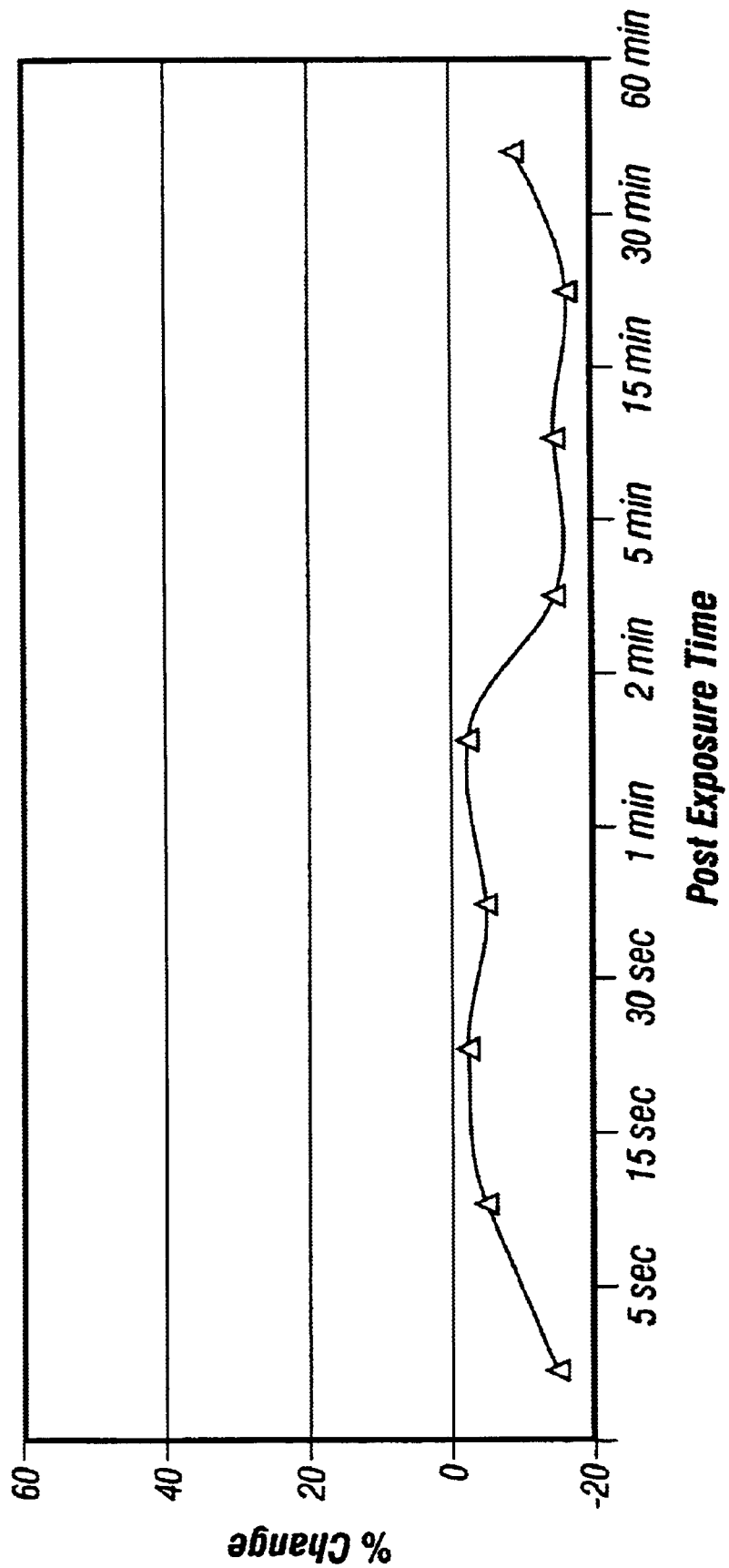
FIG. 35 shows the percent change in ATP level versus time after treatment for a tissue sample from a 16 week old fetus.
Figure 36:
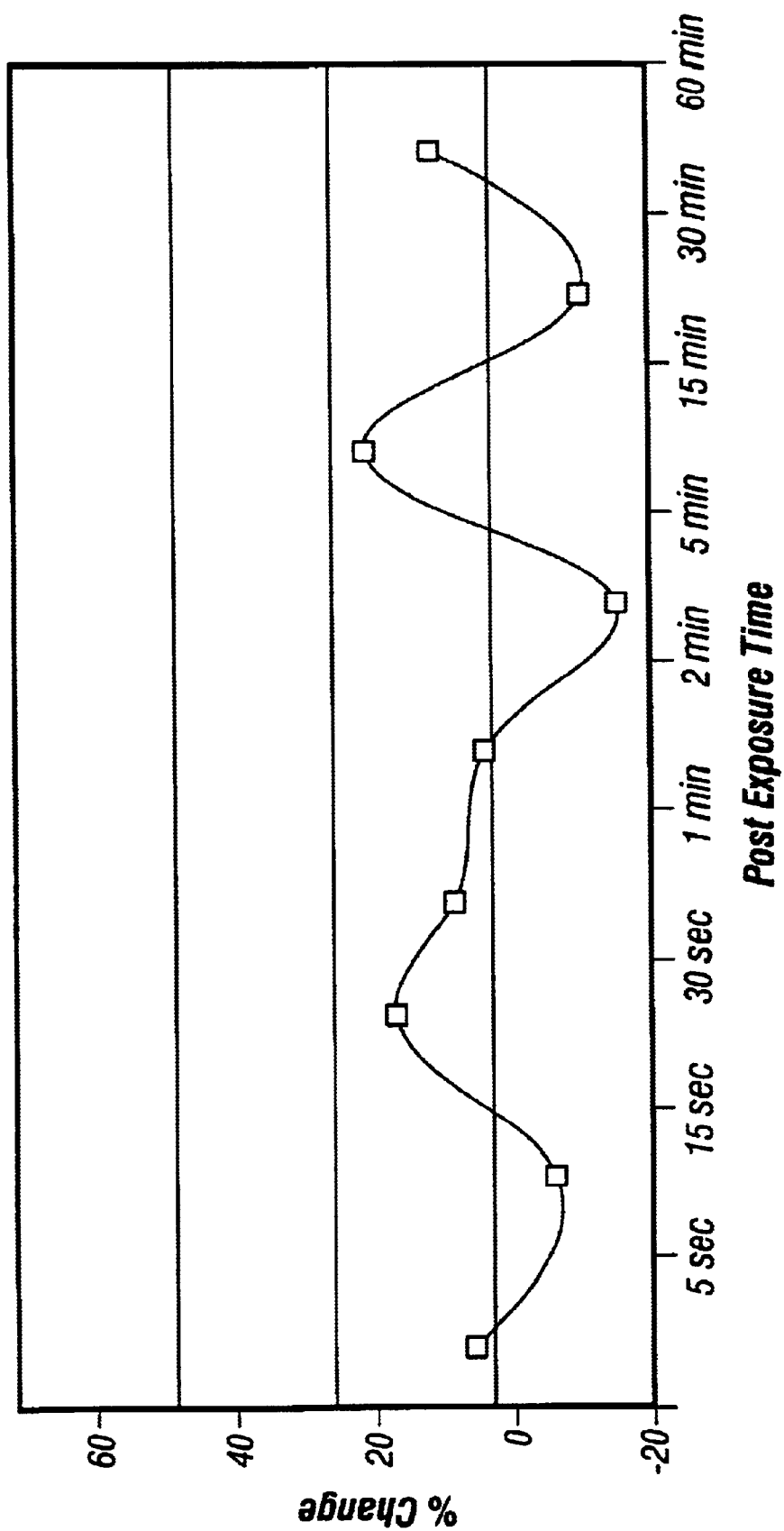
FIG. 36 shows the percent change in ATP level versus time after treatment for a tissue sample from a 32 year old test subject.
Figure 37:
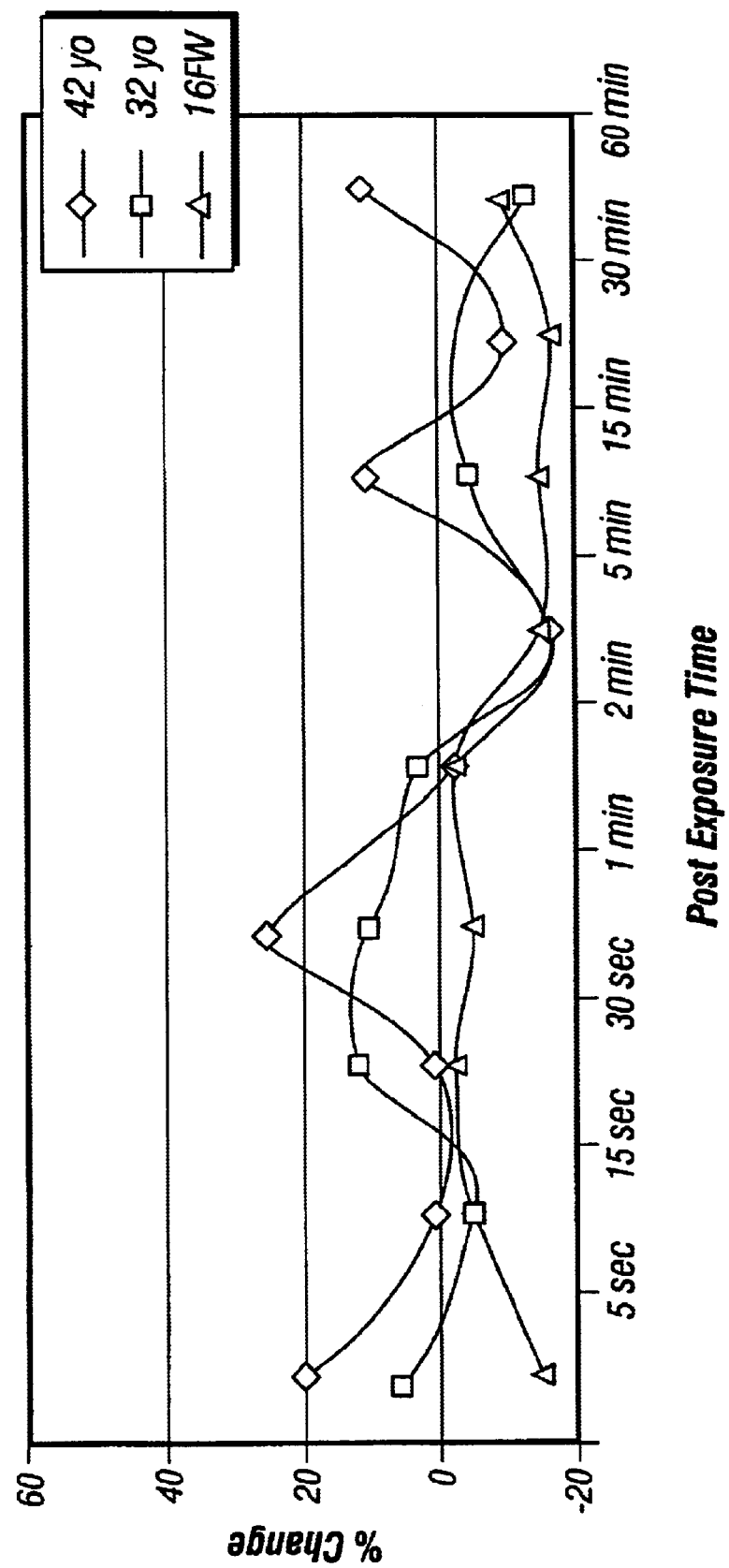
FIG. 37 shows the percent change in ATP level versus time after treatment for a tissue sample from a test subjects of varying age.

As shown in FIG. 18, at very low energy fluences, there is a trend toward greater collagen production (solid line) than collagen destruction (dashed line). Using anan LED having a dominant emissive wavelength of 590 nm it is possible to greatly improve the rate of Procollagen I production compared to the rate of production of mmp-1.

Achieving the desired pulse rate can be accomplished by methods known in the art such as capacitor timing networks, Q switches, etc. Some of these methods have been found to incorporate features that, when applied to the present invention, can provide previously unknown benefits. One such feature is the pulse wave form. Various pulse waveforms have been found to have an affect on photomodulation.

With lasers, another important feature is pulse trains. By carefully controlling the pulse duration, interpulse delay, and pulse frequency, lasers can begin to behave similarly to LEDs, when used in accordance with the method. Lasers can be made to produce a wider spectrum by both electronic means and by changing the chemical dye mix (dye lasers), in addition to traditional optical means of altering the output of the laser.

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others. In some preferred embodiments the CW mode is actually more effective than some of the pulsed modes.

Frequency (if pulsed)—e.g. higher frequency tends to be inhibitory while lower frequency tends to be stimulatory, but exceptions may occur. The total number of pulses is also a modulating factor and in many cases the higher numbers of pulses tend to be more inhibitory and smaller numbers more stimulatory.

Duty cycle—This is the device light output repetition cycle whereby the irradiation is repeated at periodic intervals, also referred to herein as the interpulse delay (time between pulses when the treatment session comprises a series of pulses).

Beam Profile Shaping—This refers to the pattern of radiation exposure that the skin or target tissue is exposed to. Different beam profiles can alter the photomodulatory effects of a particular treatment regimen (i.e., the combination of wavelength, pulse or CW duration, pulse frequency, interpulse interval, etc.)

The present invention may be used with or without the application of a topical composition to the skin or target tissue. One function of such compositions may be to alter the refractive index of the skin or target tissue, so that the absorption spectrum of the skin or target tissue is closer to the emissions spectrum of the source of electromagnetic radiation. Suitable active agents for use in topical compositions applied to the skin in accordance with the present invention include one or more of Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, minoxidil, a dye, a natural or synthetic melanin, a metalloproteinase inhibitor, proline, hydroxyproline, an anesthetic substance, chlorophyll, bacteriochlorophyll, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both natural and synthetic, as well as combinations thereof.

While not a limiting factor, a common aspect of the most useful natural chromophores of the present invention is found in their chemical structure. Naturally occuring chromophores have a metal-ligand bonding site. The chemical structure of chlorophyll a is characterized by its $R=CH_3$ group. A magnesium atom is present at the metal-ligand bonding site in the Figure. Chlorophyll a exhibits absorption maxima at 409 nm, 429 nm, 498 nm, 531 nm, 577 nm, 613 nm, and 660 nm. Chlorophyll b is characterized by $R=CHO$ exhibits absorption maxima at 427 nm, 453 nm, 545 nm, 565 nm, 593 nm, and 642 nm. It can be readily seen that various types of chlorophyll, or combinations thereof, can be used as topically applied chromophores to assist the absorption of certain wavelengths of light delivered through the skin or soft tissue for various treatments. When used to enhance the absportion of a wavelength of light that coincides with an absorption maxima of target cells such as human fibroblasts, treatment can be even more effective or can be carried out with reduced light intensities or can produce multiple beneficial effects, such as treating acne bacteria and reducing or eliminating acne scarring.

The alkaline hydrolysis of chlorophyll opens the cyclopentanone ring and replaces the methyl and phytyl ester groups with sodium or potassium. These resulting salts are called chlorophyllins and are water soluble. The alkaline hydrolysis of the chlorophyll shown in Figure X will result in a NaMg Chlorophyllin, but other salts can easily be formed by replacing the Mg atom in the chlorophyll with other metals or reactive transition metals, for example, such as copper, aluminum, iron, metal chelates, or antibody complexes. Such a substitution is made by treating the chlorophyll with an acid causing the Mg to be removed and replaced by $H_2$ which, in turn, is easily replaced by other metals.

Chlorophyll and to some extent the other photosystems such as phycobilin, rhodopsin, etc., have at their core in the reaction centers, or antennae, what are called 'photosystem I and photosystem II'. What this this refers to is either the isolation or 'fractionalization' of existing photosystems or synthesize them altogether or genetically engineer and then harvest or produce them. Further, the artificial, synthetic, or fragmented natural or genetically engineered reaction centers consist of at least one of an electron donor and at least one of an electron receptor and are preferably enclosed in some type of membrane like capsule or vehicle. Conceptually, this is analagous to the conventional lead-acid storage batteries where one separated the chemicals into two compartments and then generated a charge across the plates that connect them. Here, diffusion of electrons across a membrane or diffusable barrier can establish a 'gradient'. This can be done with compounds such as chlorophyll, carotenoids, phycobilin, and many of the topical compositions disclosed herein. In some cases it may be important to use a combination of at least two of these to get the electron donor and receptor set up in a suitable manner.

Unlike artifically synthesized chromophores, naturally occuring chromophores bear the similar attribute of having the metal ligand bonding site which will dissociate the metal ion upon treatment with an acid. The acid content of human skin is sufficient to trigger this reaction and, in turn, cause the chlorophyll, having lost the metal ion, to become less soluble in water. The resulting chlorophyll, or other naturally occuring agent that dissociates a metal ion from a ligand bond under acidic conditions such as porphyrin for example, makes an excellent topical composition with superior optical properties for acting as a chromophore to enhance low-intensity light therapies. In another embodiment of the invention, therefore, the preferred chromophore is a compound having a metal ligand bond that dissociates the metal ion under acidic conditions. In one embodiment of the invention, topical skin care formulations may be used for altering the pH or acidity of the skin.

In addition to being an effective treatment method for reducing and eliminating the presence of common acne bacteria such as acnes vulgaris and for safely treating conditions such as pseudofolliculitis barbae, acne rosacea, and sebaceous hyperplasia, the present invention also has application to the reduction of cellulite. Using any of the light sources suitable for use as described herein, adipocyte cells can be photomodulated. Photomodulation increases the local microcirculation in the cellulite and alters the metabolic activity of the cells. Enhanced local microcirculation, metabolism or enzymation activity, or combinations thereof, may be produced by photomodulatory means. To enhance the treatment, any of the topical chromophores as previously described can be used or non-chromophoric compositions can be used in conjunction with any of the photomodulatory methods, including low-intensity light therapy. Further photothermal means may be used to destroy adipocyte cells alone or in combination with photomodulatory means, with or without the use of exogenous chromophores.

Many living organisms—both animals and plants—have as one of their major defense mechanisms against environmental damage to their cells and DNA repair system. This system is present in many if not all living organisms ranging from bacteria and yeasts to insects, amphibians, rodents and humans. This DNA mechanism is one which is involved in processes to minimize death of cells, mutations, errors in copying DNA or permanent DNA damage. These types of environmental and disease and drug related DNA damage are involved in aging and cancer.

One of these cancers, skin cancer, results from ultraviolet light damage to the DNA produced by environmental exposure to natural sunlight. Almost all living organisms are unavoidably exposed to sunlight and thus to these damaging UV rays. The damage which is produced is a change in the structure of the DNA called pyrimidine dimmers. This causes the DNA structure to be altered so that it cannot be read or copied any longer by the skin cells. This affects genes and tumor development and proper functioning of the immune system.

The use of such naturally derived or artificially created or genetically engineered photolyase enzymes or related enzymes or other proteins functioning for DNA or RNA repair have a wide variety of applications. For example, the ability to treat skin damaged by sunlight/ultraviolet light of disease and to repair, reverse, diminish or otherwise reduce the risk of skin cancer could be used either as a theraputic treatment or as a preventive measure for people with severely sundamaged skin, with precancerous skin lesions, or with skin cancer.

This principle applies not only to skin cells and skin cancer but to a very broad range of skin and internal disorders, diseases, dysfunctions, genetic disorders, damage and tumors and cancers. In fact potentially any living cells might have beneficial effects from treatment with photolyase or similar proteins in combination with light therapy.

While in nature the light to activate the photolyase typically comes from natural sunlight, essentially any light source, laser and non laser, narrow band or broader bandwidth sources can activate the photolyase if the proper wavelengths and treatment parameters are selected. Thus natural sunlight filtered through a selective sunscreen could be used to activate both native and exogenously applied photolyases. Another treatment option would be to apply the photolyase and then treat with a controlled light source exposure to the proper wavelength band and parameters. A wide variety of light sources could be utilized and the range of these is described elsewhere in this application. For example a low energy microwatt narrow band but multispectral LED light source or array with mixed wavelengths could be utilized. Another embodiment is a filtered metal halide light source with a dominant wavelength of 415 nm+/−20 nm and an exposure of 1–30 minutes at 1× $10^{-4}$–100 milliwatts output can be used. Such exposure would occur minutes to days after application of a topical product containing photolyase.

Another example would be the repair of cells in the skin which have environmental damage but instead of repairing the cells which lead to skin cancer the cells which lead to aging (photoaging) of the skin are targeted for this therapy. In one embodiment, kin fibroblasts which have been sun damaged are treated with a photolyase and subsequently the photolyase is photomodulated with blue light to set in motion the DNA repair mechanism of photolyase—that is photoreactivation. This allows the repair of the structure and thus the normal functioning of the fibroblast DNA thus allowing normal functioning and proliferation of these fibroblasts—which produce the proteins such as collagen and elastin and hyaluronic acid and matrix ground substance which cause skin to be firm and elastic and youthful in appearance—thus producing anti-aging or skin rejuvenation effects in the skin as well as improving the structure and healthy function of the skin.

Various cofactors which are involved in this photoreactivation process can also be added either topically or systemically to further enhance or improve the efficiency of this process. Other cofactors needed in the production of these proteins once the cells recover normal function also may be added topically or systemically to enhance the anti-aging or skin rejuevenation process. The delivery of both the photolyase and/or the cofactors described above can be enhanced by utilizing ultrasound to increase skin permeability or to increase transport across the skin barrier and into the skin and underlying tissues. Removal of a portion of the stratum corneum of the skin can also be used, alone or incombination with ultrasound, to enhance penetration and delivery of these topically applied agents. Additionally such methods of removing or altering the stratum corneum can assist in penetration of the light or the efficiency of same or allow use of lower powered light sources including home use devices such as battery powered LED sources.

A variety of sources exist for obtaining photolyases. These may include native naturally occurring photolyases, compounds derived from other living organisms (that is one may use bacterially derived, or yeast derived, or plankton rederived, or synthetic or genetically engineered, photolyases and use them in human skin for beneficial effects thus not limited to same species derived photolyases. One known photolase is derived from Anacystis nidulans while others can be derived from bacteria—yeast in fact protect themselves with a photolyase which can be used in humans, other microorganisms, plants, insects, amphibian and animal sources exist.

The photolyase enzymes function by light induced electron transfer from a reduced FAD factor to the environmental exposure produced pyrimidine dimers. The use of free radical inhibitors or quenchers such as antioxidants can also be used to supplement the photolyase therapy. Other light activated chromophores may be utilized with light sources and properly selected parameters to further enhance, stimulate, photomodulate, photoactivate or photoinhibit the target or supporting cells or tissue to promote the most effective treatment.

There are many causes of free radical damage to cells. In one embodiment wound healing can be accelerated by utilizing a combination of antioxidants, cell growth factors, direct photomodulation (photoactivation) of cells, and photoreactivation through photolyases. Topical or systemic therapy with the proper cofactors and replacing any deficiencies of cofactors can further enhance wound healing. For example, a chonic leg ulcer wound could be treated with an antioxidant mixture of vitamin E, vitamin C and glutathione, as well as cofactors such as fatty acids and keto acids and low level light therapy using and LED array with parameters selected to photostimulate fibroblasts and epithelial cells could also receive treatment with a photolyase and blue light therapy thus greatly accelerating wound healing and healing wounds or bums that would otherwise not be treatable. It is possible by selecting certain photomodulating or electromagnetic modulating parameters to cause 'excessive' stimulation and cause, for example, in the case of photomodulation the generation of triplet states and also singlet states producing reactive oxygen species (ROS) or 'free radicals'. These ROS can 'trigger' a cascade of cellular and subcellular signals and events which are destructive or inhibiting to various key cellular reactions. One such example is the production of ROS by cigarette smoke thus producing an increase in MMP-1 or collagenase enzyme. This can destroy existing or newly formed collagen and thus cause or worsen aging changes in the skin. Similarly, certain wavelengths of ultraviolet light produce increases in MMP-1 and other destructive MMP enzymes. It is illustrated in FIGS. 18–21 that photomodulation can also produce increased MMP-1 depending upon the modulating parameters. This is also one reason that including MMP inhibitors in the topical agents can be useful to increasing stimulation of collagen. There are also other MMP enzymes which degrade or destroy various other structural proteins produced by fibroblasts and these proteins and MMP are also subject to photomodulation and exogenous agents manipulation as well.

The potential uses of photolyases and light therapy include: the treatment or repair or reverse nerve damage or diseases including spinal cord injuries and diseases; cancer or cancer treatment related problems including radiation and chemotherapy; cervical dysplasia and esophageal dysplasia (Barrett's esophagus) and other epithelial derived cell or organ disorders such as lung, oral cavity, mucous membranes, etc.; eye related diseases including but not limited to macular degeneration, cataracts, etc.

There are very broad health and commercial applications of photolyase mediated photorepair or photoreactivation of DNA (or RNA) damage with flavin radical photoreduction/DNA repair via photomodulation or native or exogenously applied natural or synthetic or genetically engineered photolyases. The addition of topical. Oral, or systemically administered photolyases and also their cofactors or cofactors of the cells whose DNA is being repaired further enhance these applications. The enhanced delivery of such substances topically via ultrasound assisted delivery, via alteration of the skin's stratum corneum, and/or via special formulations or via special delivery vehicles or encapsulations are yet an additional enhancement to this process.

The use of a topical light activated exogenous chromophore such as most of the agents listed in this application present no risk of DNA damage and also are generally very safe products—many are natural such as chlorophyll and can be safely used in children and pregnancy and child bearing age women. In addition the treatment is only activated where the topical agent is applied—unlike the use of oral psoralen drugs that activate not only the entire skin but also the retina and other tissues. The light used for this therapy is not only low in power, but it is for the most part visible or infrared light and is not ultraviolet-producing no DNA damage. Note, however, that in certain preferred embodiments of the invention, infrared light is specifically filtered out of the light source. Typical means of performing this filtration are by placing a neutral density filter, one that blocks the transmission of infrared wavelength radiation, over the light source.

Thus the use of photomodulation or photothermal activation of exogenous light activated chromophores such as described herein represents a signicant advance in safety and efficacy.

The photolyase embodiments described above also have some application for diseases such as psoriasis. For some cases of psoriasis are very extensive covering large amounts of the surface area of the body and may be resistant to other known therapies. The application of a topical fomulation to the areas not being treated—or to all the body areas exposed to the traditional psoriasis phototherapy could receive a post treatment with the photolyase and blue light therapy—think of this as a type of 'antidote' to the ultraviolet psoriasis phototherapy wherein the repair of DNA damage to normal tissue was facilitated immediately following the psoriasis therapy—thus reducing significantly the risk of skin cancer and photoaging in future years.

Another embodiment involves the use of such a photolyase preparation in the evening after returning from a long day of occupational sun exposure or after an accidental sunburn. A spray or lotion containing the photolyase could be applied and then photorepair/photareacitvation of the acutely damaged DNA in the skin could be performed—and this could be performed with a large beam diameter home therapy unit—of by a white light source which contained enough of the desired wavelength at the proper parameters to produce this reaction. Additionally an antioxidant skin formulation could be also applied to minimize erythema and other undesired effects of the sunburn. One such embodiment would be the preparation described earlier with a combination of vitamin C, vitamin E and glutathione and free fatty acids and one or more keto acids. A similar formulation could contain these agents but utilize only one or two of the three antioxidants listed.

In vitro fertilization processes can also be enhanced by photomodulation—with or without an exogenous chromophore. This can simply target the cells or subcellular components themselves, as described in the applicants copending U.S. patent application Ser. No. 09/894,899 entitled "Method and Apparatus for Photomodulation of Living Cells", which is hereby incorporated by reference in its entirety.

This can result in a greater success rate of fertilization and/or growth of embryos or other desirable effects on this process. In one embodiment an LED light source is used to treat sperm of animals or humans or genetically engineered embryos or subcomponents thereof to enhance fertilization.

In another embodiment photolyase or other photoreparative or light activated DNA repair proteins or substances combined with photomodulation can be utilized to 'correct' DNA damage in embryonic tissues thus generating a normal or more normal embryo. This can be performed in vitro or in utero (utilizing tiny fiber optic delivery of the proper light parameters—or the light can be delivered from outside the body into the womb without the risk of introducing a fiber optic device.

Another process in which photomodulation can be utilized for significant benefit is in the stimulation of proliferation, growth, differentiation, etc of stem cells from any living organism. Stem cells growth and differentiation into tissues or organs or structures or cell cultures for infusion, implantation, etc (and their subsequent growth after such transfer) can be facilitiated or enhanced or controlled or inhibited. The origin of such stem cells can be from any living tissue or organism. In humans stem cells for these embodiments may come from any source in the human body, but typically originate from the bone marrow, blood, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation. The use of photomodulation alone or in combination with other electromagnetic modulation (i.e., the use of radiation outside the visible spectrum to modulate cellular activity, collagen production, fibroblast production, fibroblast-derived cell production, etc.) and/or adjunctive chromophores or cofactors can be used to not only stimulate the proliferation of stem cells, but also to 'guide' or stimulate the differentiaion of stem cells into the desired cell line(s).

This modulation can be performed on more differentiated tissues and not simply embryonic tissues. Thus such cell sources as umbilical cord blood or bone marrow stem cells may be modulated as well as stem cells which exist or are latent in end organs (an example of which would be the stem cells which exist in the hair bulge and can be photomodulated or activated to grow or regrow hair).

With photomodulation or electromagneticmodulation there is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

Our analogy for photomodulation of stem cells is that a specific set of parameters can activate or inhibit differentiation or proliferation or other activities of a stem cell. Much as a burglar alarm keypad has a unique 'code' to arm (activate) or disarm (inhibit or inactivate) sending an alarm signal which then sets in motion a series of events so it is with photomodulation of stem cells.

Different parameters with the same wavelength may have very diverse and even opposite effects. When different parameters of photomodulation are performed simultaneously different effects may be produced (like playing a simple key versus a chord on a piano). When different parameters are used serially or sequentially the effects are also different—in fact depending on the time interval we may cancel out the prior photomodulation message (like canceling burglar alarm).

The selection of wavelength photomodulation is critical as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (eg. reduced ubiquinone from certain anticholesterol drugs) or antioxidant status, diseases, etc. It is also possible to use a topical or systemic (or both) preparation which contains ubiquinone or its natural or synthetic derivatives to enhance the effects of photomodulation or photoactivation.

The as yet unknown mechanism, which establishes 'priorities' within living cells, can be photomodulated. This can include even the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

Another application of photomodulation is in the treatment of cellulite. Cellulite is a common condition which represents a certain outward appearance of the skin in certain anatomic areas—most commonly on the upper legs and hips which is widely regarded as cosmetically undesirable. Cellulite is the result of a certain anatomic configuration of the skin and underlying soft tissues and fat which may involve abnormalities of circulation or microcirculation or metabolic abnormalities—predominantly in the fat and supporting tissues. Photomodulation or photothermal treatments of the adipocytes (fat cells) or their surrounding supporting structures and blood supply alone or in combination can reduce the appearance of cellulite and/or normalize the structure and function of the tissues involved with the cellulite.

Photomodulation of adipocytes can be performed using endogenous chromophores suche as the adipocytes themselves, their mitochondria or other targets within the adipocyte electron transport system or respiratory chain or other subcellular components. Exogenous light or electromagnetically activated chromophores can also be photomodulated (photoactivated or photoinhibited) or photothermal interactions can also occur. Examples of such chromophores are listed elsewhere in this application and can be topically or systemically introduced into the target tissues or adipocytes or surrounding blood vessels. The use of externally or internally applied ultrasound can be utilized either to enhance delivery of the chromophore or to alter local circulation or to provide thermal effect or to provide destructive effect or any combination of these actions.

In one embodiment the chromophore is delivered into the fat layer under the skin on the thigh using external ultrasound to enhance skin permeability and also enhance transport. The alteration of the stratum corneum alone or in combination with the ultrasound can further enhance delivery of the chromophore. External massage therapy from various techniques can be used to enhance the treatment process. In another embodiment chromophore is injected into the fat layer prior o treatment with light. Some light therapy with or without ultrasound may be used to photomodulate or photothermally or ultrasonically increase or otherwise alter the circulation or microciruclation or local metabolic processes in the areas affected by cellulite or other tissues. The proper light parameters are selected for the target adipocytes, blood vessels, exogenous chromophores, etc. Since some of the target tissues in cellulite are deeper than for example wrinkles or acne, typically long enough wavelengths of light must be utilized so that the light penetrated deeply enough to reach the target tissue.

Various topical or systemic agents can also be used to enhance the cellulite reduction treatments. Some of these include various cofactors for the metabolic or adipocyte interactions described and have been previously described herein.

Additional topical agents for inhibiting hair growth include inhibitors of ornithine decarboxylase, inhibitors of vascular endothelial growth factor (VEGF), inhibitors of phospholipase A2, inhibitors of S-adenosylmethionine. Specific examples of these, but not limited to, include licorice, licochalone A, genestein, soy isoflavones, phtyoestrogens, vitamin D and derivatives, analogs, conjugates, natural or synthetic versions or genetically engineered or altered or immunologic conjugates with these agents. Also the same topical agents, exogenous light activated chromophores and treatments described for cellulite above also are hereby incorporated into methods for reducing the growth of hair. Increasing the circulation or microcirculation of the hair bearing skin may also be accomplished by simply producing vasodilation by any method know to those skilled in this art. Some examples of topical agents which might be used to create such vasodilation include, but are not limited to: capsicum, ginseng, niacinamide, minoxidil, etc.

In conjunction with the present invention, photomodulation may occur at energy levels higher than 1 J/cm2, but the chance for photothermal injury to the skin increases. To reduce thermal injury to the skin, while carrying out photomodulatory treatment at high energy fluences, it is possible to use various devices for cooling the skin. Cyrogenic sprays and cold water circulation systems are known in the art are suitable for this purpose. Such devices, however, have not been used previously to allow photomodulatory processes to occur at energy fluence levels that are normally associated with thermal injury.

The present invention is further illustrated by way of the following examples.

EXAMPLE 1

Wrinkle Reduction with Pulsed Treatment

A team of blinded expert graders viewing before and after photos of patients subjected to the non-ablative LILT ("Low Intensity Light Therapy") of the present invention score the global improvement of visible wrinkles prominent in the facial area.

Six females are treated to reduce wrinkles. The entire face of the patient is subjected to the light from the LED light source. Three treatments over 12 weeks to the entire face with 250 millisecond pulses, an interpulse delay of 100 milliseconds, and 100 repetitions, resulting in a total energy fluence of 70.0 milliJ/cm$^2$. The average reduction in wrinkles is shown in Table 1. The light source has a dominant emissive wavelength at 574 nm.

TABLE 1

| Week/Value | Averaged Value of Reduction |
| --- | --- |
| 0 weeks | 0% |
| 4 weeks | 28% |
| 8 weeks | 56% |
| 12 weeks | 64% |

EXAMPLE 2

Wrinkle Reduction with Infrared Blocking

A team of blinded expert graders viewing before and after photos of patients subjected to the non-ablative LILT ("Low Intensity Light Therapy") of the present invention score the global improvement of visible wrinkles prominent in the facial area.

Six females are treated to reduce wrinkles. The entire face of the patient is subjected to the light from the LED light source. Three treatments over 12 weeks to the entire face with 250 millisecond pulses, an interpulse delay of 100 milliseconds, and 100 repetitions, resulting in a total energy fluence of 30.0 milliJ/cm$^2$. The average reduction in wrinkles is shown in Table 3. The light source has a dominant emissive wavelength at 590 nm. An optical low-pass filter was placed over the light source to block the transmission of wavelengths longer than 700 nm.

TABLE 2

| Week/Value | Averaged Value of Reduction |
| --- | --- |
| 0 weeks | 0% |
| 4 weeks | 32% |
| 8 weeks | 63% |
| 12 weeks | 71% |

EXAMPLE 3

Wrinkle Reduction with Filtered Dye Laser

A team of blinded expert graders viewing before and after photos of patients subjected to the non-ablative LILT ("Low Intensity Light Therapy") of the present invention score the global improvement of visible wrinkles prominent in the facial area.

Six females are treated to reduce wrinkles. The entire face of the patient is subjected to the light from the dye laser light source. Three treatments over 12 weeks to the entire face with 0.2 millisecond pulses, an interpulse delay of 100 milliseconds, and 100 repetitions, resulting in a total energy fluence of 100.0 milliJ/cm$^2$ (a neutral density filter was placed over the light source to limit the total energy fluence). The average reduction in wrinkles is shown in Table 3. The light source has a dominant emissive wavelength at 560 nm with the use of an optical filter designed to diffract the emission spectrum of the dye laser to produce usable output in a +/−15 nm range relative to the dominant emissive wavelength.

TABLE 3

| Week/Value | Averaged Value of Reduction |
|---|---|
| 0 weeks | 0% |
| 4 weeks | 17% |
| 8 weeks | 23% |
| 12 weeks | 30% |

EXAMPLE 4

Wrinkle Reduction—Continuous Treatment

Six males are treated to improve cutaneous blood flow for the purpose of stimulating hair growth. Twelve weekly treatments are performed on each patient's scalp using a 50 second continuous wave produced by a metal halide light source filtered to reduce infrared wavelengths to avoid heating the skin above to threshold for thermal injury. The metal halide light source produces a dominant emissive wavelength of 420 nm. The target tissue receives a total energy fluence of approximately 100.0 milliJ/cm$^2$. Measuring cutaneous blood flow with a Doppler cutaneous blood flow meter in an environmentally controlled room indicates an average increase in cutaneous blood flow of 22% among the test subjects.

EXAMPLE 5

Wrinkle Reduction—Ultra Short Pulse Duration

A particularly advantageous treatment regimen of the present invention is illustrated by treating 6 photo-aged females for wrinkle reduction. Three treatments are administered over 12 weeks using a Ti-Sapphire laser light source. The the facial area of each patient is treated with a total energy fluence of approximately 60 milliJ/cm$^2$, per session, from 80 pulses with a duration of 10 picoseconds, with 100 milliseconds between each pulse. The target tissue of each patient exhibits a substantial increase in new collagen production, thereby reducing the visibility of wrinkles.

EXAMPLE 6

Wrinkle Reduction—Ultra Short Pulse Duration

Another particularly advantageous treatment regimen of the present invention is illustrated by treating 6 photo-aged females for wrinkle reduction. Three treatments are administered over 12 weeks using a 1064 nm Q switched Nd:YAG laser light source. The facial area of each patient is treated with a total energy fluence of approximately 40 milliJ/cm$^2$, per session, from 100 pulses with a duration of 5 nanoseconds, with 20 milliseconds between each pulse. The target tissue of each patient exhibits a substantial increase in new collagen production, thereby reducing the visibility of wrinkles.

EXAMPLE 7

Acne Reduction with Multiple, Simultaneous Light Sources

A particularly advantageous treatment regimen of the present invention is illustrated by treating patients exhibiting acne and acne scarring. Nine treatments are administered over 12 weeks using a combination of red (620 nm) and blue (415 nm) LEDs (the indicated wavelength for each being the dominant emissive wavelength). The facial area of each patient is treated with a total energy fluence of approximately 40 milliJ/cm$^2$ to 90 milliJ/cm$^2$, per session, from a simultaneous continuous wave of approximately 18 minutes in duration from both sources. Each patient exhibits a substantial decrease in visible acne and acne scarring as well as a reduction in the presence of acne bacteria.

EXAMPLE 8

Acne Reduction with Sequential Light Sources

A particularly advantageous treatment regimen of the present invention is illustrated by treating patients exhibiting acne and acne scarring. Nine treatments are administered over 12 weeks using a combination of red (620 nm) and blue (415 nm) LEDs (the indicated wavelength for each being the dominant emissive wavelength). The facial area of each patient is treated with a total energy fluence of approximately 40 milliJ/cm$^2$ to 90 milliJ/cm$^2$, per session, from a continuous wave of approximately 18 minutes in duration from the red LED and another continuous wave of approximately 18 minutes from the blue LED. Prior to exposure to the light source, the target tissue of each patient is treated with a 3% copper chlorophyllin solution. Each patient exhibits a substantial decrease in visible acne and acne scarring as well as a reduction in the presence of acne bacteria.

EXAMPLE 9

Acne Reduction with IGC

A particularly advantageous treatment regimen of the present invention is illustrated by treating patients exhibiting acne and acne scarring. Nine treatments are administered over 12 weeks using multiple LEDs, each having a dominant emissive wavelength of 810 nm, arranged in a 0.5 W/cm$^2$ array. The facial area of each patient is treated with a total energy fluence of approximately 40 milliJ/cm$^2$, per session, from a continuous wave of approximately 80 seconds in duration. Prior to exposure to the light source, the target tissue of each patient is treated with a 3% indocyanine green solution. Each patient exhibits a substantial decrease in visible acne and acne scarring as well as a reduction in the presence of acne bacteria.

I claim:

1. A method for the manipulation of collagen, fibroblast, and fibroblast-derived cell levels in mammalian tissue comprising:

exposing said tissue to a plurality of pulses from at least one source of narrowband, multichromatic electromagnetic radiation having a dominant emissive wavelength of from about 300 nm to about 1600 nm; and filtering the source of narrowband, multichromatic electromagnetic radiation to regulate the transmission of infrared radiation to said tissue, wherein said pulses have a duration of from about 0.1 femtoseconds to about 100 seconds, the interpulse delay between said pulses is from about 0.1 to about 1000 milliseconds, and the energy fluence received by said tissue is less than about 10 joule per square centimeter and said source of narrowband, multichromatic electromagnetic radiation emits radiation in a bandwidth of about +/−100 nm wound the dominant emissive wavelength.

2. The method of claim 1 wherein said source of narrowband, multichromatic electromagnetic radiation is selected from a light emitting diode, a laser, a fluorescent light source, an organic light emitting diode, a light emitting polymer, a xenon arc lamp, a metal halide lamp, a filamentous light source, an intense pulsed light source, a sulfur lamp, and combinations thereof, and said dominant emissive wavelength is from about 400 nm to about 1600 nm.

3. The method according to claim 1 wherein the energy fluence received at said tissue is greater than 1 J/cm$^2$ and further comprises cooling said tissue.

4. The method according to claim 1 wherein the energy fluence received at said tissue is 1 J/cm$^2$ or less.

5. The method according to claim 4 wherein said energy fluence received at said tissue is from about from about $1\times10^{-6}$ J/cm$^2$ to 1 J/cm$^2$.

6. The method of claim 5 wherein said energy fluence received at said tissue is from about from about $1\times10^{-3}$ J/cm$^2$ to about 0.1 J/cm$^2$.

7. The method of claim 1 wherein said pulse length is from about 1 nanosecond to about 1 second.

8. The method of claim 7 wherein said pulse length is from about 5 nanoseconds to about 100 milliseconds.

9. The method of claim 1 further comprising applying a topical composition to said tissue, prior to exposing said tissue.

10. The method of claim 9 wherein said topical composition is selected from the group consisting of naturally occurring chlorophyll-containing compounds, carotenoid-containing compounds, phyocobilin compounds, indocyanine green, methylene blue, rose Bengal, Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a cofactor, an antiaging substance, insulin, minoxidil, lycopene, a natural or synthetic melanin, a metalloproteinase inhibitor, proline, hydroxyproline, an anesthetic, chlorophyll, bacteriochlorophyll, copper chlorophyllin, chloroplasts, carotenoids, phycobilin, rhodopsin, anthocyanin, inhibitors of ornithine decarboxylase, inhibitors of vascular endothelial growth factor (VEGF), inhibitors of phospholipase A2, inhibitors of S—adenosylmethionine, licorice, licochalone A, genestein, soy isoflavones, phtyoestrogens, derivative, analogs, homologs, and subcomponents thereof, and derivatives, subcomponents, immunological complexes and antibodies of said target tissue, and synthetic and natural analogs thereof, and combinations thereof.

11. The method of claim 1 further comprising cooling said tissue to maintain a temperature of said tissue below the threshold for thermal injury.

12. The method of claim 1 further comprising maintaining the temperature of said tissue at or below 38° C.

13. A method for the manipulation of collagen, fibroblast, and fibroblast-derived cell levels in mammalian tissue comprising:

exposing said tissue to at least one source of narrowband, multichromatic electromagnetic radiation having a dominant emissive wavelength of from about 300 nm to about 1600 nm for a period of time of from about 10 seconds to about 24 hours, wherein the energy fluence received by said tissue is less than about 10 J/cm$^2$ and said source of narrowband, multichromatic electromagnetic radiation emits radiation in a bandwidth of about +/−100 nm around the dominant emissive wavelength.

14. A method forte manipulation of collagen, fibroblast, and fibroblast-derived cell levels in mammalian tissue comprising:

exposing said tissue to at least one source of narrowband, multichromatic electromagnetic radiation having a dominant emissive wavelength of from about 300 nm to about 1600 nm for a period of time of from about 10 seconds to about 24 hours, wherein the energy fluence received by said tissue is less than about 10 J/cm$^2$ and said source of narrowband, multichromatic electromagnetic radiation emits radiation in a bandwidth of about +/−100 nm around the dominant emissive wavelength; and filtering the source of narrowband, multichromatic electromagnetic radiation to regulate the transmission of infrared radiation to said tissue.

15. The method according to claim 14 wherein the energy fluence received at said tissue is 1 J/cm$^2$ or less.

16. The method according to claim 14 wherein the energy fluence received at said tissue is greater than 1 J/cm$^2$ and further comprises cooling said tissue.

17. The method of claim 14 wherein said source of electromagnetic radiation is filtered to reduce the perception by said tissue of radiation having a wavelength greater than about 700 nm.

18. The method of claim 14 wherein said source of narrowband, multichromatic electromagnetic radiation further comprises a filter element for reducing the intensity of infrared radiation received by said tissue.

19. The method according to claim 18 wherein said energy fluence received at said tissue is from about from about $1\times10^{-6}$ J/cm$^2$ to 1 J/cm$^2$.

20. The method of claim 18 wherein said energy fluence received at said tissue is from about from about $1\times10^{-3}$ J/cm$^2$ to about 0.1 J/cm$^2$.

21. The method of claim 14 further comprising applying a topical composition to said tissue, prior to exposing said tissue.

22. The method of claim 21 wherein said topical composition is selected from the group consisting of naturally occurring chlorophyll-containing compounds, carotenoid-containing compounds, phyocobilin compounds, indocyanine green, methylene blue, rose Bengal, Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, a phytonutrient, plankton, a botanical product, a herbaceous product, a hormone, an enzyme, a mineral, a cofactor, an antiaging substance, insulin, minoxidil, lycopene, a natural or synthetic melanin, a metalloproteinase inhibitor, proline, hydroxyproline, an anesthetic, chlorophyll, bacteriochlorophyll, copper chlorophyllin, chloroplasts, carotenoids, phycobilin, rhodopsin, anthocyanin, inhibitors of ornithine decarboxylase, inhibitors of vascular endothelial growth factor (VEGF), inhibitors of phospholipase A2, inhibitors of S—adenosylmethionine, licorice, licochalone A, genestein, soy isoflavones, phtyoestrogens, derivative, analogs, homologs, and subcomponents thereof, and derivatives, subcomponents, immunological complexes and antibodies of said target tissue, and synthetic and natural analogs thereof, and combinations thereof.

23. The method of claim 14 further comprising cooling said tissue to maintain a temperature of said tissue below the threshold for thermal injury.

24. The method of claim 14 further comprising the step of maintaining the temperature of said tissue at or below 38° C.

* * * * *